United States Patent [19]

Okamoto et al.

[11] Patent Number: 5,754,618
[45] Date of Patent: May 19, 1998

[54] IMAGE PROCESSING APPARATUS AND IMAGE PROCESSING METHOD FOR FAVORABLY ENHANCING CONTINUOUS BOUNDARIES WHICH ARE AFFECTED BY NOISE

[75] Inventors: Tadashi Okamoto, Osaka; Yoshiteru Mino, Hirakata; Hiroshi Kadota, Toyonaka, all of Japan

[73] Assignee: Matsushita Electric Industrial, Osaka-fu, Japan

[21] Appl. No.: 772,756

[22] Filed: Dec. 23, 1996

[30] Foreign Application Priority Data

Dec. 22, 1995 [JP] Japan .................................. 7-334570
Dec. 22, 1995 [JP] Japan .................................. 7-334571
Jan. 24, 1996 [JP] Japan .................................. 8-009760

[51] Int. Cl.⁶ .................................................. G06K 9/00
[52] U.S. Cl. ...................................... 378/4; 378/901
[58] Field of Search ............................... 378/4, 19, 901, 378/62; 128/653.1, 653.2, 916; 382/131, 154, 285

[56] References Cited

U.S. PATENT DOCUMENTS 4,885,688  12/1989  Crawford .
4,920,573  4/1990   Rhodes et al. .................. 378/901 X
4,984,159  1/1991   Gullberg ........................... 378/901 X
5,283,837  2/1994   Wood ................................ 378/901 X Primary Examiner—David P. Porta
Attorney, Agent, or Firm—Price, Gess & Ubell

[57] ABSTRACT

An image processing apparatus which performs a process which enhances incongruous pixel values in an original image, including an object pixel selecting unit for selecting an object pixel out of pixels which compose the original image, a plurality n of filter units, each of which extracts pixel values of a set of pixels, including the selected object pixel, on one of a predetermined surface and a predetermined line which pass through the object pixel, out of pixels in a predetermined range, wherein each predetermined surface and predetermined line is at a different inclination, a relative size comparing unit for comparing pixels values of each set of pixels extracted by each filter unit and specifying a filter unit whose pixel values best approximate to a predetermined standard, and a first pixel value enhancing unit for enhancing a pixel value of the object pixel based on only the pixel values of the specified filter unit.

56 Claims, 84 Drawing Sheets

FIG. 8

| FOUR-WAY FILTER |
|---|
| No.1 180° DIRECTION |
| f31, f32, f33, f34, f35 |
| AVERAGE VALUE FOR SEARCH LINE SEGMENT L(1) |
| No.2 135° DIRECTION |
| f11, f22, f33, f44, f55 |
| AVERAGE VALUE FOR SEARCH LINE SEGMENT L(2) |
| No.3 90° DIRECTION |
| f13, f23, f33, f43, f53 |
| AVERAGE VALUE FOR SEARCH LINE SEGMENT L(3) |
| No.4 45° DIRECTION |
| f51, f42, f33, f24, f15 |
| AVERAGE VALUE FOR SEARCH LINE SEGMENT L(4) |

FIG. 9A
| f11 | f12 | f13 | f14 | f15 |
|-----|-----|-----|-----|-----|
| f21 | f22 | f23 | f24 | f25 |
| f31 | f32 | f33 | f34 | f35 |
| f41 | f42 | f43 | f44 | f45 |
| f51 | f52 | f53 | f54 | f55 |
f33 — OBJECT PIXEL
FIG. 9B
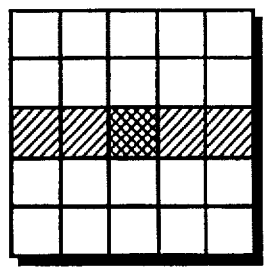
(FILTER 1)
(f31+f32+f33+f34+f35)/5
FIG. 9D
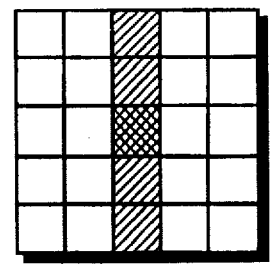
(FILTER 3)
(f13+f23+f33+f43+f53)/5
FIG. 9C
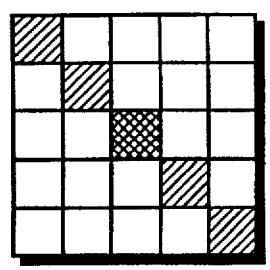
(FILTER 2)
(f11+f22+f33+f44+f55)/5
FIG. 9E
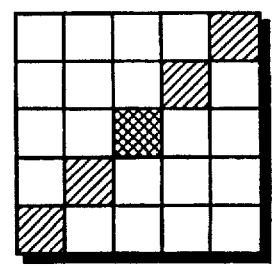
(FILTER 4)
(f51+f42+f33+f24+f15)/5

● · · · PIXEL ON OUTLINE
× · · · SPECKLE NOISE
P01 · · · OUTLINE PIXEL WITH MISSING PIXEL VALUE
P02 · · · OUTLINE PIXEL WITH MISSING PIXEL VALUE
P03 · · · PERIPHERAL PIXEL WITH MISSING PIXEL VALUE (FILTER 1)
(f31+f32+f33+f24+f15)/5

(FILTER 2)
(f11+f22+f33+f34+f35)/5

(FILTER 5)
(f51+f42+f33+f34+f35)/5

(FILTER 6)
(f31+f32+f33+f44+f45)/5

(FILTER 3)
(f13+f23+f33+f44+f55)/5

(FILTER 4)
(f15+f24+f33+f43+f53)/5

(FILTER 7)
(f11+f22+f33+f43+f53)/5

(FILTER 8)
(f13+f23+f33+f42+f51)/5

FIG. 16A

| F13 BRIGHTNESS 100 | F14 BRIGHTNESS 230 | F15 BRIGHTNESS 120 |
|---|---|---|
| F23 BRIGHTNESS 100 | F24 BRIGHTNESS 200 | F35 BRIGHTNESS 160 |
| F33 BRIGHTNESS 0 | F34 BRIGHTNESS 150 | F35 BRIGHTNESS 160 |

FIG. 16B

| F13 BRIGHTNESS 100 | F13 BRIGHTNESS 100 | F14 BRIGHTNESS 230 | F14 BRIGHTNESS 230 | F14 BRIGHTNESS 230 | F14 BRIGHTNESS 230 | F15 BRIGHTNESS 120 | F15 BRIGHTNESS 120 | F15 BRIGHTNESS 120 | F15 BRIGHTNESS 120 |
| --- | --- | --- | --- | --- | --- | --- | --- | --- | --- |
| F13 BRIGHTNESS 100 | F13 BRIGHTNESS 100 | F14 BRIGHTNESS 230 | F14 BRIGHTNESS 230 | F14 BRIGHTNESS 230 | F14 BRIGHTNESS 230 | F15 BRIGHTNESS 120 | F15 BRIGHTNESS 120 | F15 BRIGHTNESS 120 | F15 BRIGHTNESS 120 |
| F13 BRIGHTNESS 100 | F13 BRIGHTNESS 100 | F14 BRIGHTNESS 230 | F14 BRIGHTNESS 230 | F14 BRIGHTNESS 230 | F14 BRIGHTNESS 230 | F15 BRIGHTNESS 120 | F15 BRIGHTNESS 120 | F15 BRIGHTNESS 120 | F15 BRIGHTNESS 120 |
| F13 BRIGHTNESS 100 | F13 BRIGHTNESS 100 | F14 BRIGHTNESS 230 | F14 BRIGHTNESS 230 | F14 BRIGHTNESS 230 | F14 BRIGHTNESS 230 | F15 BRIGHTNESS 120 | F15 BRIGHTNESS 120 | F15 BRIGHTNESS 120 | F15 BRIGHTNESS 120 |
| F23 BRIGHTNESS 100 | F23 BRIGHTNESS 100 | F24 BRIGHTNESS 200 | F24 BRIGHTNESS 200 | F24 BRIGHTNESS 200 | F24 BRIGHTNESS 200 | F25 BRIGHTNESS 180 | F25 BRIGHTNESS 180 | F25 BRIGHTNESS 180 | F25 BRIGHTNESS 180 |
| F23 BRIGHTNESS 100 | F23 BRIGHTNESS 100 | F24 BRIGHTNESS 200 | F24 BRIGHTNESS 200 | F24 BRIGHTNESS 200 | F24 BRIGHTNESS 200 | F25 BRIGHTNESS 180 | F25 BRIGHTNESS 180 | F25 BRIGHTNESS 180 | F25 BRIGHTNESS 180 |
| F23 BRIGHTNESS 100 | F23 BRIGHTNESS 100 | F24 BRIGHTNESS 200 | F24 BRIGHTNESS 200 | F24 BRIGHTNESS 200 | F24 BRIGHTNESS 200 | F25 BRIGHTNESS 180 | F25 BRIGHTNESS 180 | F25 BRIGHTNESS 180 | F25 BRIGHTNESS 180 |
| F33 BRIGHTNESS 0 | F33 BRIGHTNESS 0 | F34 BRIGHTNESS 150 | F34 BRIGHTNESS 150 | F34 BRIGHTNESS 150 | F34 BRIGHTNESS 150 | F35 BRIGHTNESS 160 | F35 BRIGHTNESS 160 | F35 BRIGHTNESS 160 | F35 BRIGHTNESS 160 |
| F33 BRIGHTNESS 0 | F33 BRIGHTNESS 0 | F34 BRIGHTNESS 150 | F34 BRIGHTNESS 150 | F34 BRIGHTNESS 150 | F34 BRIGHTNESS 150 | F35 BRIGHTNESS 160 | F35 BRIGHTNESS 160 | F35 BRIGHTNESS 160 | F35 BRIGHTNESS 160 |
| F33 BRIGHTNESS 0 | F33 BRIGHTNESS 0 | F34 BRIGHTNESS 150 | F34 BRIGHTNESS 150 | F34 BRIGHTNESS 150 | F34 BRIGHTNESS 150 | F35 BRIGHTNESS 160 | F35 BRIGHTNESS 160 | F35 BRIGHTNESS 160 | F35 BRIGHTNESS 160 |

SUBPIXEL COORDINATE SYSTEM

SUBPIXEL COORDINATE SYSTEM MADE UP OF 20×20 SUBPIXELS

5×5×5 FILTER(1)

5×5×5 FILTER(2)

5×5×5 FILTER(3)

5×5×5 FILTER(4)

5×5×5 FILTER(5)

5×5×5 FILTER(6)

5×5×5 FILTER(7)

5×5×5 FILTER(8)

5×5×5 FILTER(9)

FIG. 20

CURVED SURFACE NINE-WAY FILTER

| No. 1 NORMAL LINE (0,1,0) |
|---|
| f(1,3,5), f(2,3,5), f(3,3,5),f(4,3,5),f(5,3,5)<br>f(1,3,4), f(2,3,4), f(3,3,4),f(4,3,4),f(5,3,4)<br>f(1,3,3), f(2,3,3), f(3,3,3),f(4,3,3),f(5,3,3)<br>f(1,3,2), f(2,3,2), f(3,3,2),f(4,3,2),f(5,3,2)<br>f(1,3,1), f(2,3,1), f(3,3,1),f(4,3,1),f(5,3,1) |
| AVERAGE VALUE FOR SEARCH LINE SEGMENT L(1) |
| No. 2 NORMAL LINE (0,0,1) |
| f(3,1,5), f(3,2,5), f(3,3,5),f(3,4,5),f(3,5,5)<br>f(3,1,4), f(3,2,4), f(3,3,4),f(3,4,4),f(3,5,4)<br>f(3,1,3), f(3,2,3), f(3,3,3),f(3,4,3),f(3,5,3)<br>f(3,1,2), f(3,2,2), f(3,3,2),f(3,4,2),f(3,5,2)<br>f(3,1,1), f(3,2,1), f(3,3,1),f(3,4,1),f(3,5,1) |
| AVERAGE VALUE FOR SEARCH LINE SEGMENT L(2) |
| No. 3 NORMAL LINE (1,0,0) |
| f(1,1,3), f(1,2,3), f(1,3,3),f(1,4,3),f(1,5,3)<br>f(2,1,3), f(2,2,3), f(2,3,3),f(2,4,3),f(2,5,3)<br>f(3,1,3), f(3,2,3), f(3,3,3),f(3,4,3),f(3,5,3)<br>f(4,1,3), f(4,2,3), f(4,3,3),f(4,4,3),f(4,5,3)<br>f(5,1,3), f(5,2,3), f(5,3,3),f(5,4,3),f(5,5,3) |
| AVERAGE VALUE FOR SEARCH LINE SEGMENT L(3) |

5×5×5 FILTER(9)
FILTERS (10)−(16) ARE SUCCESSIVE 45° ROTATIONS ABOUT THE X−AXIS

5×5×5 FILTER(1)

FILTERS (2)−(8) ARE SUCCESSIVE 45° ROTATIONS ABOUT THE Z−AXIS

5×5×5 FILTER(17)

FILTERS (18)—(24) ARE SUCCESSIVE 45° ROTATIONS ABOUT THE Y−AXIS

Y-Z SURFACE FOR x=4

(0,0)    z=11    x (0,0)    z=17    x (0,0)    x=1    y (0,0)    x=4    y

FIG. 36B
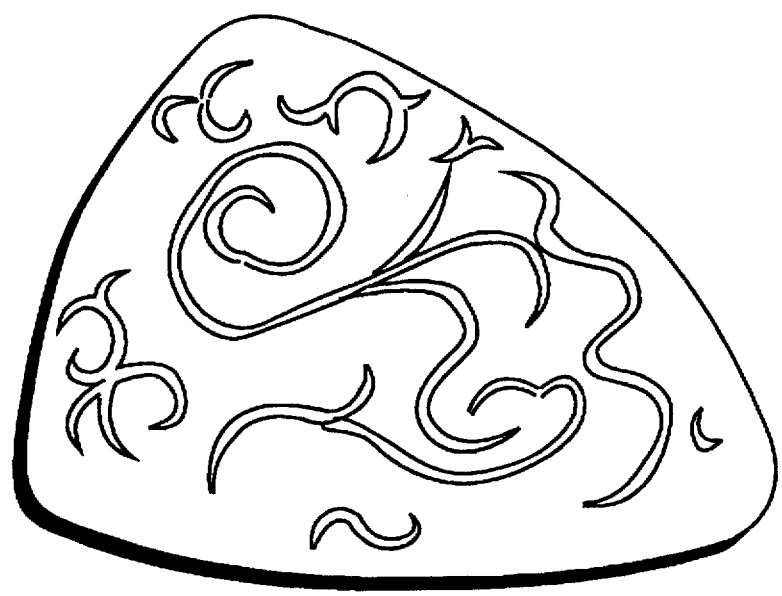
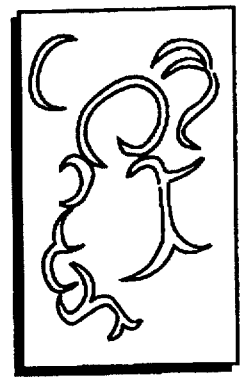

FRONT VIEW

UPPER VIEW

FIG. 43A  VECTOR SEARCH FILTER

| NUMBER | UNIT VECTOR | AVERAGE VALUE |
|---|---|---|
| 1 | (1,0,0) | |
| 2 | (0,1,0) | |
| 3 | (0,0,1) | |
| 4 | (−1,0,0) | |
| 5 | (0,−1,0) | |
| 6 | (0,0,−1) | |
| 7 | (1,1,0) | |
| 8 | (0,1,1) | |
| 9 | (1,0,1) | |
| 10 | (−1,1,0) | |
| 11 | (0,−1,1) | |
| 12 | (−1,0,1) | |
| 13 | (1,−1,0) | |
| 14 | (0,1,−1) | |
| 15 | (1,0,−1) | |
| 16 | (−1,0,−1) | |
| 17 | (0,−1,−1) | |
| 18 | (−1,−1,0) | |

FIG. 43B  PIXEL

| MONOCHROMATIC BRIGHTNESS 0−255 |
|---|
| COMPOSITE VECTOR ($\vec{x},\vec{y},\vec{z}$) |

FIG. 43C

| SURFACE INFORMATION |
|---|
| CENTER COORDINATES (xs,ys,zs) |
| NORMAL LINE VECTOR (p,q,r) |
| HEIGHT △L |
| WIDTH △W |

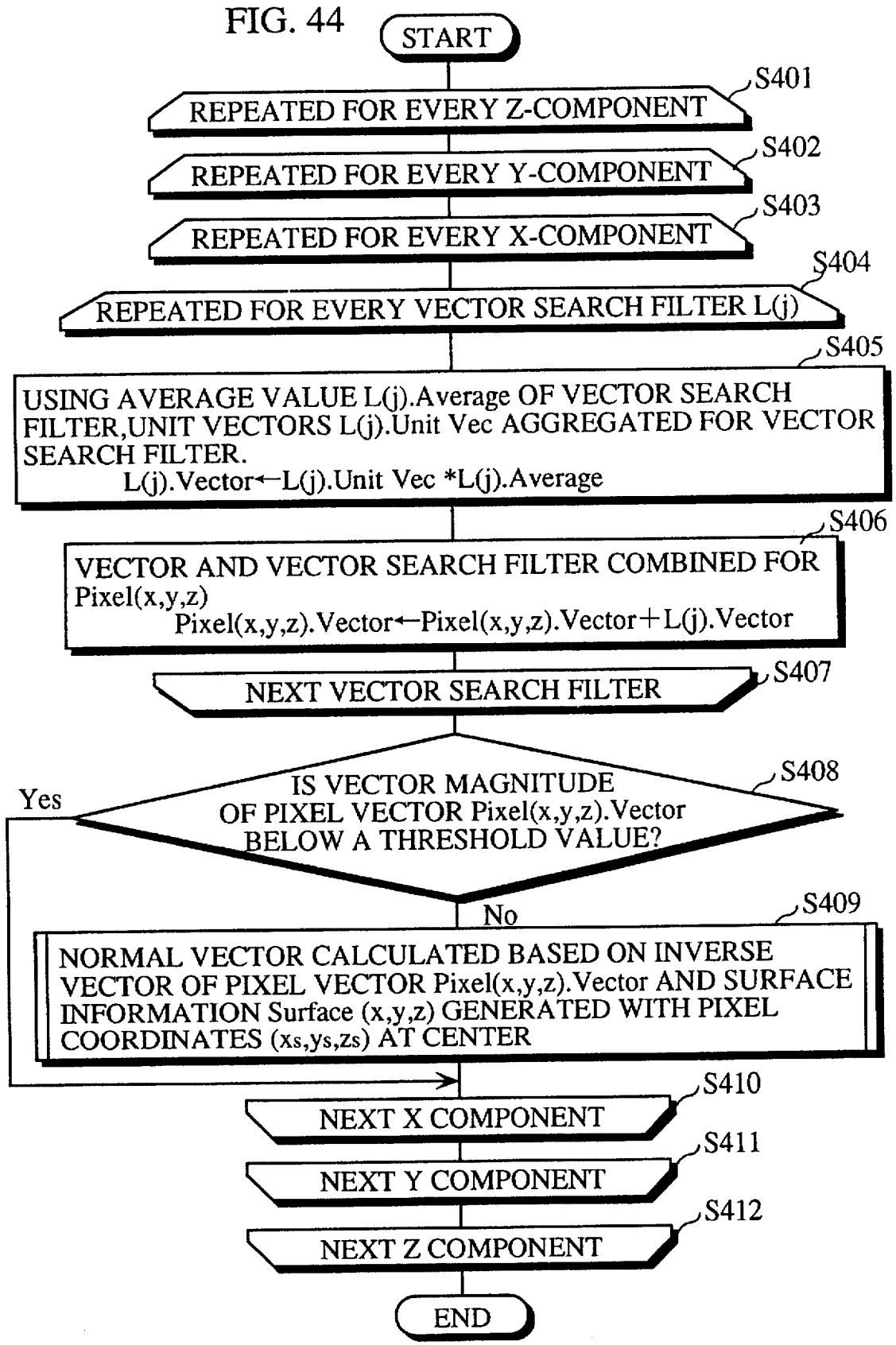

5,754,618

IMAGE PROCESSING APPARATUS AND IMAGE PROCESSING METHOD FOR FAVORABLY ENHANCING CONTINUOUS BOUNDARIES WHICH ARE AFFECTED BY NOISE

BACKGROUND OF THE INVENTION

1. Field of the Invention

The present invention relates to image enhancement and noise elimination, and more specifically is an improvement in image processing for medical images which are generated by ultrasound CT (Computed Tomography), X-ray CT, and MRI (Magnetic Resonance Imaging) CT.

2. Description of the Related Art

First Prior Art Technique

When compared to the dangers which can be caused by irradiation during X-ray CT or MRI CT, ultrasound CT has the advantage of having very little effect on the human body. The safety of ultrasound CT has been especially recognized in the field of fetal examination, and there has been a remarkable spread in its use in obstetrics and gynecology.

While superior in terms of safety, ultrasound CT is vastly inferior to X-ray CT and MRI CT in image quality. This deficiency in image quality can be due, for example, to the decrement of the ultrasound, or to the occurrence irregular reflection, multiple reflection, acoustic shadows, or side lobe. The details of such are described in *Advances in obstetrics and Gynecology Through the use of Ultrasound Computed Tomography*, Ichiro Baba, pub; Nagai Shoton. When an image of the face of a fetus, for example, is obtained using ultrasound CT, the outlines of the facial features are unclear so that, with a large incidence of noise, this results in a low-quality image. For medical staff to use such distorted tomograms in diagnosis, they have had to develop special skills, which is to say a method of visual tracing the broken outlines while ignoring distortions caused by noise.

When large amounts of speckle noise (noise whose occurrence is randomly distributed) are present near the outlines in tomograms, it becomes difficult to distinguish the outlines of the subject from speckle noise. In such a situation, even if an abnormality in the body should appear in the tomogram, there is the danger that the doctor examining the image will mistakenly dismiss the image corresponding to the abnormality as noise.

In order to improve the quality of tomograms, it is of course possible to join up the broken outlines using an image enhancement algorithm, such as one of those widely used in the field of image processing. Such methods, however, have the drawback that when there is a large incidence of speckle noise, such algorithms may mistake speckle noise for a part of an outline and so perform enhancement using speckle noise to form outlines. Should this occur, the image which is obtained by ultrasound CT will be somewhat different to the original subject.

Second Prior Art Technique

There have been many efforts in recent years to adapt ultrasound CT to form three-dimensional (3D) images. This has been performed by manually moving an ultrasound CT probe across, for example, the stomach of a pregnant woman to take a great number of tomograms with the probe in slightly different positions. These tomograms are then combined to form a three-dimensional image. By doing so, diagnosis can be performed using a three-dimensional image of the subject.

The combining of tomograms is performed by expressing each tomogram using an X-Y coordinate system and giving each level its own Z coordinate. This Z axis corresponds to the direction in which the probe is moved, so that the Z coordinates of different levels are only very slightly different to each other.

The combining of tomograms obtained through ultrasound CT to form a three-dimensional image, however, has a drawback in that interruptions to the outlines in each tomogram will show up in the final three-dimensional image as missing surfaces on the three-dimensional body. In order to avoid such omissions, it is desirable to compensate any missing parts in the outlines of each tomogram using an enhancement algorithm before combining the tomograms. Here, however, there can be oases where the individual enhancement of tomograms will result in problems with alignment. If tomograms which are not in alignment are combined, this can result in undulations in the surfaces of the subject image, so that parts of the image which have been enhanced become very difficult to examine.

Third Prior Art Technique

The three-dimensional images generated using the second prior art technique require a vast amount of data and so are unsuited to image processing. Here, the following explanation will describe the display of three-dimensional images using surface rendering (hereinafter, SR) as the prime example of a data format which is suited to image processing.

Surface rendering techniques express a subject using only its surface information, so that a great increase in processing speed can be achieved. There is also a further benefit in that less memory is necessary. Such methods, have a great disadvantage, however, in that accurate surface information needs to be obtained from the subject.

If, during the acquisition of surface information, there are missing surfaces, such as were described in the second prior art technique, or a large incidence of speckle noise, this will result in distorted surface information which, when subjected to SR, will produce an image which Is quite different to the original subject.

While the above explanation has described the above problems with reference to image formation using ultrasound CT, the same problems are also present with medical images obtained using X-ray CT or MRI CT. This is because X-ray CT and MRI CT still use input data which, in the same way as ultrasound CT, is gathered using a non-contact sensor and so is subject to the problems of speckle noise and broken outlines which were described above.

SUMMARY OF THE INVENTION

The first object of the present invention is to provide an information processing apparatus which can faithfully restore outlines to express the form of the original object, even when the image contains broken outlines and a high incidence of speckle noise.

The second object of the present invention is to provide an image processing apparatus which can effectively enhance surfaces in of a three-dimensional image which is generated by stacking sectional images with broken outlines.

The third object of the present invention is to provide an image processing apparatus which can generate an image which is faithful to an original image by extracting appropriate surface information from a three-dimensional image which is generated by stacking sectional images with broken outlines.

The first object of the present invention can be achieved by an image processing apparatus which performs a process which enhances incongruous pixel values in an original image, including: an object pixel selecting unit for selecting an object pixel out of pixels which compose the original image; a plurality n of filter units, each of which extracts pixel values of a set of pixels, including the selected object pixel, on one of a predetermined surface and a predetermined line which pass through the object pixel, out of pixels in a predetermined range, wherein each predetermined surface and predetermined line is at a different inclination; a relative size comparing unit for comparing pixels values of each set of pixels extracted by each filter unit and specifying a filter unit whose pixel values best approximate to a predetermined standard; end a first pixel value enhancing unit for enhancing a pixel value of the object pixel based on only the pixel values of the specified filter unit.

By means of the invention pixel values are extracted for pixels which are aligned in a given direction or on a given surface, so that a direction which has a high probability of corresponding to an outline can be specified. Once the direction has been specified, the pixel values of pixels which lie in this direction can be used to enhance the pixel value of the object pixel if they exceed a given threshold. By doing so, the object pixel is given a pixel value in keeping with the pixel values of the pixels which form the broken outline.

Here, the relative size comparing unit may include: an average value calculating unit for calculating an average value of the pixel values of the set of pixels extracted by each filter unit; and a specifying unit for setting possession of a highest average value as the predetermined standard and for specifying a filter unit which has a highest average value.

By means of the invention, speckle noise which is independent of its surrounding pixels will result in a low average value in any of the directions so that speckle noise can be distinguished from the broken part of the outline and set a pixel value of zero. By doing so, speckle noise can effectively be removed from the generated image. At the same time as speckle noise is removed, outlines are enhanced to become more clear, so that diagnosis can be made using a clear image formed by ultrasound.

The objects of the present invention can also be achieved by an image processing apparatus which performs a process which enhances incongruous pixel values in an original image, the image processing apparatus including: a object pixel selecting unit for selecting an object pixel out of pixels which compose the original image; a striplike area rotating unit for rotating a striplike area in a detailed coordinate system about the object pixel by a specified angle per rotation, wherein the detailed coordinate system is a coordinate system in which each pixel in the original image is expressed using a plurality of coordinate values which represent a two-dimensional region; a pixel detecting unit for calculating an intersecting area of a rotated striplike area and a region of each pixel in the original image; a distributing unit for assigning a weighting to a pixel value of each pixel whose region intersects the rotated striplike area, the weighting corresponding to a degree to which the rotated striplike area coincides with the region of the pixel; an indicating unit for indicating a rotation of the striplike area to the striplike area rotating unit, after pixel values have been weighted by the distributing unit; a relative size comparing unit for comparing, when rotating by the striplike area rotating unit has been repeated a predetermined number of times, weighted results for each rotation of the striplike area, and specifying a rotation whose weighted pixel values best approximate to a predetermined standard; and a first pixel value enhancing unit for enhancing the pixel value of the object pixel based on only the weighted pixel values of the specified filter unit.

By means of the invention, pixels are converted into a more detailed coordinate system so that a search area can be arranges so as to cross a plurality or pixels. A range indicated by the search points is then used to rewrite the pixel value of the object pixel, so that the pixel value of the object pixel can be rewritten with high precision.

The objects of the present invention can also be achieved by an image processing apparatus for enhancing an image of a three-dimensional body which is expressed by a plurality of sectional images which have been stacked together, the image processing apparatus including: a first planar image generating unit, set in a first direction which is at an angle to a stacking direction of the stacked plurality of sectional images, which is moved in the first direction across the image of the three-dimensional body to generate a plurality of first-direction planar images of the three-dimensional body; a first enhancing unit for enhancing each of the first-direction planar images and stacking the enhanced first-direction planar images in the first direction to generate a first enhanced image of the three-dimensional body; a second planar image generating unit, set in a second direction which is perpendicular to the first direction, which is moved in the second direction across the first enhanced image of the three-dimensional body to generate a plurality of second-direction planar images; a second enhancing unit for enhancing each of the second-direction planar images and stacking the enhanced second-direction planar images in the second direction to generate a second enhanced image of the three-dimensional body; a third planar image generating unit, set in a third direction which is perpendicular to the first direction and to the second direction, which is moved in the third direction across the second enhanced image of the three-dimensional body to generate a plurality of third-direction planar images; and a third enhancing unit for enhancing each of the third-direction planar images and stacking the enhanced third-direction planar images in the third direction to generate a third enhanced image of the three-dimensional body.

By means of the invention, a plurality of surfaces are generated for a three-dimensional body, with the broken outlines in these surfaces being amended, so that the three-dimensional image can be amended to become more faithful to the original image.

The objects of the present invention can also be achieved by an image processing apparatus for expressing a three-dimensional image, formed by stacking sectional images, as sets of surface information, each of which is made up of a normal vector and spatial coordinates, the image processing apparatus including: a unit vector providing unit for providing a plurality of unit vectors to each pixel which forms a part of a sectional image, wherein each unit vector shows one of a plurality of spatial directions; a weighting unit for analyzing how pixel values are distributed in each direction for a pixel and weighting each of the unit vectors provided to the pixel in accordance with the analysis result; a combining unit for combining the weighted unit vectors for every pixel; and a surface information generating unit for generating sets of surface information which each include spatial coordinates for a pixel and a normal vector which is based on the vector combined by the combining unit for the pixel.

For the invention, the magnitude of pixel values are analyzed in three-dimensions, so that a normal vector showing the inclination of the surface of the body is extracted and used to produce surface information which expresses the three-dimensional body. By doing so, the three-dimensional image produced by the surface information will be extremely faithful to the original body.

BRIEF DESCRIPTION OF THE DRAWINGS

These and other objects, advantages and features of the invention will become apparent from the following description taken in conjunction with the accompanying drawings which illustrate a specific embodiment of the invention. In the drawings:

FIG. 8 shows the data composition of the above four-way filter;

FIGS. 9A to 9E show the composition of the four-way filter;

FIG. 16A shows a 3*3 pixel grid;

FIG. 16B shows pixels which have been converted into a 12*12 subpixel grid;

FIG. 20 shows the data construction of a search surface filter;

FIGS. 36A and 36B show objects which have been processed using a shading process and a texture mapping process;

FIGS. 43A to 43C show the data construction of a vector search filter, the data construction of each pixel and the data construction of the surface information;

FIG. 44 shows the procedure for the calculation of surface information; and

DESCRIPTION OF THE PREFERRED EMBODIMENTS

The following is a description of the embodiments of the present invention, with reference to the drawings.

Figure 1:
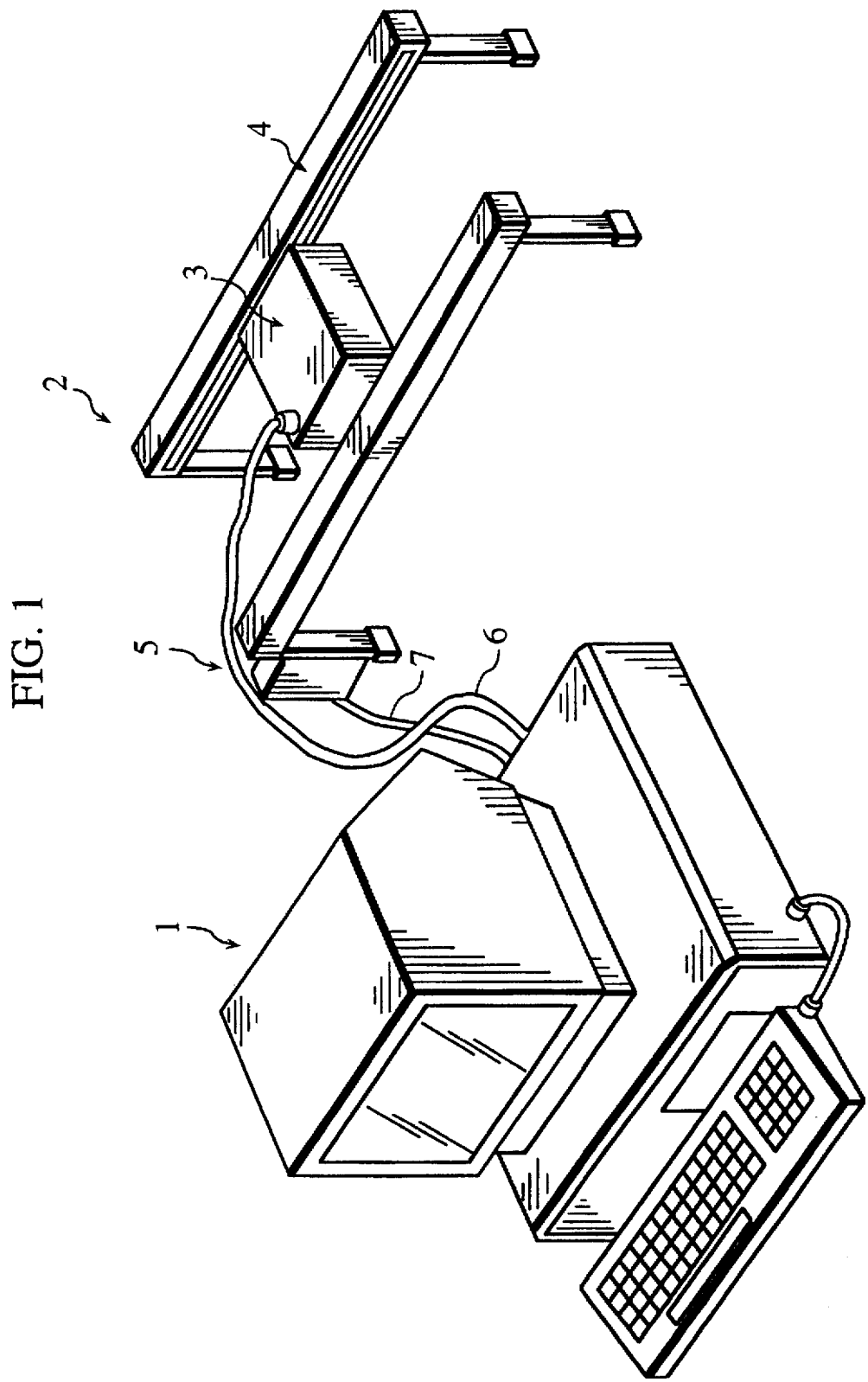
FIG. 1 shows the hardware construction of the image processing apparatus in the first emnbodiment of the present invention.

The hardware construction of the image processing apparatus of the first embodiment of the present invention is shown in FIG. 1. As shown in the drawing, the image processing apparatus is composed of a personal computer 1 and a measuring apparatus 2. This measuring apparatus 2 is made up of two construction rails 4 which are parallel, a probe 3 which is disposed between the construction rails 4, a slide construction 5 for sliding the probe 3 along the construction rails 4, and a cable 6 which connects the probe 3 to the personal computer 1.

The probe 3 exposes the subject to ultrasound based on control by the personal computer 1 and outputs the reception level of the reflected sound to the personal computer 1. Beneath the cover of the probe 3, a plurality of oscillation elements and a plurality of reception elements are arranged in rows. Each oscillation element oscillates to emit ultrasound which has a frequency of between 3.5 MHz and 5MHz. Ultrasound of this frequency band are reflected by parts of the subject in accordance with the density of their constituent matter. The reflected ultrasound waves are then received by the reception elements which output electrical signals expressing the reception level.

Cable 6 for connecting the probe 3 to the personal computer 1 is attached to the top of the case of probe 3, and is used to transmit the electrical signals outputted by the reception elements to the personal computer 1.

The probe 3 is controlled by the personal computer 1 and is made up of a driving circuit for driving the oscillation elements in order starting from one of the edges, an amplifier for amplifying the electrical signals which show the reception levels, an A/D converter for A/D converting the amplified electrical signals, a signal processing circuit for performing various kinds of signal processing for the converted digital information and outputting it via the cable 6 to the personal computer 1, and a timer for measuring the necessary time periods between the oscillation of the oscillation elements and the reception of the reflected ultrasound the reception elements and outputting the measured values as the distance of the position from which the ultrasound was reflected.

Figure 3:
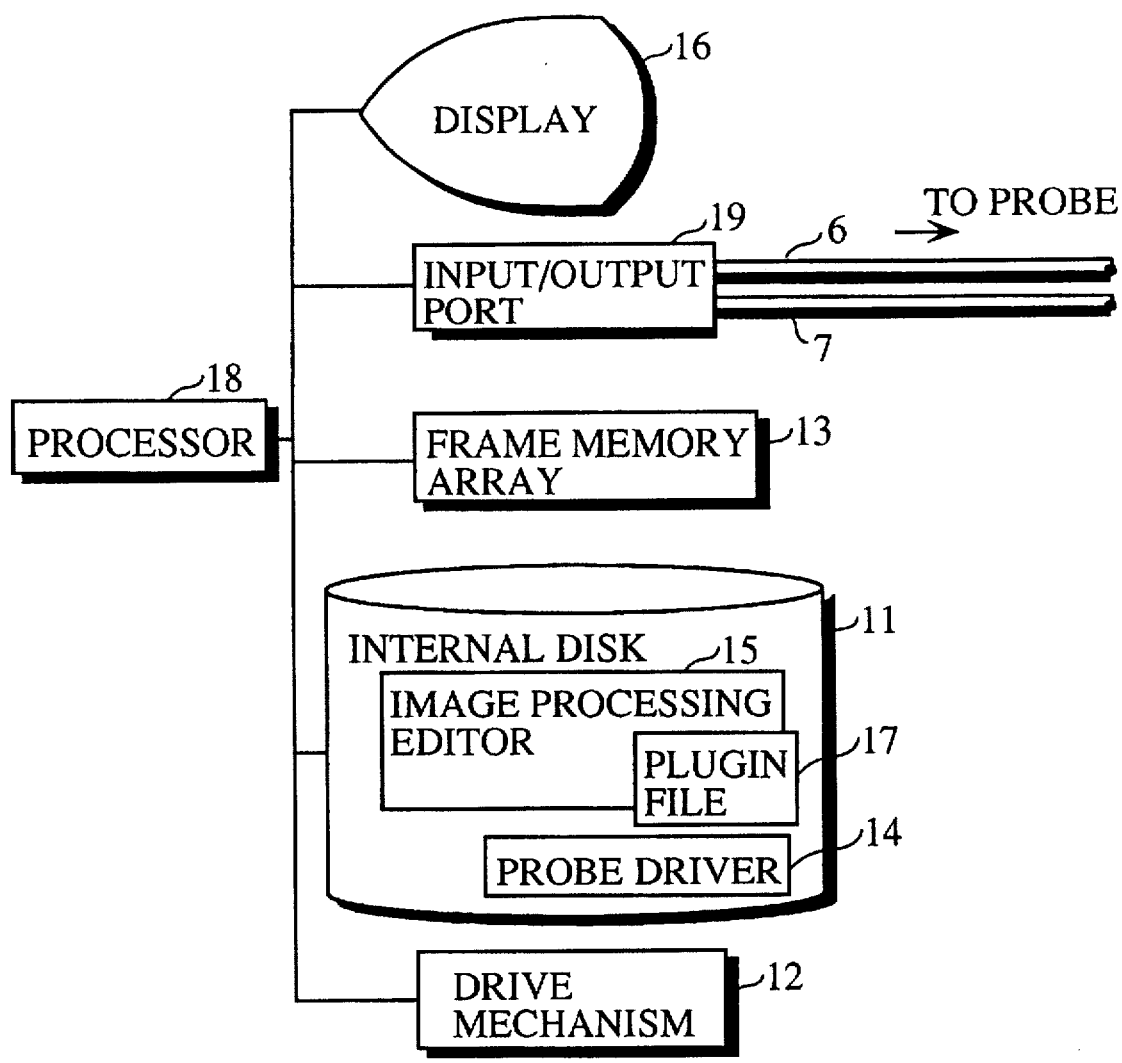
FIG. 3 shows the internal construction of the personal computer 1.

The internal construction of the personal computer 1 is shown in FIG. 3. As shown in FIG. 3, the personal computer 1 is made up of a hard disc 11, a drive mechanism 12, a frame memory array 13, a probe driver 14, an image processing editor 15, a display 16, a plugin file 17, and a processor 18.

The herd disc 11 stores various kinds of application programs, including the image processing editor 15.

The drive mechanism 12 installs applications which are recorded on a portable storage medium, such as an optical disc or floppy disc, onto the drive mechanism 12. Here, the probe driver 14, the image processing editor 16, and the plugin file 17 are all originally recorded on an optical disc, but are installed onto the hard disc 11 by the drive mechanism 12. This storage of the probe driver 14, the image processing editor 15, and the plugin file 17 is performed using a storage medium such as a floppy disc or optical disc since there is a high possibility that they will be packaged and marketed separately in the future.

Figure 5:
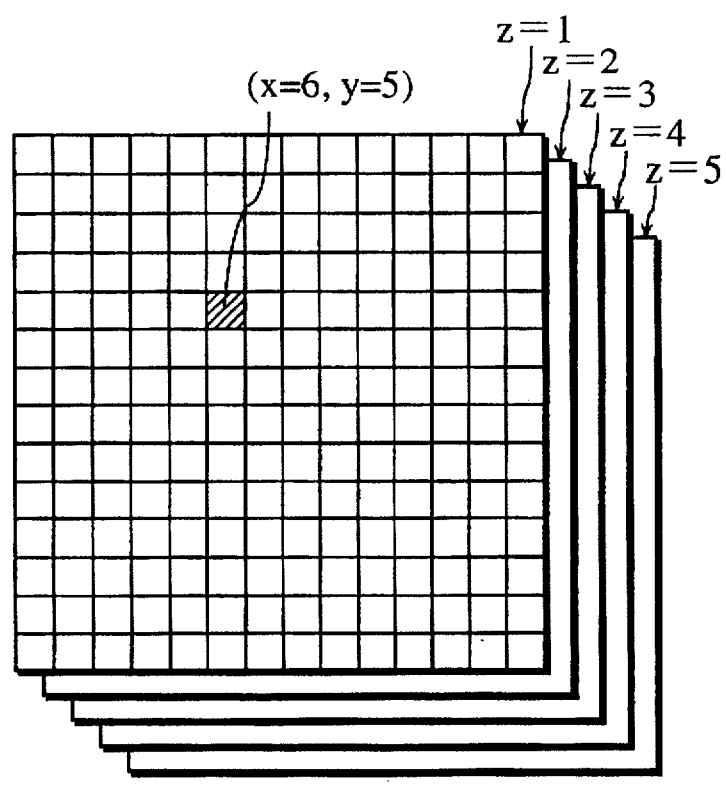
FIG. 5 shows the storage method for image data in the frame memory array.

The frame memory array 13 is composed of a plurality of frame memories and stores a plurality of tomograms. The storage method for the storage of such image data in the frame memory array 13 is shown in FIG. 5.

The frame memories which compose the frame memory array 13 are each allocated a Z coordinate and are used with switching between them being performed. Each frame memory assigns eight memory bits to each pixel and no stores a monochrome image which is composed or pixels in one of 256 shades of grey. Each of these values representing one pixel is also assigned coordinates for its position in the X and Y axes which are used when it is written-in or read-from the frame memory array 13 In the following example, the position of an arbitrary pixel in any of the frame memories is expressed using the notation "Pixel (x,y,z)", with the value of the pixel being expressed as "Pixel (x,y,z).Value". Here, any of the tomograms stored by the frame memory array 13 can be selectively displayed on the display 16 in accordance with a user indication.

The probe driver 14 controls the measuring apparatus 2 via the cables 6 and 7 and generates image data for each tomogram in the frame memory array 13. Each pixel in this image data is set so that the position of the oscillation element which emitted the ultrasound Is expressed using its X coordinate, the position from which the ultrasound was reflected is expressed as its Y coordinate, and the position to which the slide construction 5 has slid on the construction rails 4 is expressed as its Z coordinate.

Figure 2A:
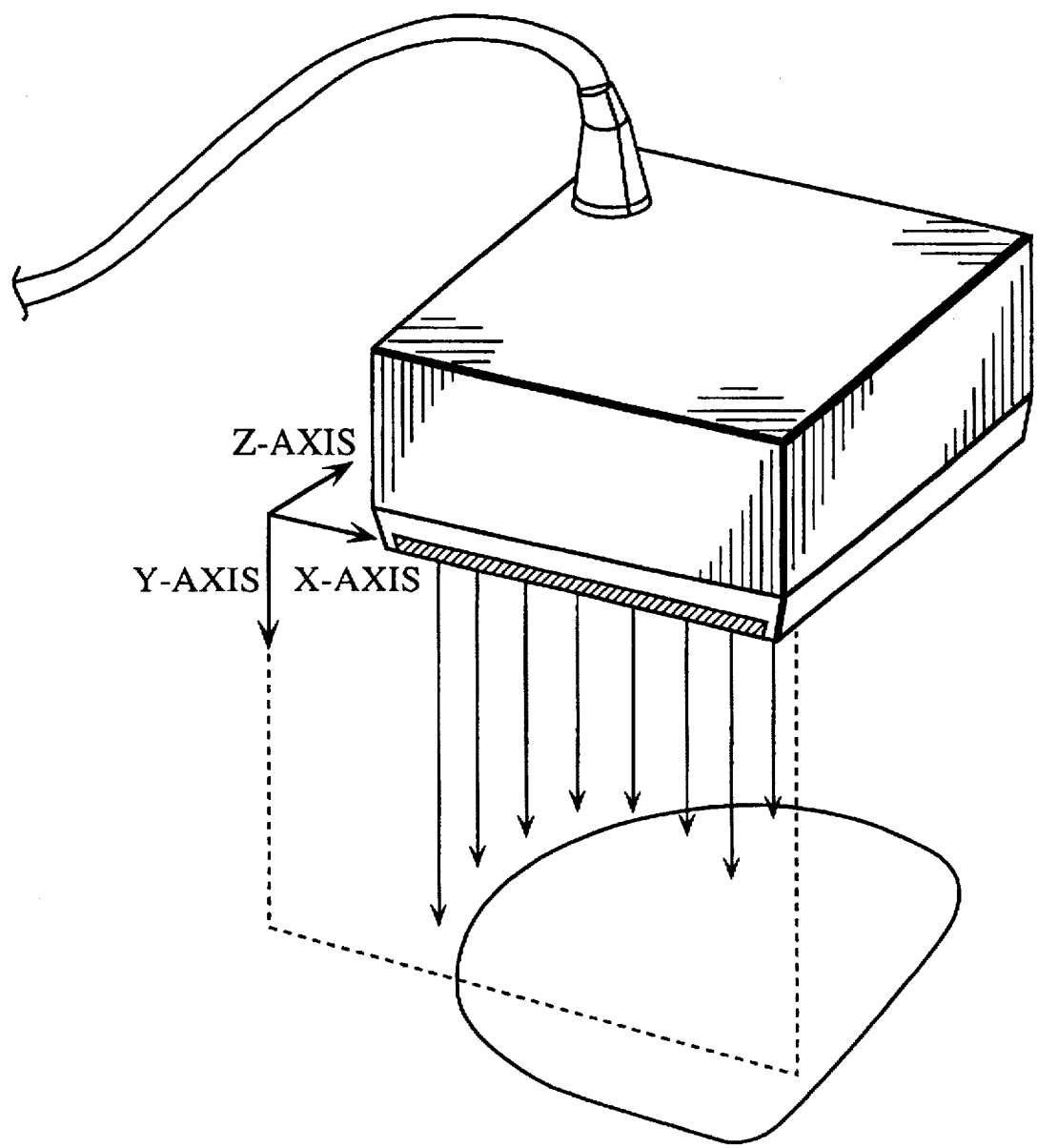
FIG. 2A shows a tomogram where, for probe 3, the direction in which the oscillation elements are arranged is as the X axis and the depth of the object being measured is set as the Y axis.

When the probe driver 14 issues oscillation orders to each of the oscillation elements provided in the probe 3, tomograms are obtained in the frame memory array 13 in which the direction in which the oscillation elements are arranged inside the probe 3 (shown in FIG. 2A) is set as the X axis and the depth of the position of reflection is set as the Y axis. Points of reflection of the ultrasound show parts of the subject where there is a significant change in the density of the constituent subject matter, so that by expressing distances to such points in the Y axis, it is possible to obtain a tomogram which is a representation of the boundaries where there are such changes in density. As one example, in examinations in the field of obstetrics and gynecology, an image showing the form of a fetus's cranium and nasal bone can be obtained by using a probe on an expectant mother.

Figure 2B:
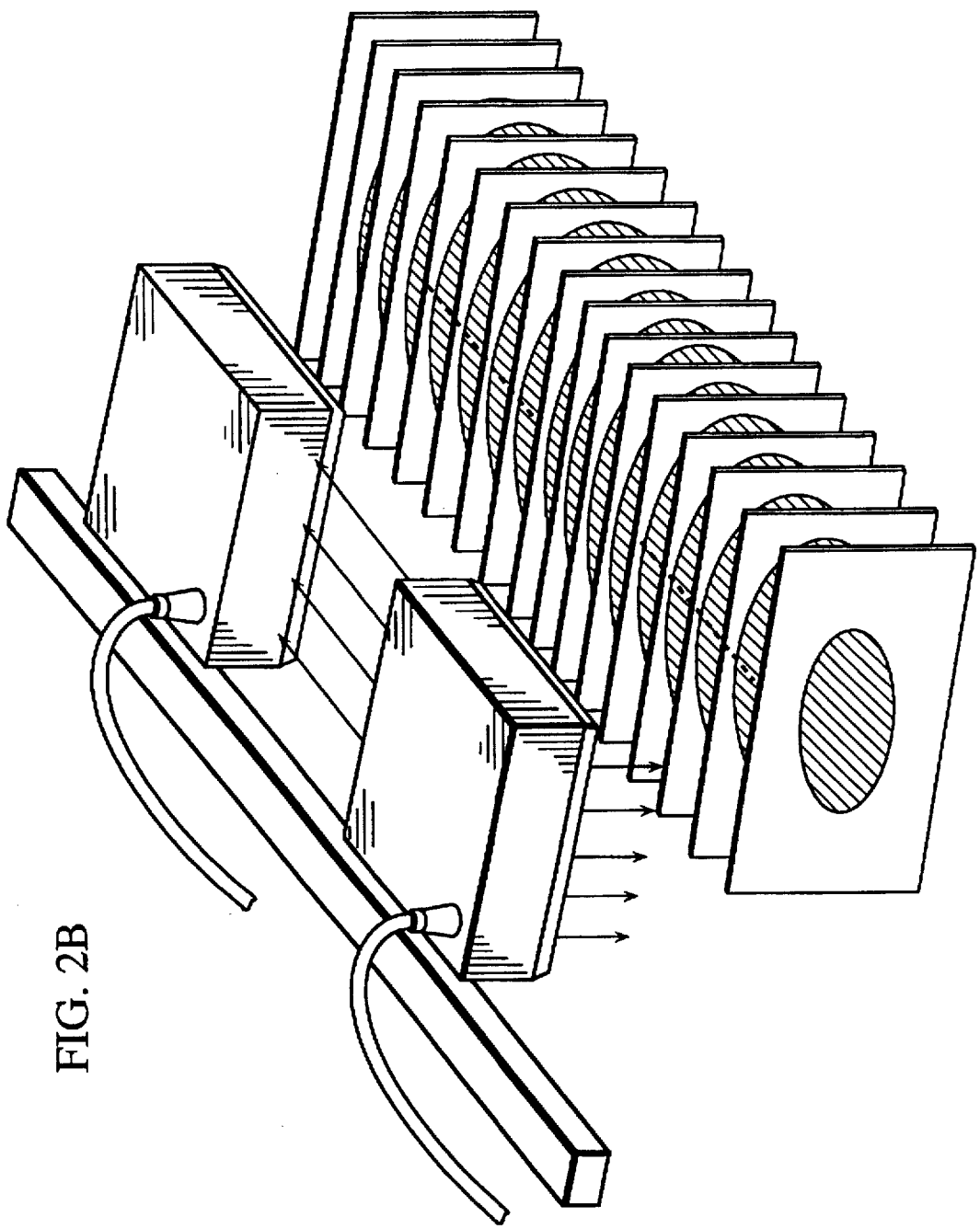
FIG. 2B shows tomograms where the amount moved by the probe 3 along the construction rails 4 is set as the 2 coordinate of each tomogram.

When there is a command to the measuring apparatus 2 to move the sliding mechanism of the probe 3, a plurality of tomograms are generated, as shown in FIG. 2B, where the repositioned amount of the probe 3 on the construction rails 4 set is as the Z coordinate of each tomogram.

The images which obtained through control by the probe driver 14 contain broken edges due to the decrement of ultrasound and a high incidence of noise due to the occurrence of irregular reflection, multiple reflection, and other such causes.

The image processing editor 15 uses the plugin file 17 to process the plurality of images stored in the frame memory and stores the processed images in a different frame memory.

The plugin file 17 is a file which stores a four-way filter, an eight-way filter and various other kinds of filters.

In general, image filters stabilize the distribution of pixel values in an image. Here, the stabilizing of the distribution of pixel values is achieved by altering the pixel levels of every pixel which composes the image to become a same level. In most cases, a weighted average of the pixel values of a plurality of pixels surrounding a given pixel is used as this "same level". This "plurality of pixels" collectively refers to all of the pixels in a predetermined area, out of all of the pixels which surround the pixel ("object pixel") to be adjusted Here, an example of a filter which uses a 5*5 grid as its predetermined area is shown in FIG. 6A.

Figure 6A:
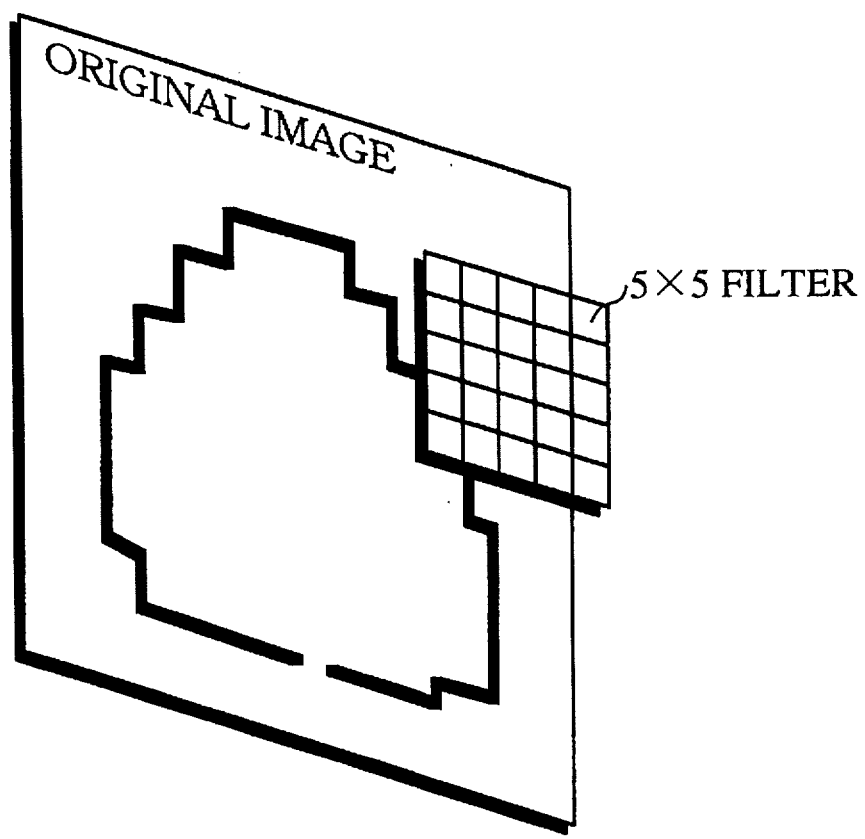
FIGS. 6A and 6B show the application of a filter which has a 5*5 grid.
Figure 6B:
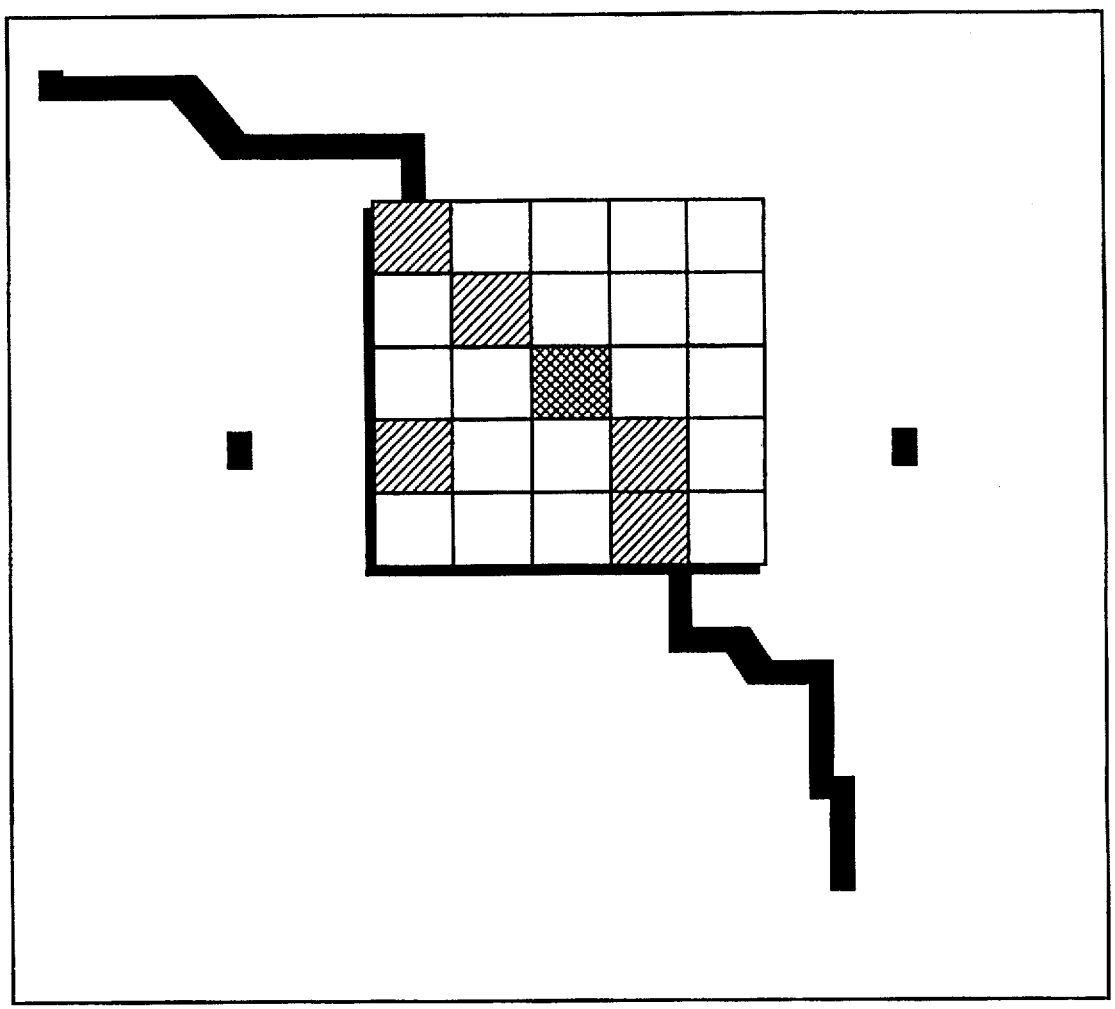

The setting of a level which is equal to the pixels surrounding the object pixel in FIG. 6A is performed using the pixels in a 5*5 grid which, as shown in FIG. 6B, has the object pixel as its center, with this set level then being substituted for the pixel level of the object pixel. By replacing pixel values in this way, even if the object pixel has a pixel value which is quite different to its surrounding pixels, its pixel value will be adjusted to a level which, in comparison with the surrounding pixels, is more even.

By replacing all of the pixels which compose the image in this way, a more even image can be achieved and the effects of noise which occurred during image formation become less prominent.

Out of the image filters stored by the plugin file 17, the four-way filter will be described first. Here, the term "four-way filter" refers to a filter which, in finding an even level, refers to the pixels surrounding the object pixel in any of four directions For the example shown in FIG. 7, these four directions are 45°, 90°, 135°, and 180° with respect to the X axis.

The search in each of the stipulated directions is performed using a "search line segment filter" in each direction. When the image processing editor 15 attempts to adjust the pixel level of an object pixel, It calculates an average value for each of a plurality of search line segment filters which correspond to the stipulated directions. When average values are calculated in this way, the average values for different search line segment filters can be compared with each other, with the search line segment filter with the highest average value can be ascertained.

In the above process, a plurality of search line segment filters compete with each other to be the filter used for calculation. This kind of "competition" is used to achieve a preferable enhancement of the broken outlines in the image. In general, pixels in a broken part of an outline have much lower pixels values than other pixels positioned on the outline, so that in order to enhance the broken part of the outline, pixels in the appropriate positions way be replaced by average values for their surrounding pixels. However, if an average of the pixel values in the 5*5 grid is used to replace the pixel, the average value will be calculated using pixel values which are not part of the outline. When there is a lot of speckle noise around the broken part of an outline, such speckle noise will end up be included in the enhancement of the broken part.

Figure 7:
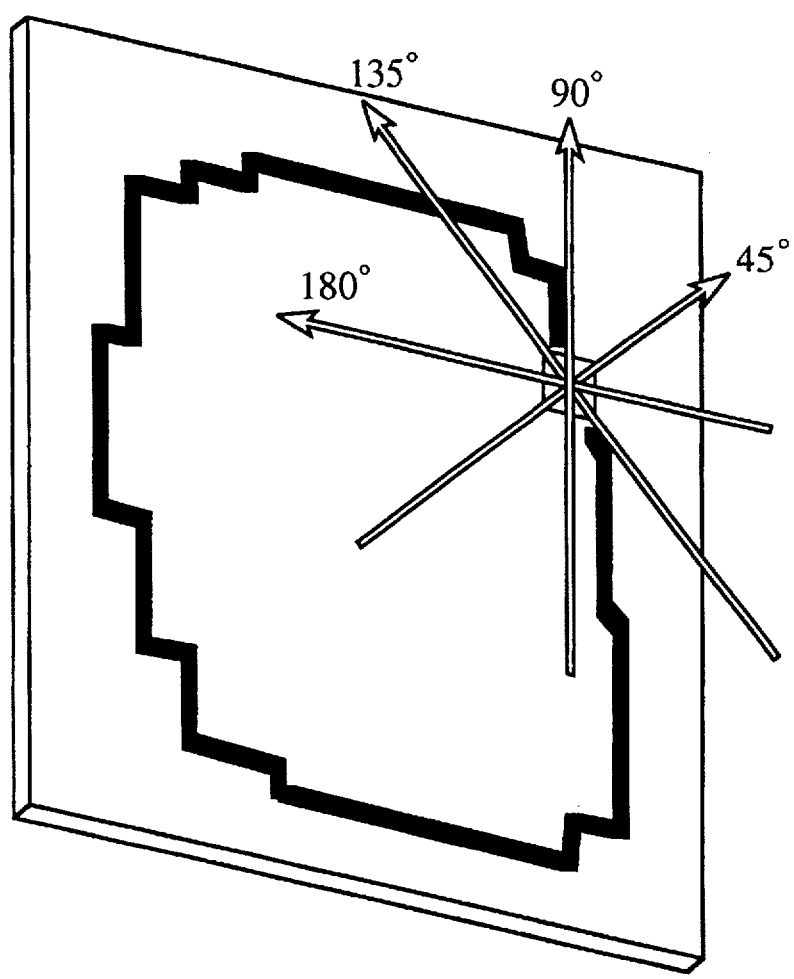
FIG. 7 shows a four-way filter where the directions have been set as 45°, 90°, 135°, and 180°, with respect to the X axis.

In response to the situation described above, a plurality of search line segment filters are prepared, as shown in FIG. 7, with an average value being calculated for each search line segment filter. When such average values are calculated, search line segment filters find an average value of pixels whose positioning corresponds to a potential direction of the outline, in doing so assigning a value zero to pixels which are not positioned in the potential direction of the outline.

By creating competition between search line segment filters over such average values, the search line segment filter which best approximates to the direction of the real outline is selected for object pixel enhancement of the broken outline part. By doing so, it can be assured that the average is taken for an area which includes the real outline, which means that only pixel values of pixels located on the outline are used to enhance missing pixel valves.

Figure 4:
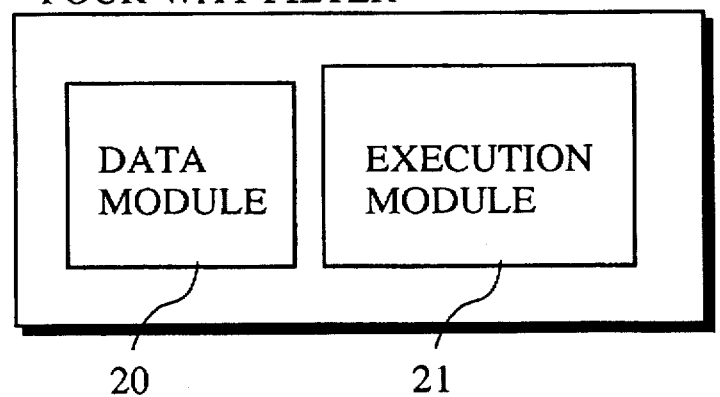
FIG. 4 shows the composition of a four-way filter.

The following is an explanation of the aforementioned four-way filter. As shown in FIG. 4, this filter is composed of a data module 20 and an execution module 21. Other filters are also used in the present embodiment, and these are also made up of two modules which are namely a data module and an execution module.

The data composition of the data module of the four-way filter is shown in FIG. 8. As shown in FIG. 8, each search line segment filter includes an array of search points which is the arrangement of search points which are labelled "f(m,n)" in the drawing, in addition to a space for recording the average value calculated by the search line segment filter from these search points. In the figure, the search line segment filters are consecutively numbered 1–4.

These consecutive numbers are expressed using the variable j which is explained later in this specification, so that the search line segment filter for number j is expressed by search line segment L(J). Similarly, the average value for the search line segment filter for number j is expressed as average value L(j).Average. The threshold used for judging speckle noise is set at a monochrome brightness level of 25 or below in the present embodiment, although this value has been chosen merely for ease of explanation, so that a preferable value will be set with consideration to the total brightness of the outlines and the speckle noise, to the intensity of the ultrasound emitted by the oscillation elements, and to the output level of the probe 3. To assist this setting of the threshold value, a preview of the enhanced image may by given by the probe driver 14.

As shown in FIG. 9, the subscript "m" in the search point "f(m,n)" indicates a pixel position "m–3" from the object pixel in the Y-axis, while the subscript "n" in the search point "f(m,n)" indicates a pixel position "n–3" from the object pixel in the X-axis. This subtraction of "3" from each level, as shown in FIG. 9A, is performed to position (x,y) =(3,3) in the center of the 5*5 grid used by the search line segment filter.

For the above arrangement, when the search point is "f34", a pixel which is displaced one space past the center in the X-axis is designated, while when the search point is "f45", a pixel which is displaced two spaces past the center in the X-axis and one space past the center in the Y-axis is designated. By storing arrays of search points as data which is expressed as "f31, f32, f33, f34, f35", the direction of a search line segment can be established.

In FIG. 8, the first search line segment filter is made up of search points "f31, f32, f33, f34, f35" which designate the search area for the direction 180° with respect to the X-axis. This is illustrated by the shaded area in FIG. 9B.

In the same FIG. 8, the second search line segment filter is made up of search points "f11, f22, f33, f44, f55", which designate the search area for the direction 135° with respect to the X-axis. This is illustrated by the shaded area in FIG. 9C. The third search line segment filter is made up of search points "f13, f23, f33, f43, f53", which designate the search area for the direction 90° with respect to the X-axis. This is illustrated by the shaded area in FIG. 9D. Finally, the fourth search line segment filter is made up of search points "f51, f42, f33, f24, f15", which designate the search area for the direction 45° with respect to the X-axis. This is illustrated by the shaded area in FIG. 9E.

By expressing search line segment filters as these arrays of search points, the process for establishing search points can be quickened. When such arrays are not prepared in advance, processor 18 has to trace search paths in each of the different search directions and specify each of the pixels which lies on the search path, which increases the load of processor 18. It should be noted here that when processor 18 has processing power to spare, it is not necessary to store search line segment filters in advance, so that they may be simply calculated as necessary. When doing so, the processor 18 may generate a virtual line segment in the image and, having rotated the line segment by an appropriate angle, then find the pixels which coincide with the rotated line segment.

Figure 10:
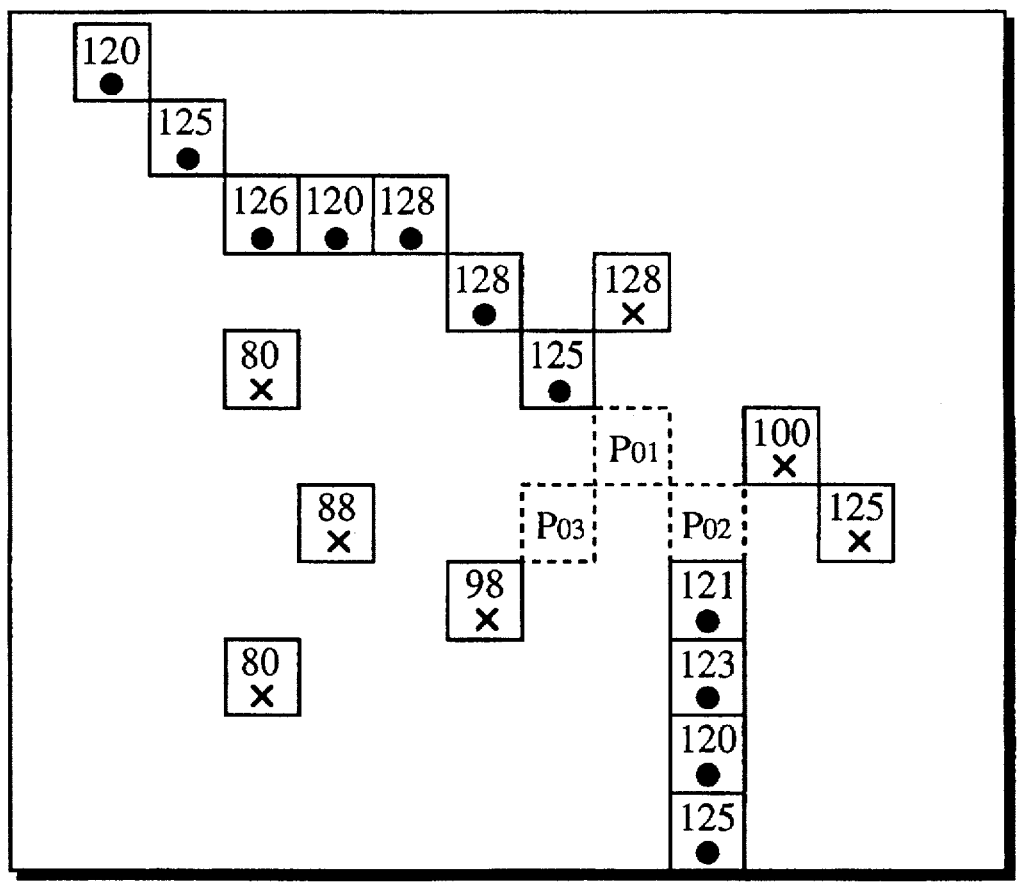
FIG. 10 shows a tomogram which includes a broken outline and speckle noise.

The following is an explanation of the enhancement of an image by finding an average value for each direction. The explanation refers to the image shown in FIG. 10 which suffers from a broken outline and speckle noise. In FIG. 10, each square represents a pixel, and pixels which are part of the outline have been indicated with black circles. Pixels marked with crosses "x" contain speckle noise. The numerical values written in squares range from 0 to 255 and represent the monochromatic brightness of each pixel.

In FIG. 10, P01 and P02 are pixels on the outline whose pixel values are missing, while point P03 is a pixel which is located in the area surrounding the outline whose pixel value is missing. The following is an explanation of average values are taken in each direction when calculating an average value for each of the pixels using a four-way filter.

Pixel P01

45° direction: (98+0+0+0+0)/5=19.6

90° direction: (128+0+0+0+0)/5=25.6

135° direction: (125+128+0+0+0)/5=50.6

180° direction: (100+0+0+0+0)/5=20

Pixel P02

45° direction: (100+0+0+0+0)/5=20

90° direction: (121+123+0+0+0)/5=48.8

135° direction: (125+0+0+0+0)/5=25

180° direction: (0+0+0+0+125)/5=25

Pixel P03

45° direction: (98+0+0+0+0)/5=19.6

90° direction: (125+0+0+0+0)/5=25

135° direction: (123+0+0+0+0)/5=20.6

180° direction: (0+0+0+0+0)5=0

By comparing the average values obtained for pixel P01, it can be seen that the highest average value 50.6 was obtained for the 135° direction. This average value reflects the presence of the pixel values 125 and 128 which are included in the outline, but does not reflect the presence of speckle noise around the pixel P01.

By comparing the average values obtained for pixel P02, it can be seen that the highest average value 48.8 was obtained for the 90° direction. This average value reflects the presence of the pixel values 121 and 123 which are included in the outline, but does not reflect the presence of speckle noise around the pixel P02.

By comparing the average values obtained for pixel P03, it can be seen that none of the average values in any direction exceeds the threshold value 25. When the average value in every direction is equal to or below the threshold, this means the corresponding point (in this case, point P03) is not a part of the outline and is most probably speckle noise. In such a case, the value of pixel P03 is set at zero to remove the effects of speckle noise.

Figure 11:
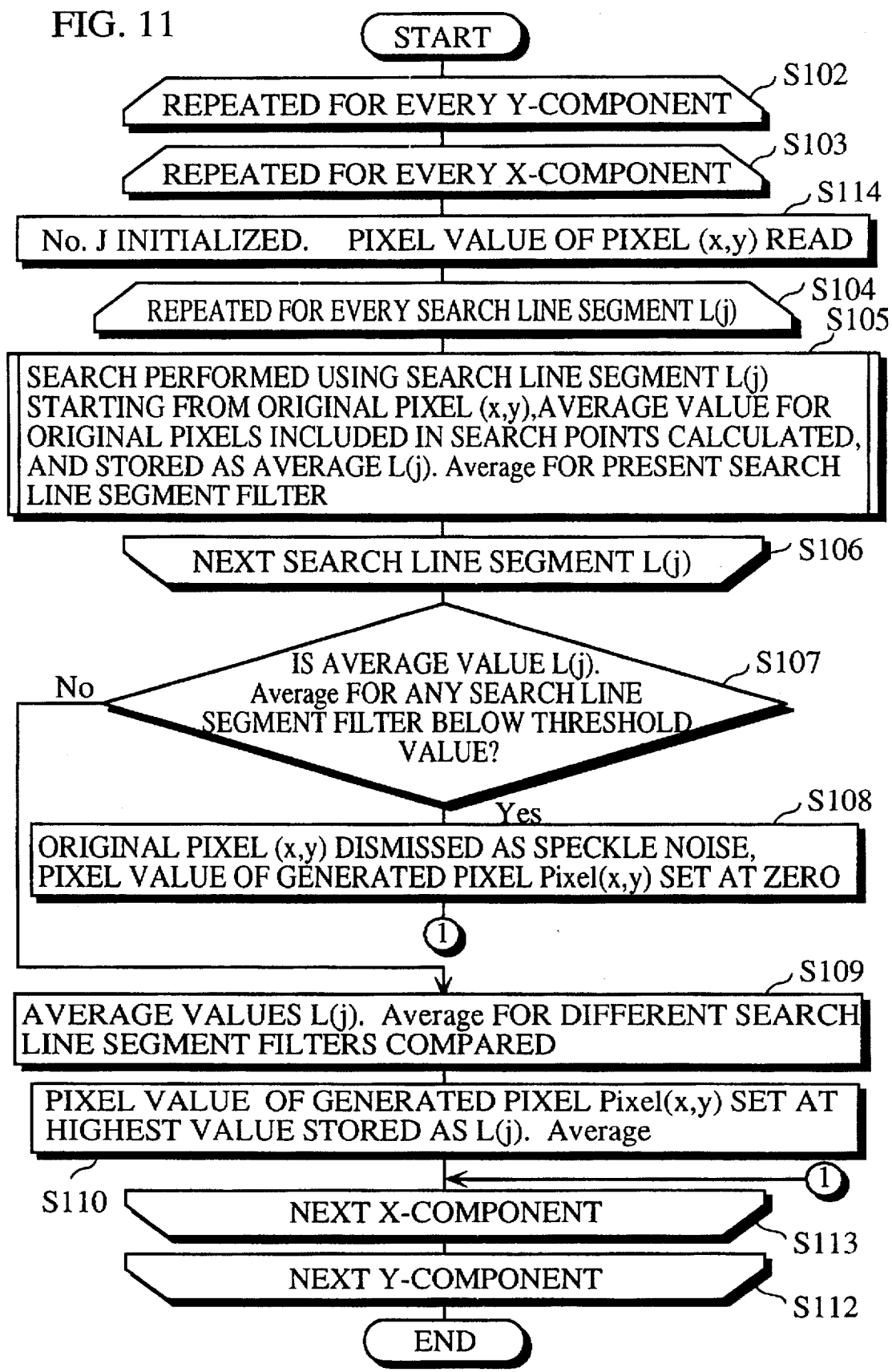
FIG. 11 is a flowchart showing the procedure for pixel enhancement using the four-way filter.

Image enhancement using this four-way filter is performed by an execution module of the processor 18 according to the procedure shown in FIG. 11. A loop process is performed between steps 103 and 113, with the X coordinate being incremented by one in each iteration, while another loop process is performed between steps 102 and 112, with the Y coordinate being incremented by one in each iteration. In step 114, the variable j is initialized and a pixel value "Pixel (x,y)" is read out of the pixels in one of the plurality of tomograms stored in the frame memory array 13, before the loop process of steps 104–106 is performed.

In step 104, the processor 18 reads the search line segment L(j) indicated by the variable j. In step 105, the processor 18 sets the original pixel (x,y), performs a search using the search line segment L(j), finds an average of the pixel values of the search pixels indicated by the search line segment L(j), and stores the calculated value as "L(j).Average" for current search line segment. In step 106, the variable j is incremented by one, a next search line segment L(j) is indicated and the processing returns to step 104.

Figure 12:
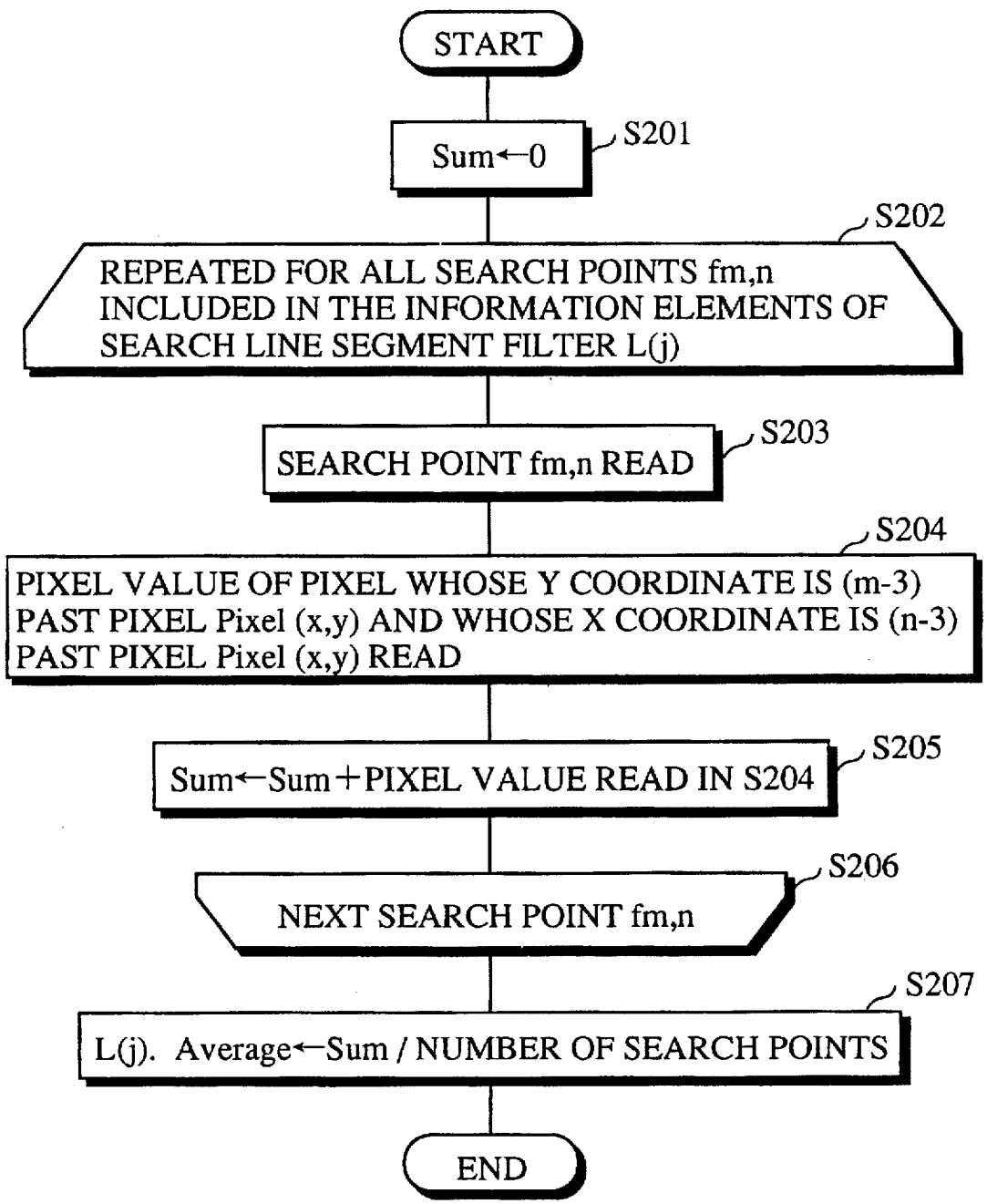
FIG. 12 is a flowchart showing the details of the processing in step 105 in FIG. 11.

A flowchart for the more specific subroutines which compose the procedure in step 105 is shown in FIG. 12. This will be used to explain the details of the processing in step 105 and the processing by the processor 18. In step 201 of FIG. 12, processor 1B resets the Sum value to zero. In step 202 and step 206, processor 18 controls the execution of the loop made up of steps 203–205 for each of the search points "f(m,n)" which are included in the search line segment L(j). In step 203, search point f(m,n) is read and in step 204, a pixel value of a pixel which is (m–3) past pixel (x,y) in the Y-axis and (n–3) past pixel (x,y) in the X-axis is read. After the pixel value has been read, it is added to the Sum value in step 205. This loop is repeated until it has been performed for all of the search points.

As one example, when the search line segment filter indicated by the variable j in step 104 is the 135° filter, by repeating step 204, the pixel values for f11, f22, f33, f44 and f55 are consecutively read and their sum (125+128+0+0+0 for point P01) is calculated in step 205. Once the iterations of this loop have been completed, the Sum value is divided by the number of search points (value N1) and the calculated result (125+0+0+0+0)/5=50.6 is given. Processor 18 then stores the calculation result as the average value L(j). Average for the search line segment.

As a different example, when the search line segment filter indicated by the variable j in step 104 is the 45° filter, by repeating step 204, the pixel values for f51, f42, f33, f24 and f15 are consecutively read and their sum (98+0+0+0+0 for point P03) is calculated in step 205. Once the iterations of this loop have been completed, the Sum value is divided by the number of search points (value N1) and the calculated result (98+0+0+0+0)/5=19.6 is given. Processor 18 then stores the calculation result as the average value L(j). Average for the search line segment.

Once a complete set of processing in FIG. 12 has been performed, it is determined in step 107 whether all of the average values L(j).Average of the search line segments is equal to or below the threshold value, with method for calculating the pixel value which is given to the generated pixel depending on this determination result. Here, a "generated pixel" refers to a pixel in the generated image, which is to say a pixel which is newly generated by image processing editor 15. These generated pixels are assigned to a different frame memory 13 as the original image, although, in the same way as the original image, each pixel in the generated image in the different part of the frame memory 13 is designated using the variable (x,y) which is incremented in steps 102 and 103.

If it is determined in step 107 that every average value is equal to or below the threshold value, the pixel (x,y) in the original image is dismissed in step 108 as not forming part of the outline and the processor 18 sets it a pixel value of zero.

If it is determined that an average value is above the threshold value, then the average values L(j).Average for different search line segments are compared, When four-way average values are calculated (for Point P01) as shown below, it can be seen that the value for the 135° direction is the highest.

45° direction: (98+0+0+0+0)/5=19.6

90° direction: (128+0+0+0+0)/5=25.6

135° direction: (125+128+0+0+0)/5=50.6

180° direction: (100+0+0+0+0)/5=20

Once the search line segment filter with the highest average value has been established, in step 110 the highest average value L(j).Average is set as the pixel value "Pixel (x,y)" of the generated pixel, thereby completing the processing for the current pixel.

Eight-way Filter

As its name implies, an eight-way filter is a filter which searches in eight directions, although, unlike the aforementioned four-way filter, the form of each of its constituent filters is set in accordance with the shape of the object to be measured, so that a more accurate enhancement of the image can be made. For an example where the subject is a fetus, the main object of attention is the head which develops relatively quickly, so that the outline will be made up of curved lines, such as circular or elliptic line segments. Based on these assumptions, if the search for pixels during image enhancement is performed by tracing circular or elliptic lines, a more accurate image can be achieved for a fetus's head, for example, which is composed of such lines.

Figure 13A:
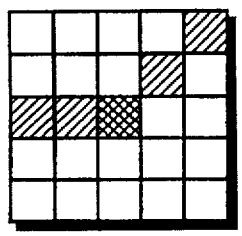
FIGS. 13A to 13H show a circular outline indicated by search line segment filters.

Examples of search line segment filters for circular outlines are shown in FIGS. 13A to 13H. These circular line segments are each a 45° segment of a circle which has a radius of eight pixels and which has been divided as shown in FIG. 14. Here, search line segment filter 1 shown in FIG. 13A is composed of search points f31, f32, f33, f24, and f15, and corresponds to the 270°–315° sector of the circle shown in FIG. 14.

Figure 13B:
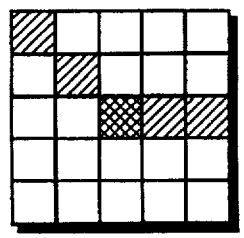
Figure 14:
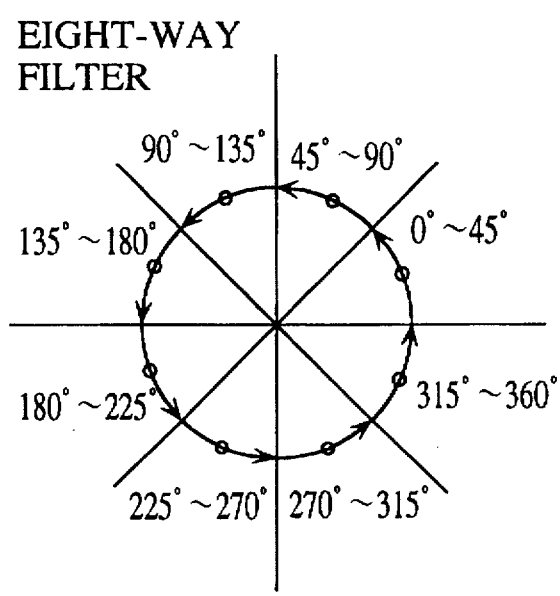
FIG. 14 shows the sectors of a circle.

Search line segment filter 2 shown in FIG. 13B is composed of search points f11, f22, f33, f34, and f35, and corresponds to the 225°–270° a sector of the circle shown in FIG. 14.

Figure 13E:
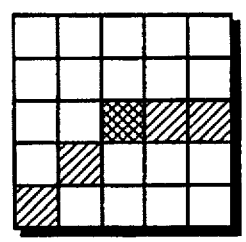
Figure 13F:
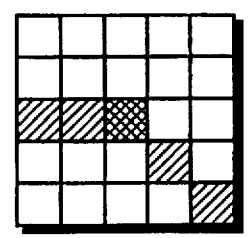
Figure 13C:
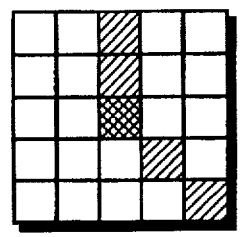

Search line segment filter 3 shown in FIG. 13C is composed of search points f13, f23, f33, f44, and f55, and corresponds to the 180°–225° sector of the circle shown in FIG. 14.

Figure 13D:
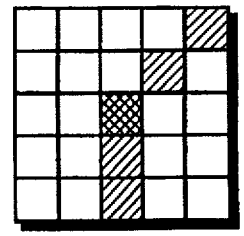

Search line segment filter 4 shown in FIG. 13D is composed of search points f15, f24, f33, f43, and f53, and corresponds to the 135°–180° sector of the circle shown in FIG. 14.

Search line segment filter 5 shown in FIG. 13E is composed of search points f51, f42, f33, f34, and f35, and corresponds to the 90°–135° sector of the circle shown in FIG. 14.

Search line segment filter 6 shown in FIG. 13F is composed of search points f31, f32, f33, f44, and f55, and corresponds to the 45°–90° sector of the circle shown in FIG. 14.

Search line segment filter 7 shown in FIG. 13E is composed of search points f11, f22, f33, f43, and f53, and corresponds to the 0°–45° sector of the circle shown in FIG. 14.

Figure 13G:
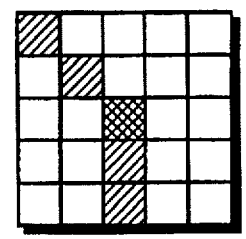
Figure 13H:
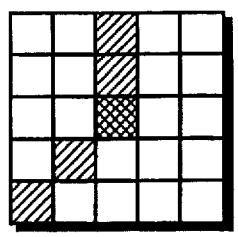

Search line segment filter 8 shown in FIG. 13G is composed of search points f13, f23, f33, f42, and f51, and corresponds to the 315°–360° sector of the circle shown in FIG. 14.

The eight-way filter shown in FIGS. 13A to 13H is set so that pixel values can be traced using the defined elliptical line segments, although different filters which are more faithful to the outline of the object may alternatively be used.

As described above, the apparatus of the present embodiment calculates average values using a plurality of search line segment filters of different search directions to help establish the direction of the outline in the searched area. By doing so, missing parts of an outline can be favorably enhanced using a pixel value which corresponds to the pixels which form the outline. In doing so, average values for areas which include nothing but random-occurring speckle noise will be low, no matter what search filter is used. As a result, demarcation between areas of speckle noise and pixel which are part of the original outline can be achieved and areas of speckle noise given a pixel value of zero, thereby totally removing the speckle noise from the generated image. This concurrent enhancement of outlines and removal of speckle noise leads to a dramatic improvement in the clarity of outlines, which improves the accuracy with which diagnosis based on ultrasound computed tomography can be made.

Second Embodiment

The second embodiment of the present invention performs the pixel search in each direction with greater precision, and accordingly has a twelve-way filter for searching in twelve directions stored in the plugin file 17. Such twelve-way search is performed using a striplike search area which is rotated in a subpixel coordinate system.

A subpixel coordinate system is a coordinate system in which each pixel is expressed using a plurality of subpixel, so that when, for example, an m*m coordinate system is used, m*m pixels are generated for each pixel in the original image. The generated pixels are called "subpixels" and are given a same pixel value as the corresponding pixel in the original image. As one example, FIG. 16B shows an image composed of 12*12 subpixels which is generated from the image represented by FIG. 16A when a 4*4 subpixel coordinate system is used for each original pixel. In this subpixel image, the subject image is included in the 4*4 subpixel area in the bottom left of the image.

The "striplike" search area of the present embodiment is expressed as a row of search points and an interval between search points. This interval, called the search radius, is set at a predetermined number of pixels.

Figure 15:
FIG. 15 shows the date composition of a twelve-way filter.

The data construction shown in FIG. 15 is used to store the angle of rotation and the search radius of the twelve-way filter. This twelve-way filter has a search radius which is included in search line segment filters no as to trace circles which are concentric with the center of the object pixel. The twelve-way filter also rotates the striplike area by the angle included in the search line segment with respect to the X-axis.

The following is an explanation of when the striplike area is rotated 45° and appropriate points at a multiples of a predetermined radius (in this example, 3 subpixels) are used as the center points of search pixels. Here, FIG. 17A shows the generated striplike area and search points in a 20 *20 subpixel grid.

Figure 17A:
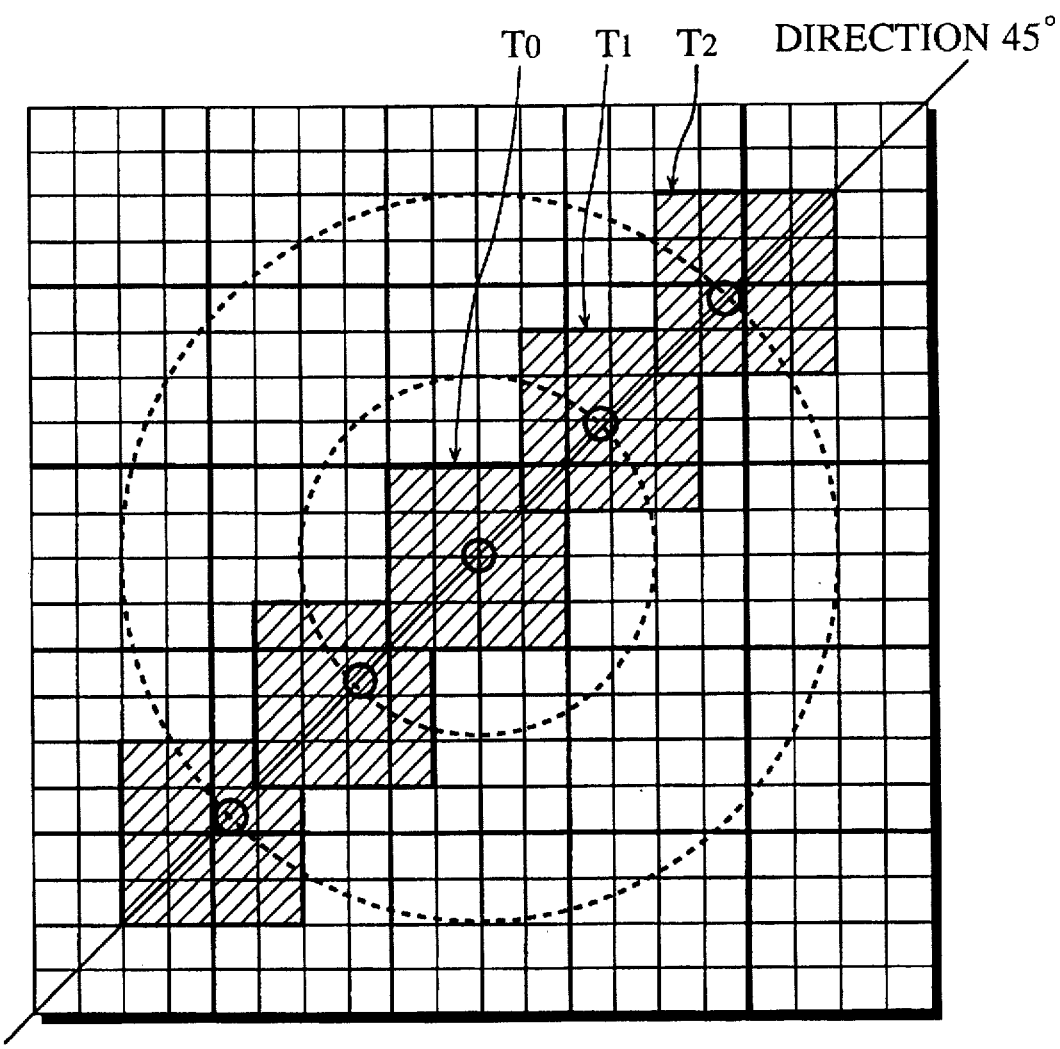
FIGS. 17A-17D show the range in which search pixels are found in the subpixel coordinate system.
Figure 17B:
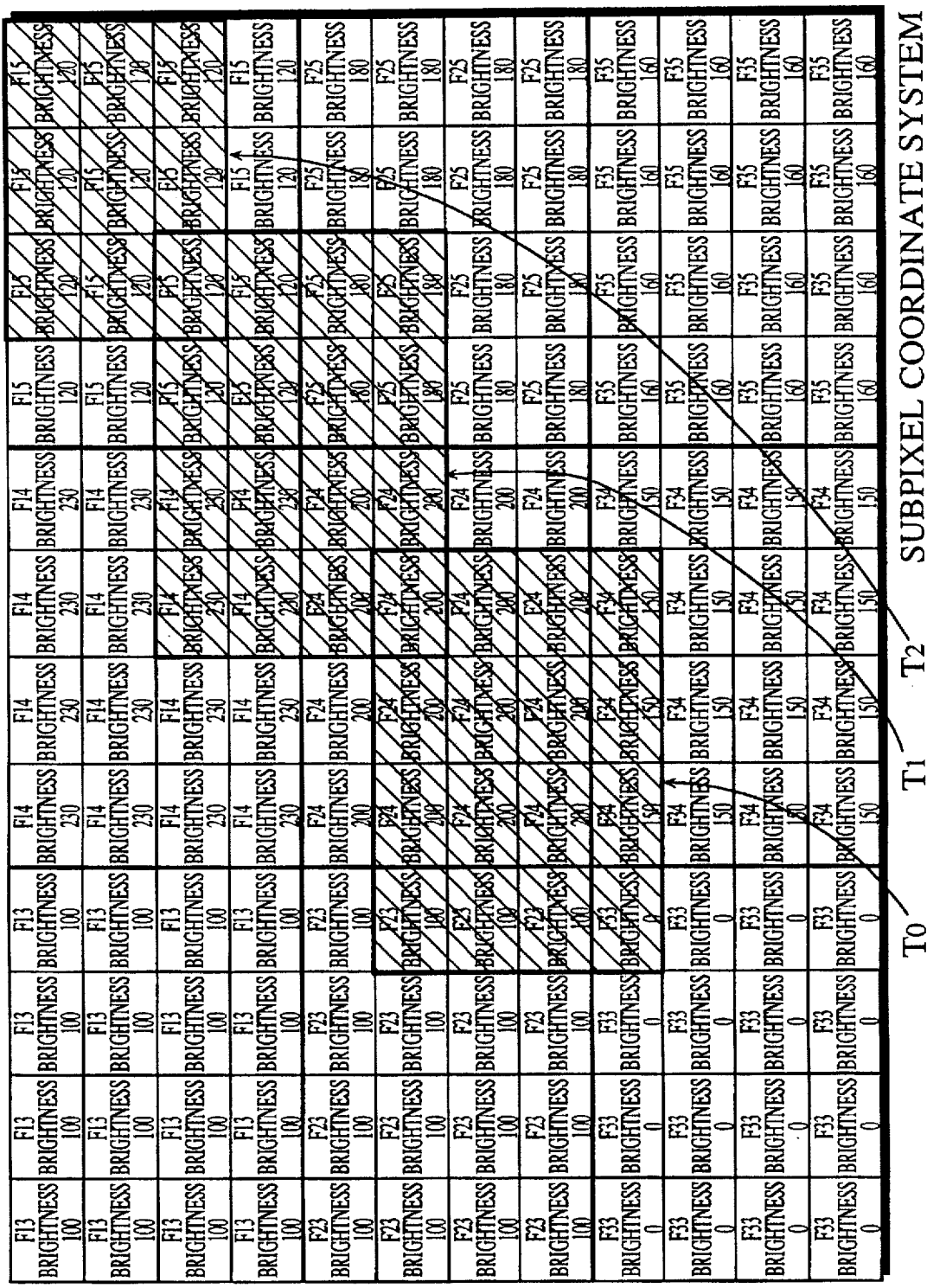

In FIG. 17A, intersections of the striplike areas and the arcs of the search radius have bean marked with white circles, and since each search point is made up of a 4*4 area in the converted subpixel coordinate system, search points T0, T1, and T2 are each made up of 4*4 areas which have been shaded in FIG. 17B.

As can be seen from FIG. 17B, there is an intersection between the point T0 and the 4*4 subpixels corresponding to pixel (x,y)=(4,2), the 4*4 subpixels corresponding to pixel (x,y)=(4,3), and the 4*4 subpixels corresponding to pixel (x,y)=(3,2).

In FIG. 17B, search pixel T0 has an intersection with nine of the subpixels which compose the pixel (x,y)=(4,2), with three of the subpixels which compose the pixel (x,y)=(4,3) with three of the subpixels which compose the pixel (x,y)

=(3,2), and with four of the subpixels which composes the pixel (x,y)=(3,3).

Similarly, search pixel T1 has an intersection with four of the subpixels which compose the pixel (x,y)=(4,2), with four of the subpixels which compose the pixel (x,y)=(4,1), with four of the subpixels which compose the pixel (x,y)=(5,2), and with one of the subpixels which composes the pixel (x,y)=(5,1).

As can be seen in FIG. 17B, all subpixel values of the pixel (x,y)=(4,2) have a monochromatic brightness of 200, all subpixel values of the pixel (x,y)=(4,3) have a monochromatic brightness of 150, and all subpixel values of the pixel (x,y)=(3,2) have a monochromatic brightness of 100.

When, for the present situation, an average value is taken for the shaded search points T0 and T1, the following calculations are performed.

Search point T0

(200*9+100*3+150*3+0*1)/16=159.375

Search point T1

(230*4+200*4+180*4+120*4)/16=182.5

Once average values have been calculated for every search point, an average value of a pixel value for each search line segment filter is calculated. When an average is calculated using, for ease of understanding, only the two points calculated above, the average for the 45° direction is as follows.

(159.375+183.5)/2=171.375

Figure 17C:
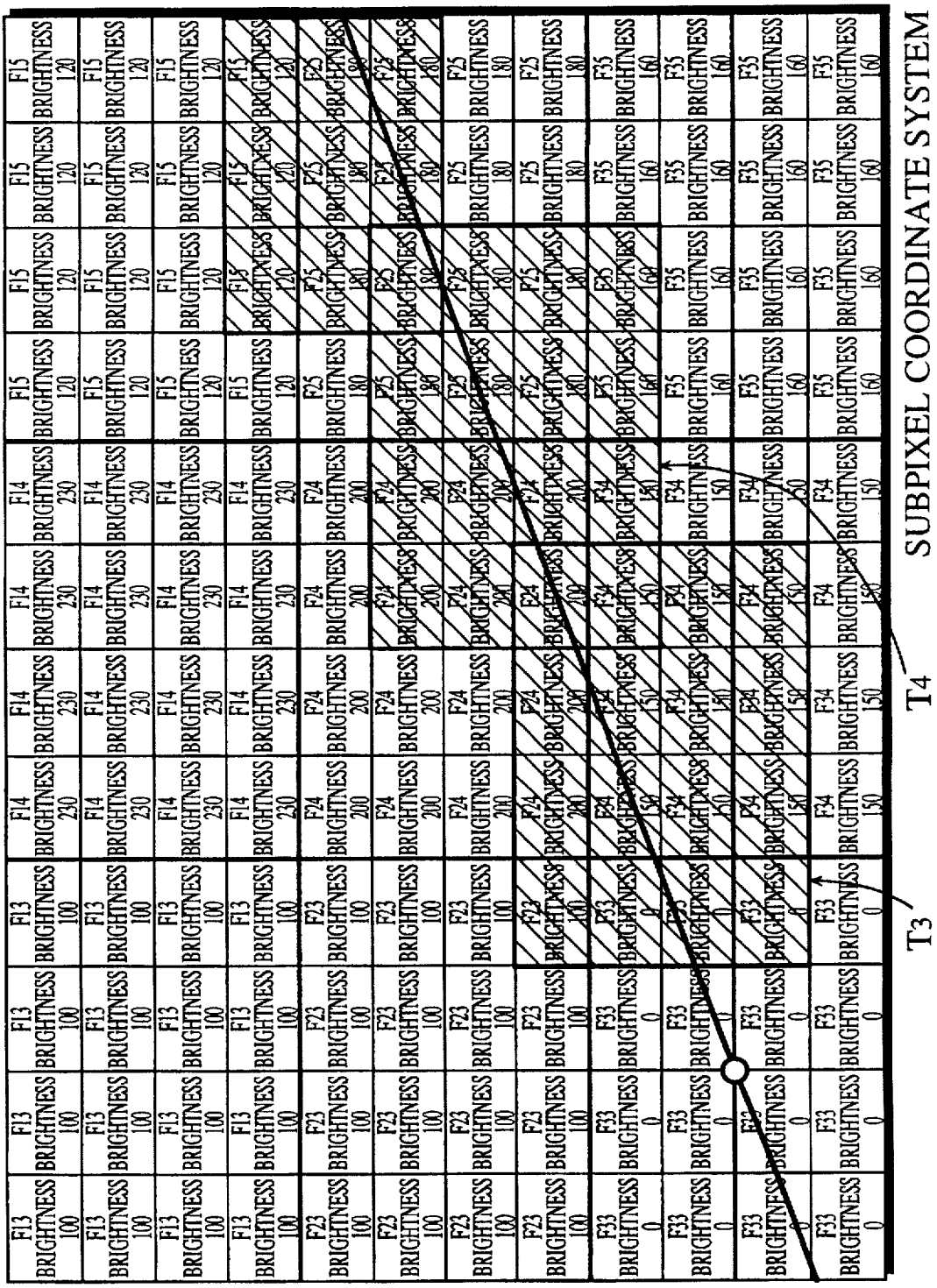

The following is an explanation of when the striplike search region is rotated through 30° in a 12*12 subpixel grid, which is shown along with search points in FIG. 17C.

In FIG. 17C, search pixel T3 has an intersection with three of the subpixels which compose the pixel (x,y)=(4,2), with nine of the subpixels which compose the pixel (x,y)=(4,3), with one of the subpixels which composes the pixel (x,y)=(3,2), and with three of the subpixels which compose the pixel (x,y)=(3,3).

In FIG. 17C, search pixel T4 has an intersection with six of the subpixels which compose the pixel (x,y)=(4,2), with two of the subpixels which compose the pixel (x,y)=(4,3), with two of the subpixels which compose the pixel (x,y)=(5,3), and with six of the subpixels which compose the pixel (x,y)=(5,2).

When, for the present situation, an average value is taken for the shaded search points T3 and T4, the following calculations are performed.

Search point T3

(200*3+0*3+100*1+150*9)/16=126.125

Search point T4

(150*2+200*6+180*6+160*2)/16=181.25

Once the above process has been performed for every search point, the processing for the search line segment filter determined by rotating the striplike region through 30° is complete.

Once average values have been calculated for every search point, an average value of a pixel value for each search line segment filter is calculated. When an average is calculated using, for ease of understanding, only the two points calculated above, the average for the 30° direction is as follows.

(126.125+181.25)/2=154.5875

Figure 17D:
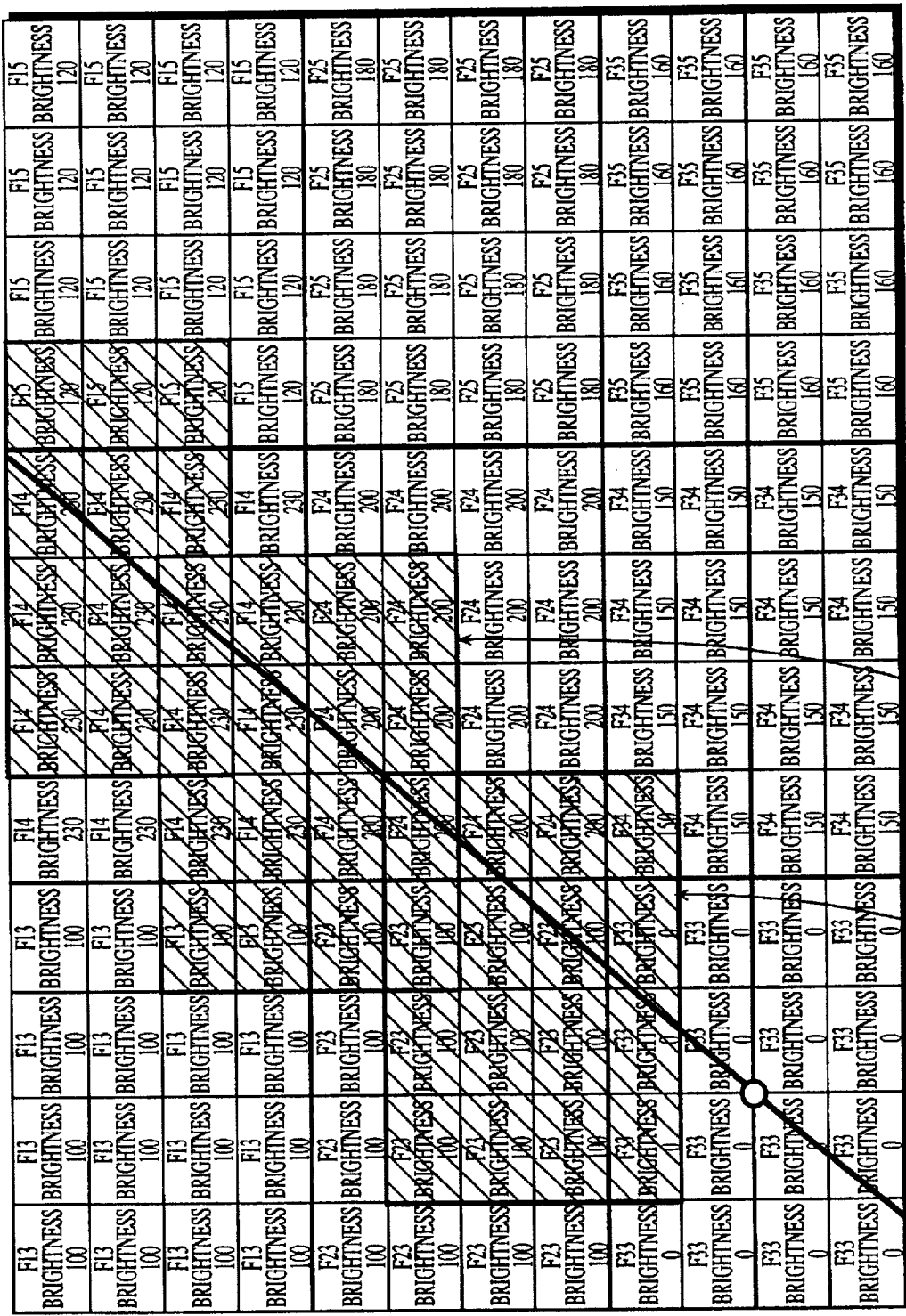

The following is an explanation of when the striplike search region is rotated through 60° in a 12*12 subpixel grid, which is shown along with search points in FIG. 17D.

In FIG. 17D, search pixel T5 has an intersection with three of the subpixels which compose the pixel (x,y)=(4,2), with one of the subpixels which composes the pixel (x,y)=(4,3), with nine of the subpixels which compose the pixel (x,y)=(3,2), and with three of the subpixels which compose the pixel (x,y)=(3,3).

In FIG. 17D, search pixel T6 has an intersection with six of the subpixels which compose the pixel (x,y)=(4,2), with two of the subpixels which compose the pixel (x,y)=(1,3), with two of the subpixels which compose the pixel (x,y)=(3,2), and with six of the subpixels which compose the pixel (x,y)=(4,1).

When, for the present situation, an average value is taken for the shaded search points T5 and T6, the following calculations are performed.

Search point T5

(200*3+0*3+150*1+100*9)/16=103.125

Search point T6

(100*2+200*6+230*6+100*2)/16=186.25

Once average values have been calculated for every search point, an average value of a pixel value for each search line segment filter is calculated. When an average is calculated using, for ease of understanding, only the two points calculated above, the average for the 60° direction is as follows.

(103.125+186.25)/2=144.625

The average values calculated for the three directions above are

. 45° direction=171.375

30° direction=154.6875

60° direction=144.625

From the above results, it can be seen that the 45° direction has the highest average pixel value. By converting original pixels into subpixels and than performing pixel value searches in the subpixel coordinate system as described above, it becomes possible to compare pixel values in directions which are a mere 15° apart.

Figure 18:
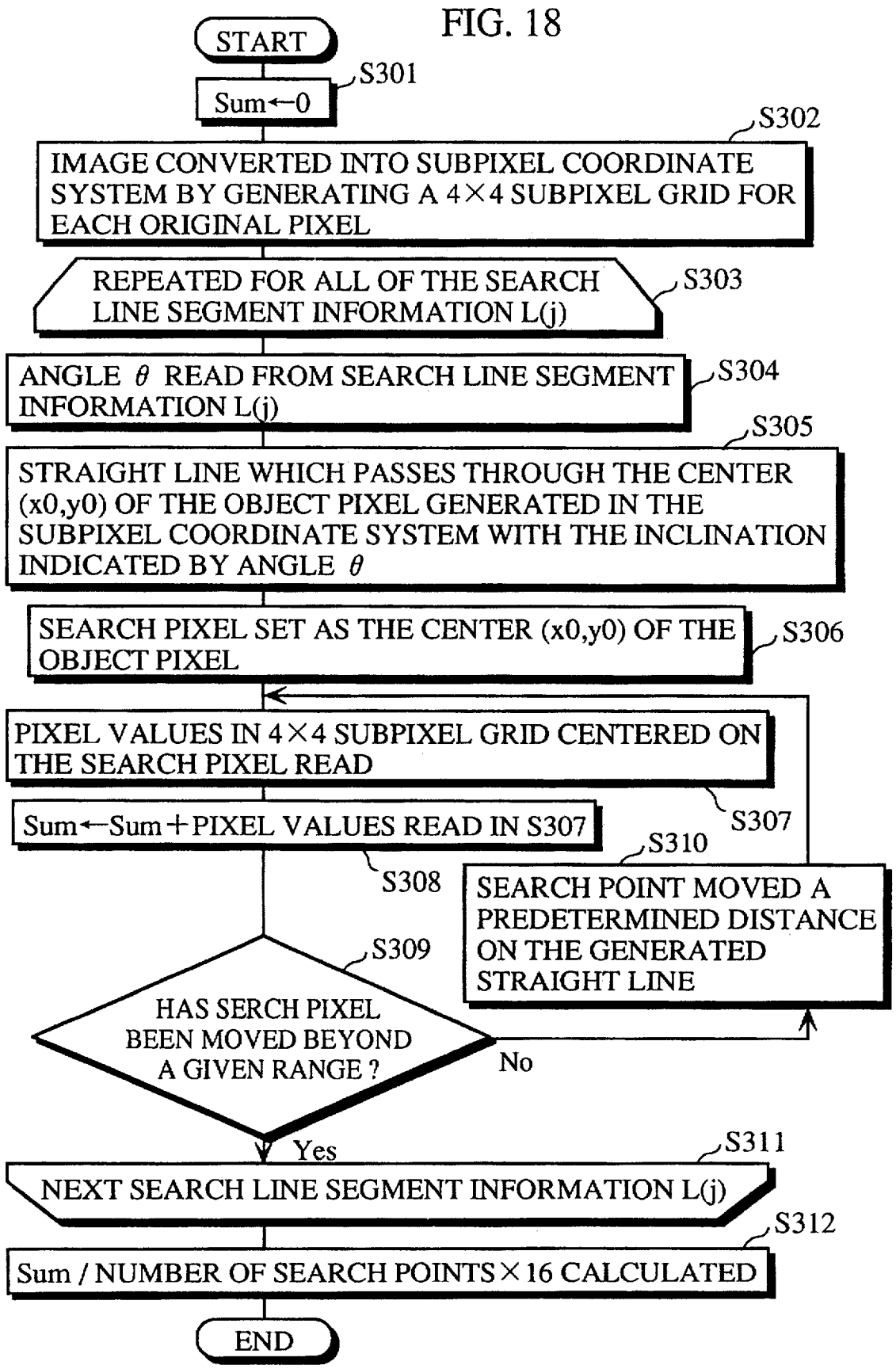
FIG. 18 is a flowchart showing the calculation of an average value in the subpixel coordinate system.

The following is description of the processing for the twelve-way filter by the processor 18, with reference to the flowchart in FIG. 18. In step 301 of FIG. 18, the processor 18 sets the Sum value at zero. In step 302, it generates a 4*4 subpixel grid for each original pixel, and converts the original Image into a subpixel coordinate system. In stop 303, the processor 18 reads the search line filter for the number j from the data modules of the search line filters recorded in the plugin file 17. In step 304, the processor 18 reads the angle θ from the search line filter L(j). In step 305, the processor generates a striplike search area in the subpixel coordinate system which has been rotated by the angle θ about a center object pixel (x0,y0). In step 306, the search point is centered on the object pixel (x0,y0), and in step 307 the processor 18 reads the pixel values for a 4*4 subpixel grid which is centered on this search point. In step 308, the pixel values read in step 308 are added to the Sum value. In step 309, the processor 18 judges whether the position of the search point has advanced as far as a predetermined range. When this is not the case, the search point is advanced by a predetermined distance and the processing returns to step 307.

When the processor 18 has advanced the search point and has performed a return to step 307, the search point is relocated to the advanced position and the pixel values for a 4*4 subpixel grid centered on the new position are read.

The above processing is repeated so that the Sum value becomes the total of the pixel values calculated for pixels where there is an intersection with the search line filter for the number j. The processing in steps 307-310 is repeated many times until the location of the search pixel is at the edge of the search line segment filter. When this point is reached, it is judged in step 309 that the location of the search pixel has exceeded a predetermined range so that the processing then can then proceed to step 311.

In step 311, the number j is incremented by one to designate a next search line segment filter L(j) and the processing returns to step 303. By doing so, the processing in steps 304-310 can be performed for the next search line segment filter.

The processing which follows the calculation of the average values is the same as in the first embodiment, which is to say, the average values for different filters are compared and the object pixel is rewritten using the highest of the average values as its pixel value.

When the processing in step 311 has been completed, the processor calculates the (Sum value/number of search pixels*16) to calculate the average value of the search line segment L(J).

As described above, by converting the image into subpixels, the second embodiment of the present invention is able to shift the search pixel across a number of pixels. The pixel value of an object pixel can then be updated using a range designated by these distributed search pixels, which means that a very precise enhancement of the object pixel can be performed.

Third Embodiment

The third embodiment of the present invention is a technique for enhancing omissions in physical surfaces Here, the expression "physical surfaces" refers to images obtained by stacking a plurality of outline tomograms. The stacking of tomograms by the present system is performed by the probe drive 14 sliding the probe 3 along the construction rails 4 and having the probe 3 generate a plurality of tomograms in the frame memory array 13, with each tomogram being allocated a z-coordinate which expresses an amount moved by the probe 3 along the construction rails 4.

Omissions in physical surfaces appear when missing outlines in separate cross-sectional images are stacked. In order to enhance these omissions in physical surfaces, this third embodiment has a surface nine-way filter recorded in the plugin file 17.

The surface nine-way filter is a filter which sets an object pixel as a missing part of a physical surface, which specifies the form of the surface in three-dimensional space, and which enhances a pixel value of an object pixel using an average value of the pixel values of the surface of the specified form.

The specifying of a surface supposes that while a plurality of surfaces pass through the object pixel, the inclination of the normal line of each surface is different. The average values of the pixel values of pixels which compose these surfaces are calculated and the surface with the highest average value is selected.

FIGS. 19A–19I show nine surfaces which are inside a cube made up of 5*5*5 pixels which has the object pixel at its center (X-coordinate=3, Y-coordinate-3, Z-coordinate-3).

Figure 19A:
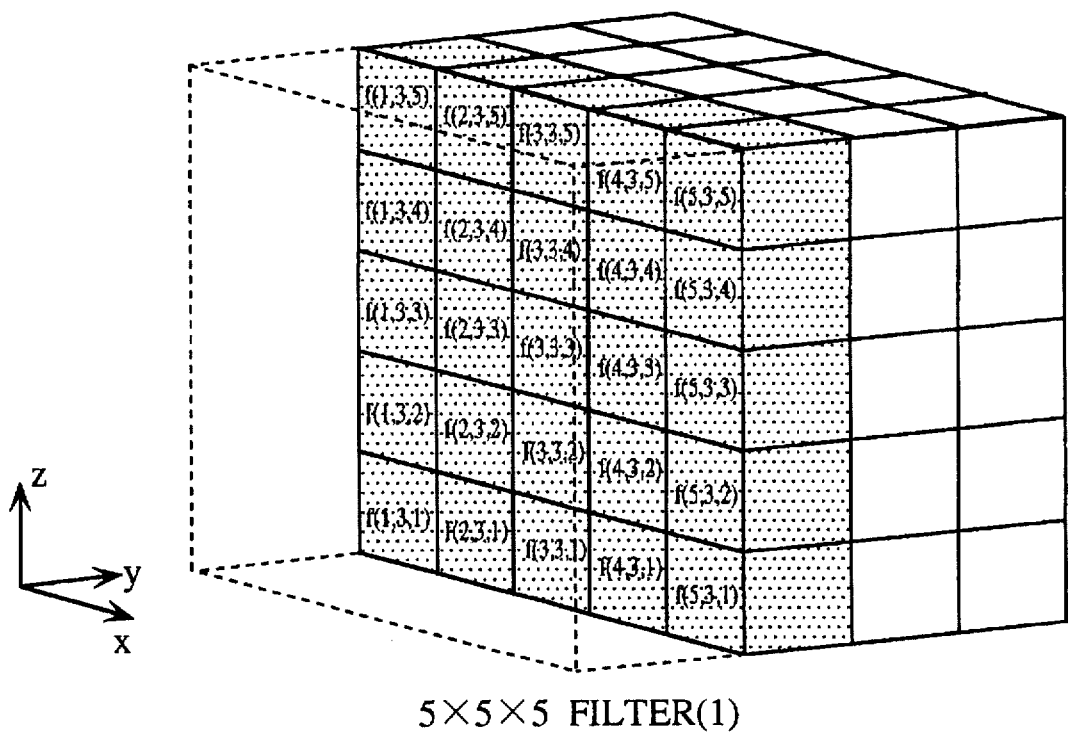
FIGS. 19A-19I show nine arbitrary surfaces in a 5*5*5 subpixel coordinate system which has the object pixel at its center (x=3, y=3, z=3)
Figure 19B:
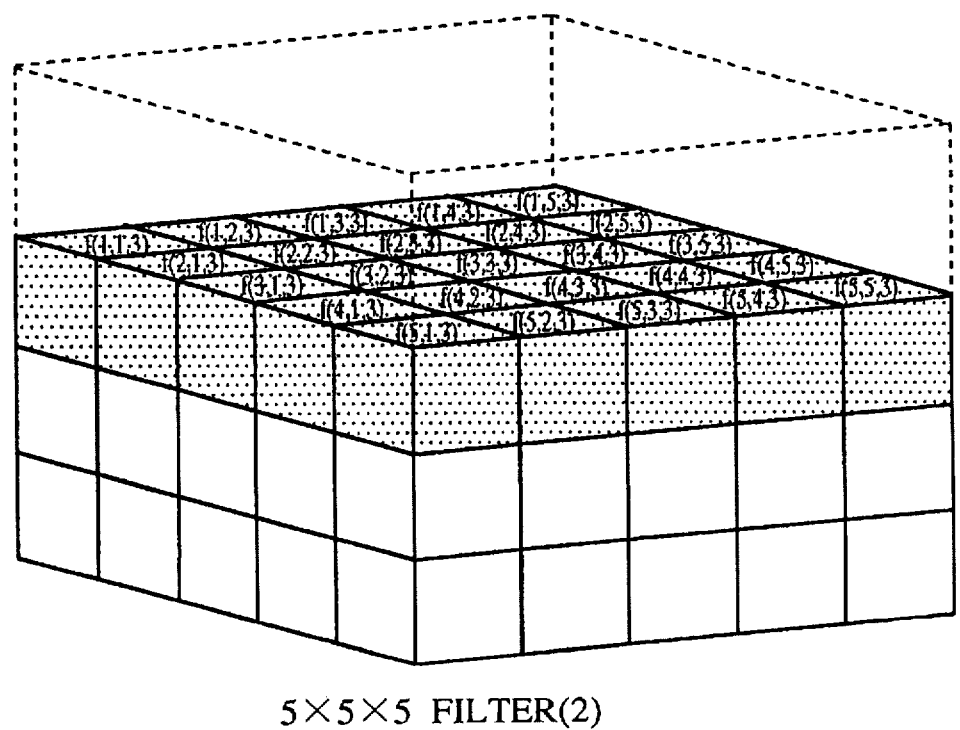
Figure 19C:
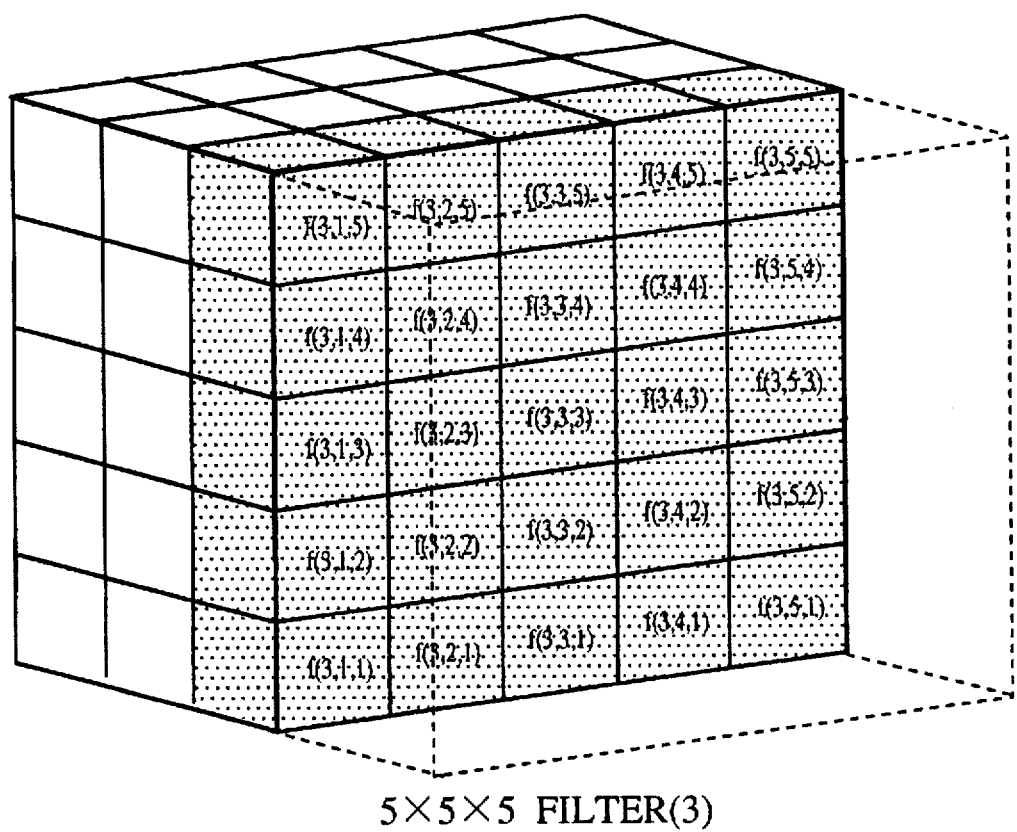

FIG. 19A shows a surface which passes through the object pixel and whose normal vector is (0,1,0). FIG. 19B shows a surface which passes through the object pixel and whose normal vector is (0,0,1). FIG. 19C shows a surface which passes through the object pixel and whose normal vector is (1,0,0).

Figure 19D:
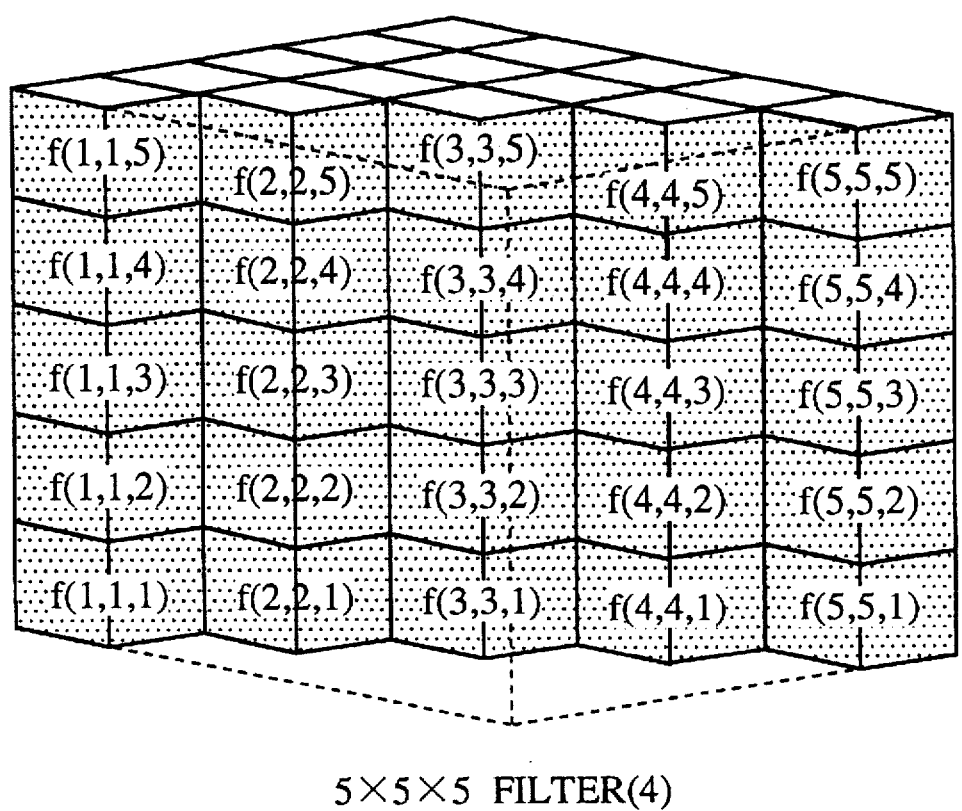
Figure 19E:
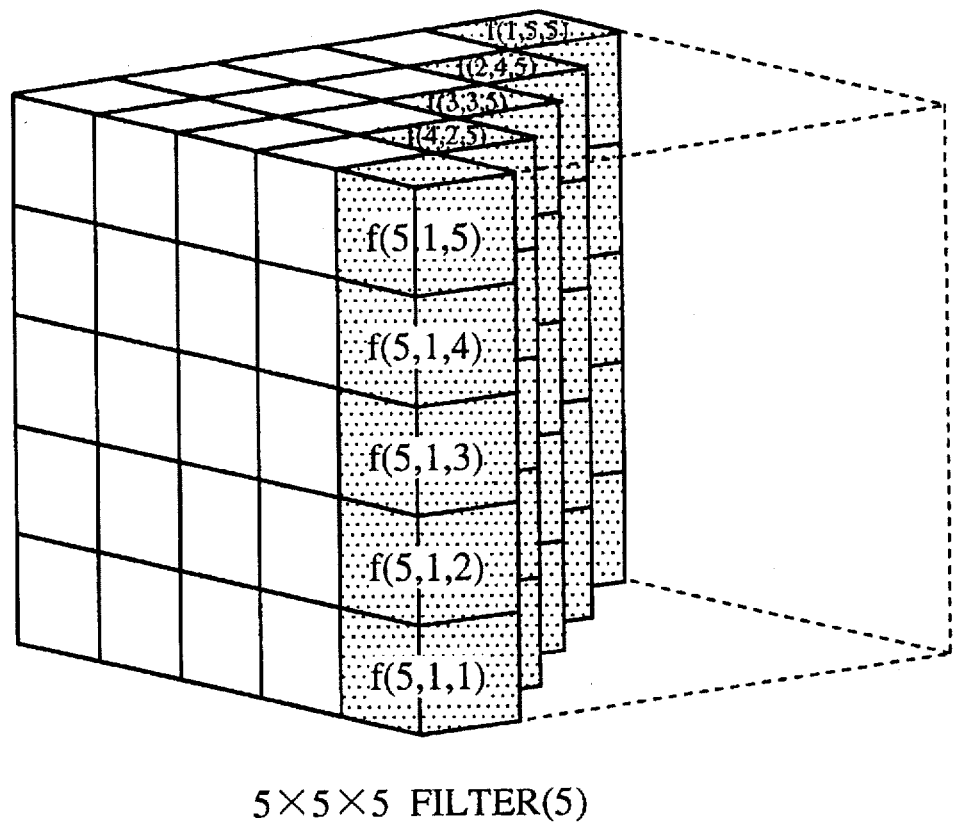
Figure 19F:
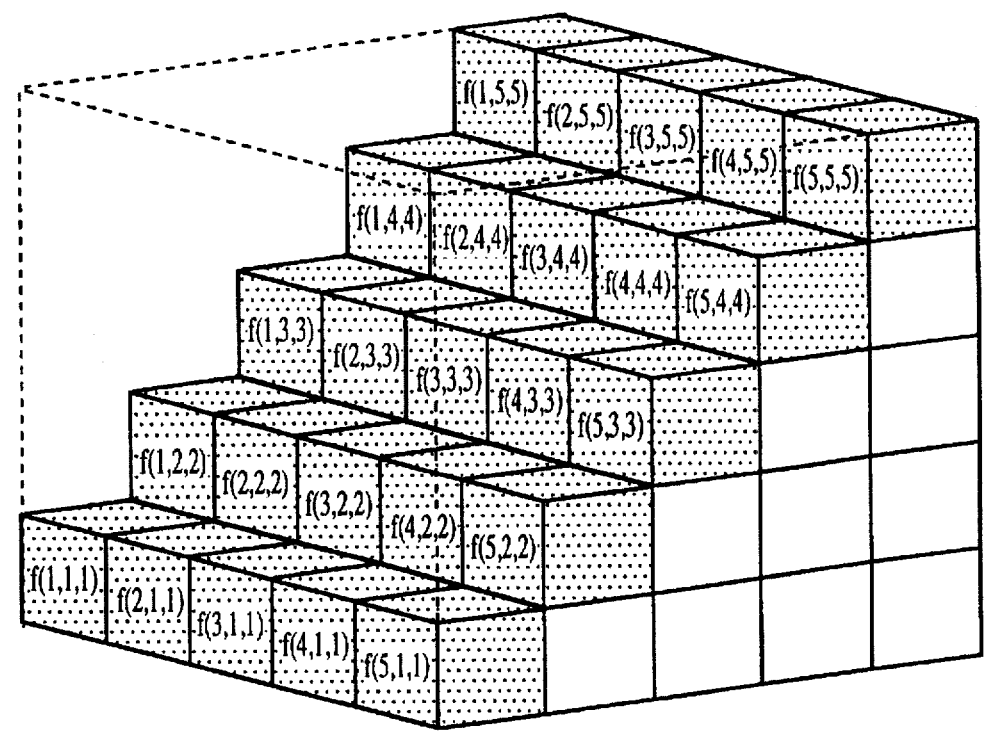

FIG. 19D shows a surface which passes through the object pixel and whose normal vector is (1,-1,0). FIG. 19E Shows a surface which passes through the object pixel and whose normal vector is (1,1,0). FIG. 19F shows a surface which passes through the object pixel and whose normal vector is (0,-1,1).

Figure 19G:
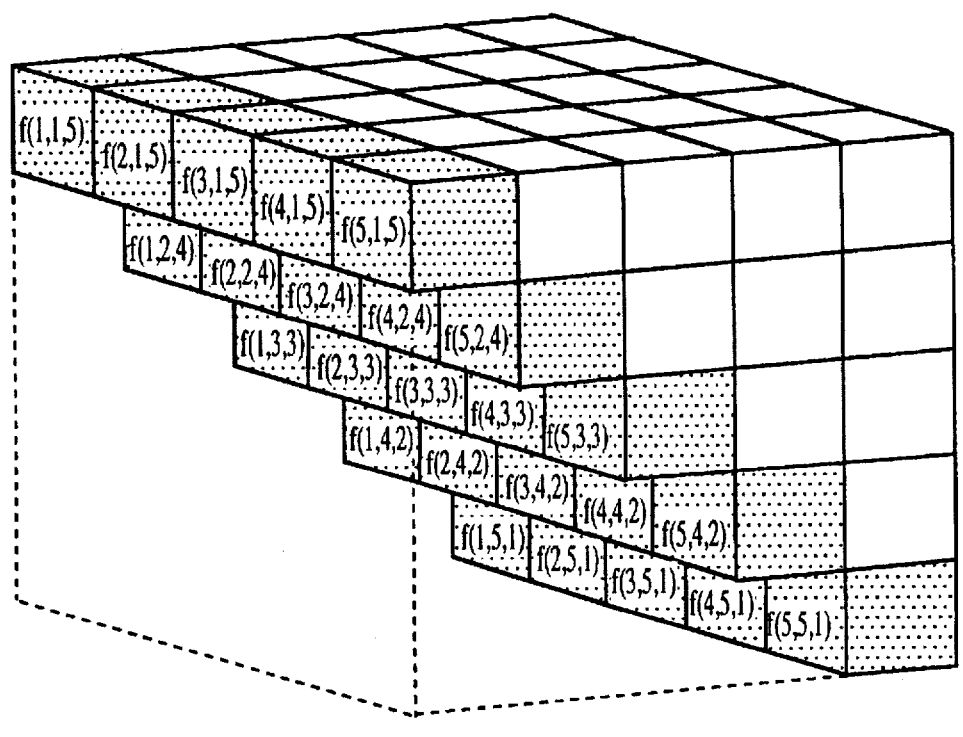
Figure 19H:
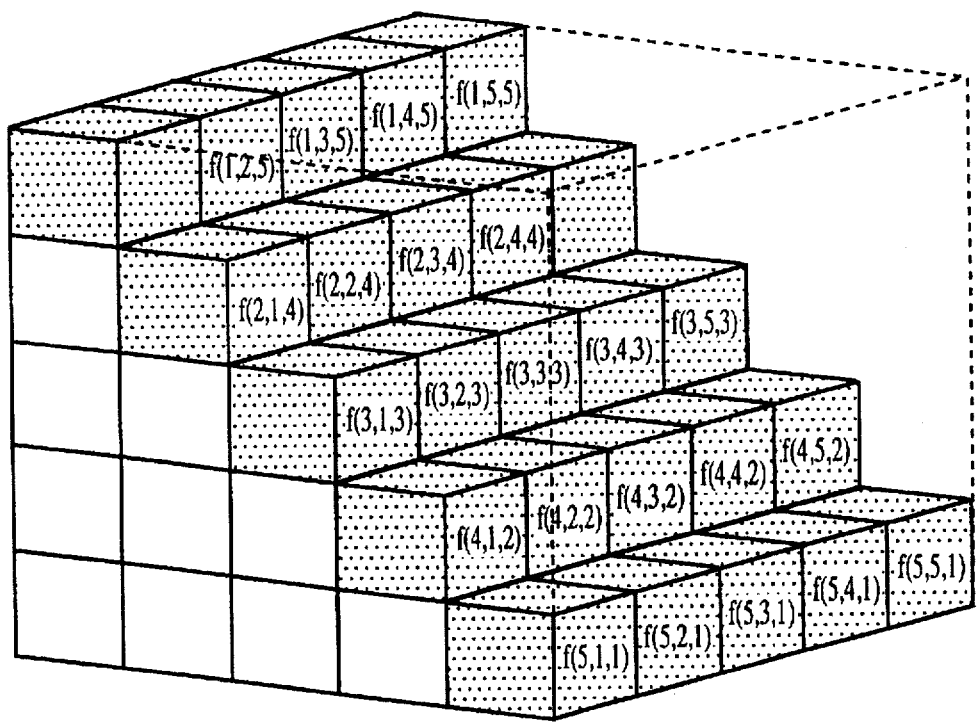
Figure 19I:
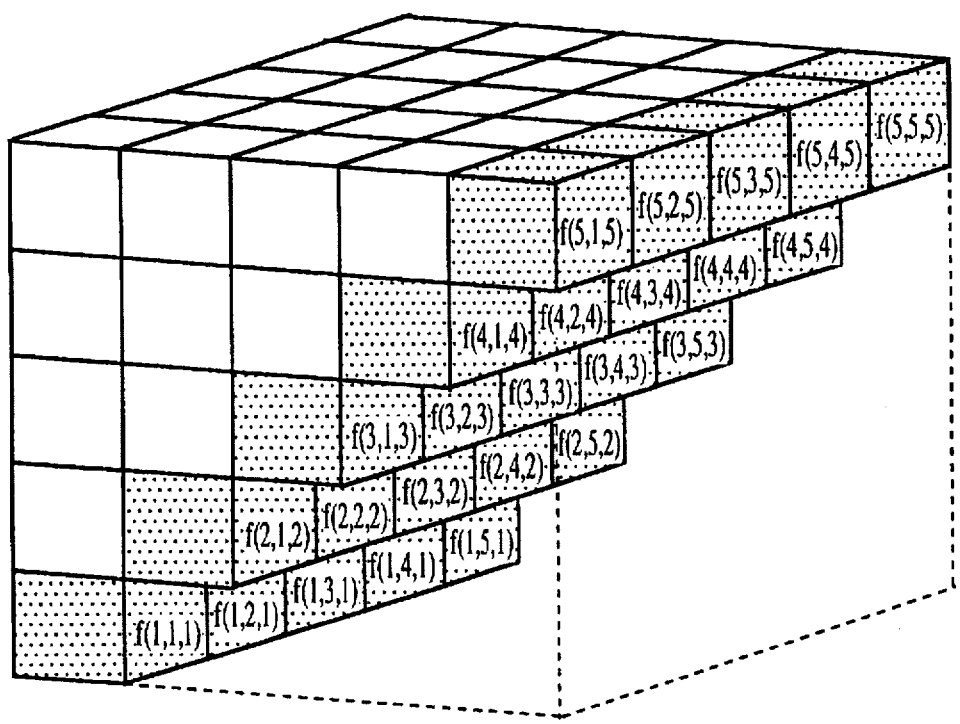

FIG. 19G shows a surface which passes through the object pixel and whose normal vector is (0,-1,-1). FIG. 19H shows a surface which passes through the object pixel and whose normal vector is (1,0,1). FIG. 19I shows a surface which passes through the object pixel and whose normal vector is (1,0,-1).

The following is an explanation of the data construction used to express the nine-way surface filter. The nine-way surface filter is made up of a plurality of acts of search points, each of which indicates one of surfaces shown in FIGS. 19A through 19I This data construction is shown in FIG. 20.

As shown in FIG. 20, a search surface filter is written as an array of fixed search points, with the data construction also including a space to record an average value calculated for each of the search surface filters. These search surface filters are numbered 1, 2, 3 . . . for identification purposes.

Each search point in a search point array is written in "f(m,n,l)" format. As before with the search line segment filters, the subscript "m" in the search point "f(m,n,l)" indicates a pixel position "m–3" from the object pixel in the Y-axis, the subscript "n" in the search point "f(m,n,l)" indicates a pixel position "n–3" from the object pixel in the X-axis, and the subscript "l" in the search point "f(m,n,l)" indicates a pixel position "l–3" from the object pixel in the Z-axis. This subtraction of "3" from each level, as shown in FIG. 19A, is performed to position (x,y,z)=(3,3,3) in the center of the 5*5*5 grid used by the search surface filter. For the above arrangement, when the search point is "f(3,4,3)", a pixel which is displaced one space past the center in the X-axis is designated, while when the search point is "f(4,5,4)", a pixel which is displaced two spaces past the center in the X-axis, one space post the center in the Y-axis, and one space past the center in the Z-axis is designated.

Average values of the pixels located on a surface are separately calculated for the nine surfaces shown in FIGS. 19A–19I, and it is judged whether all of these average values are equal to or below a threshold value. When every average value is equal to or below the threshold value, there is a high possibility that the pixel contains speckle noise, while when any of the average values is above the threshold value, the average values are compared for different surfaces and the surface with the highest average value is selected.

The surface specified by the process described above can be considered as having a form which most closely approximates to the surface which includes the object pixel. If the pixel value of this object pixel is adjusted to the average value of the specified surface, the object pixel can be given a pixel value which is in keeping with the pixels surrounding it on the surface of the original image.

Figure 21:
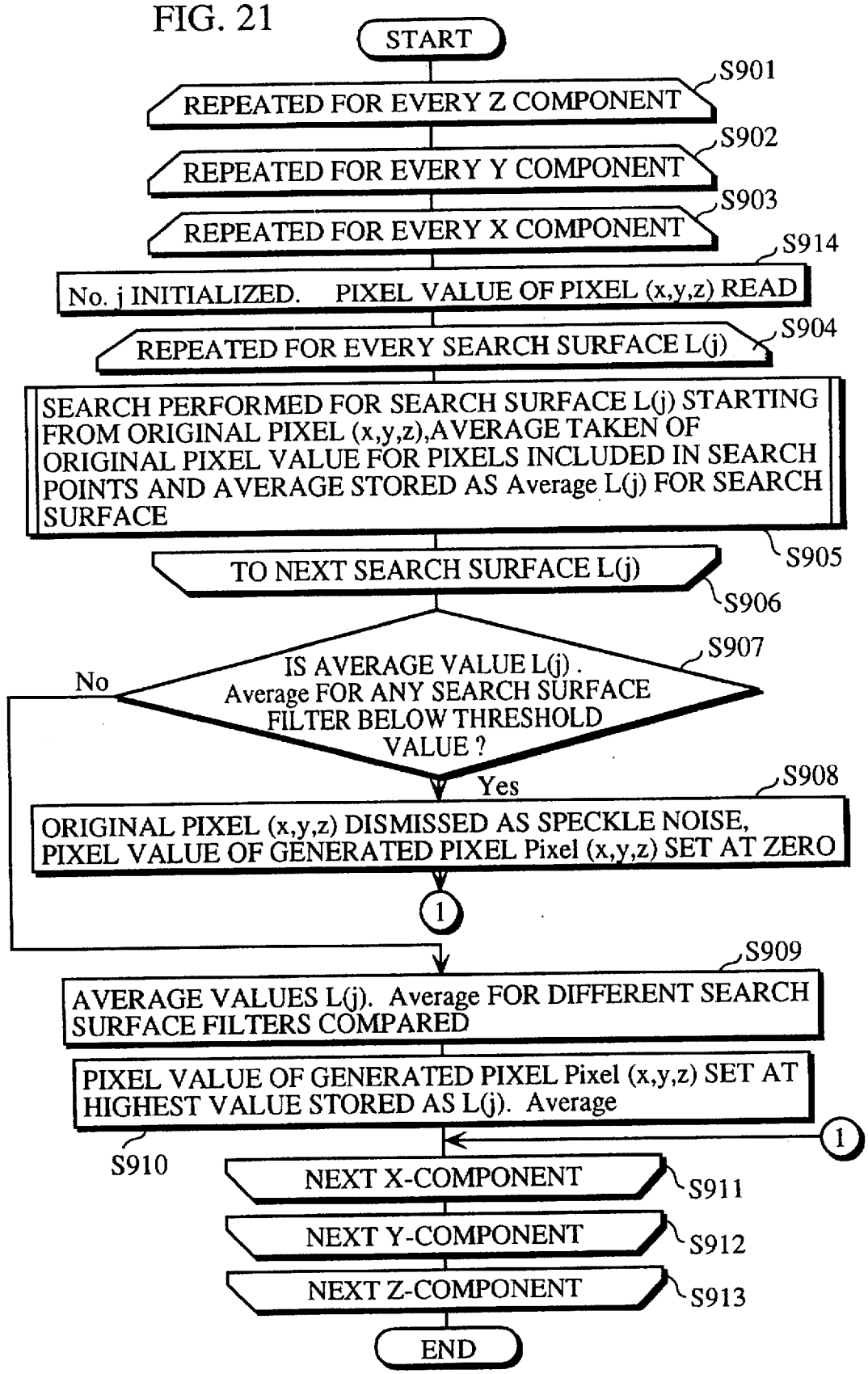
FIG. 21 is a flowchart for the processing of a search surface filter.

The procedure executed by processor 18 when performing image enhancement using a surface nine-way filter is shown by the flowchart in FIG. 21.

As can be seen from FIG. 21. a loop process is performed between steps 903 and 911, with the X coordinate being incremented in each iteration. Another loop process is performed between steps 902 and 912, with the Y coordinate being incremented by one in each iteration, and another loop process is performed between in steps 901 and 913, with the Z coordinate being incremented by one in each iteration. In step 914, the processor 18 resets the variable j to "1" and reads the pixel value of Pixel(x,y,z) by accessing the frame memory array 13, before performing the loop process of steps 904-906.

In step 904, the search surface filter L(j) indicated by the number j is read out and in step 905, the processor 18 performs a search using the search surface filter L(j), starting with the original pixel Pixel(x,y,z). The processor finds the average value of the pixel values of all the pixels included in the search points and stores the calculated average value as L(j).Average for the appropriate search surface filter. In step 906, the variable j is incremented by one to indicate the next search surface filter L(j) and the processing returns to step 904.

Figure 22:
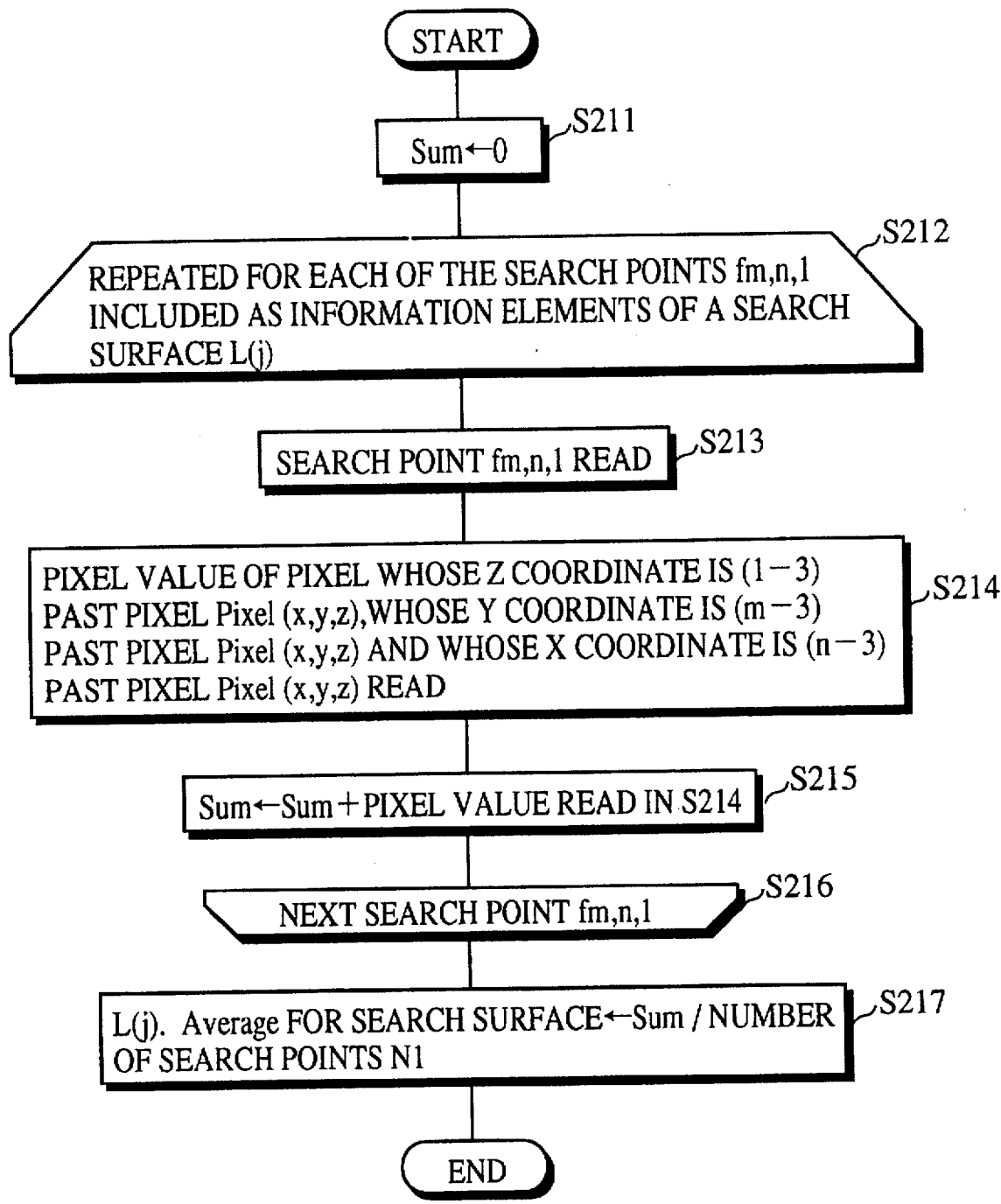
FIG. 22 shows the details of the processing in step 905 of FIG. 21.

A flowchart for the more specific subroutines which compose the procedure in step 105 is shown in FIG. 22. This will be used to explain the details of the processing in step 905 by the processor 18.

In step 211 of FIG. 22, processor 18 resets the Sum value to zero. In step 212 and step 216, processor 18 controls the execution of the loop made up of steps 213-215 for each of the search points "f(m,n,l)" which are included in the search surface filter L(j). In step 213, a search point f(m,n,l) is read and, in step 214, a pixel value of a pixel which is (l-3) past pixel (x,y,z) in the Z-axis, (m-3) past pixel (x,y,z) in the Y-axis, and (n-3) past pixel (x,y,z) in the X-axis is read. After the pixel value has been read, it is added to the Sum value in step 215. This loop is repeated until it has been performed for all of the search points, at which point the processor 18 divides the Sum value by the Number of search points N1 and stores the result as the average value L(j) .Average for that search surface filter.

Once the processing in steps 211-217 in FIG. 22 has been completed, the processing advances to step 906 in the flowchart in FIG. 21 where it in determined whether there are any search surface filters which are left unsearched. When it is determined that such a filter is remaining, the processing advances to step 904, or otherwise advances to step 907 when there is no unsearched filter remaining.

In step 907, processor 1B determines whether the average values L(J).Average of every search surface filter L(j) is equal to or below a threshold.

If it is determined in step 907 that every average pixel value is equal to or below the threshold value, the original pixel (x,y,z) is dismissed in step 908 as speckle noise and the pixel value of the generated pixel Pixel(m,y,z) is set at zero.

In stop 909, the processor 18 compares average values L(j) which are determined in step 907 to be above the threshold value with each other.

Once the search surface filter with the highest average value has been determined, the processor 18 sets the pixel value Pixel(x,y,z) of the generated pixel using this highest average value, thereby completing the processing for one pixel.

Curved Surface Eight-Way Filter

A curved surface eight-way filter is used to specify the kind of missing surface to which an object pixel is a missing part, and is a filter which performs enhancement of a pixel value of an object pixel using an average value for a curved surface of a corresponding form.

This specification of a curved filter is performed using eight kinds of curved surfaces which each pass through the object pixel and which each have a same degree of curvature, but which have normals at different inclinations. Here, average values are calculated for each surface using the pixel values of all of the pixels which compose the curved surface, with the curved surface having the highest average value then being selected.

Figure 23A:
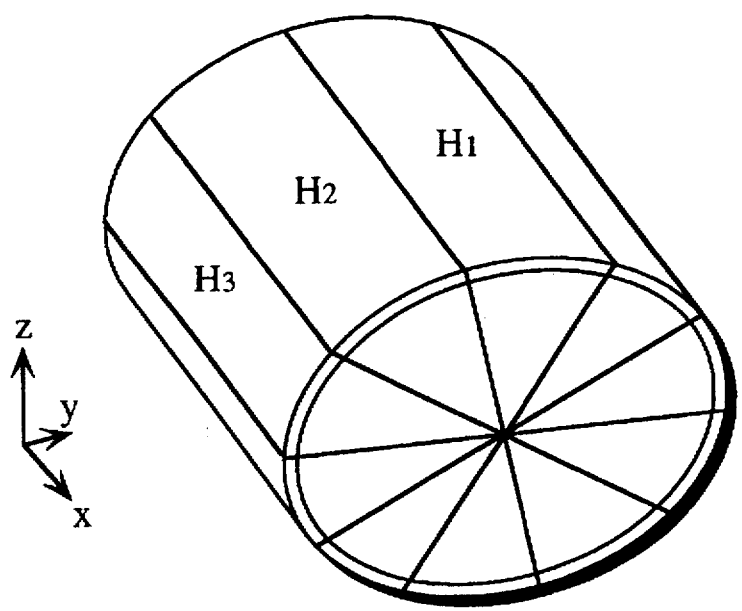
FIGS. 23A to 23C show virtual curved surfaces as the sides of a cylindrical object.
Figure 23B:
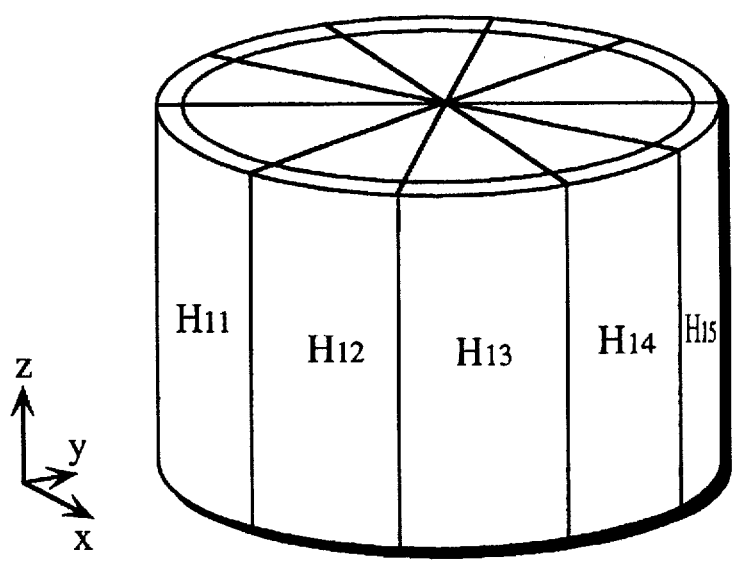
Figure 23C:
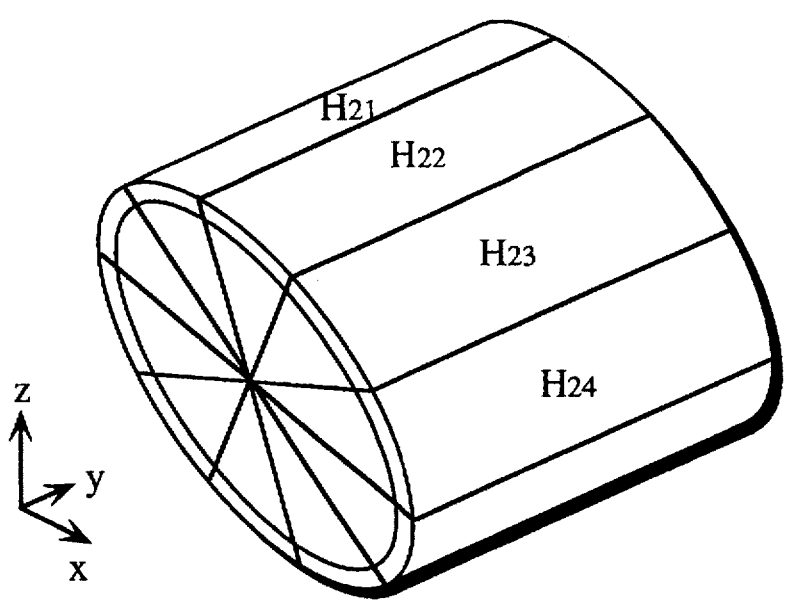

The example of the curved surface search filters used in the present explanation are shown in FIGS. 23A, 23B, and 23C. FIGS. 23A-23C show curved surface search filters which have been conceived on the surface of a cylinder In FIG. 23A, the curved surface search filters H1, H2, and H3 nave been shown with the cylinder aligned with the x-axis In FIG. 23B, the curved surface search filters H11, H12, and H13 have been shown with the cylinder aligned with the z-axis. In FIG. 23C, the curved surface search filters H21, H22, and H23 have been shown with the cylinder aligned with the z-axis.

Figure 24A:
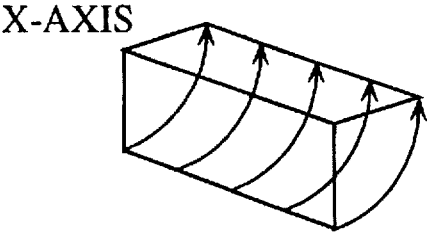
FIGS. 24A to 24C show one surface out of the virtual curved surfaces.
Figure 25A:
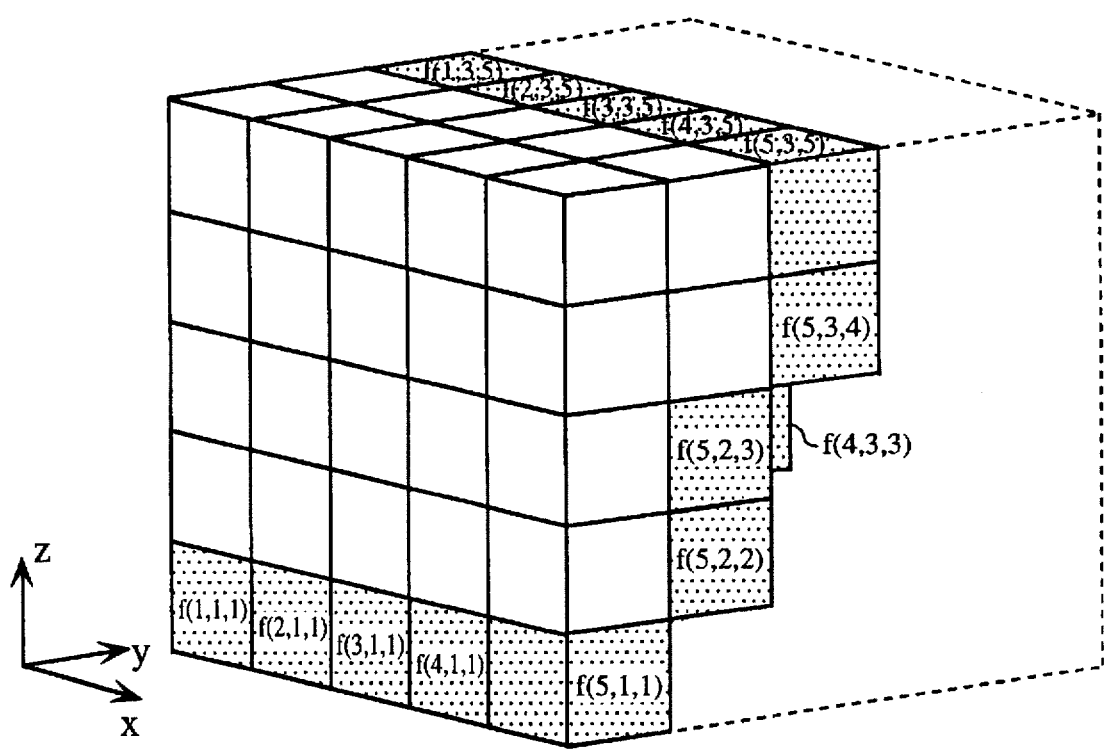
FIG. 25A to 25C show the search points expressed by coordinates which are relative to the object pixel.

FIG. 24A shows one surface out of the curved surface search filters shown in FIG. 23A, with FIG. 25A showing the search pixels expressed as an array of relative coordinates of the curved surface search filter and the object pixel. Here, FIG. 25A shows the curvature of the curved surface search filter in a space composed of 5*5*5 subpixels which has the center of the object pixel as its center $(x,y,z)=(3,3,3)$, with this curvature being expressed using an array of relative coordinates, such as f(5,1,1), f(5,2,2), f(5,2,3), f(5,3,4), f(5,3,5).

Figure 24B:
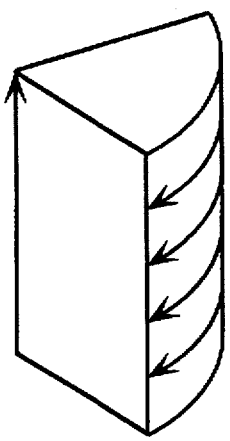
Figure 25B:
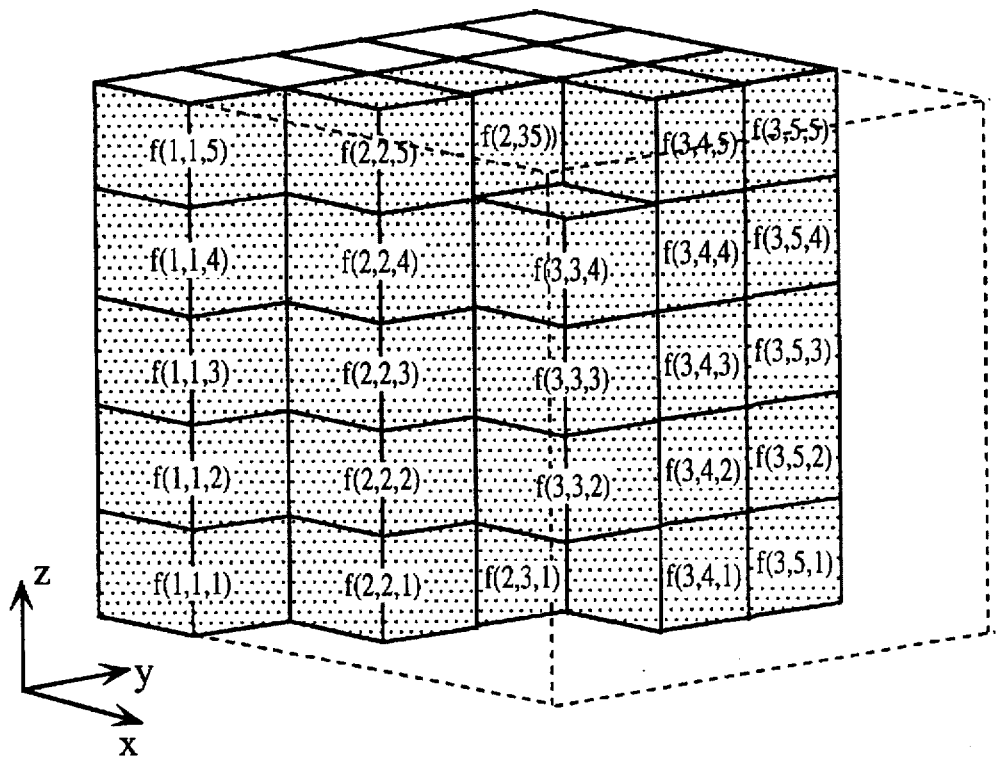

FIG. 24B shows one surface out of the curved surface search filters shown in FIG. 23B, with FIG. 25B showing the search pixels which express the curved surface search filter. Here, FIG. 25B shows the curvature of the curved surface search filter in a space composed of 5*5*5 subpixels which has the center of the object pixel as its center $(x,y,z)=(3,3,3)$, with this curvature being expressed using an array of relative coordinates, such as f(1,1,5), f(2,2,5), f(2,3,5), f(3,4 5), f(3,5,5).

Figure 24C:
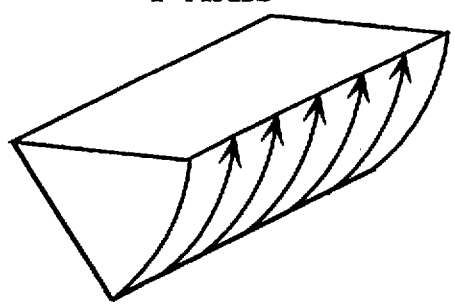
Figure 25C:
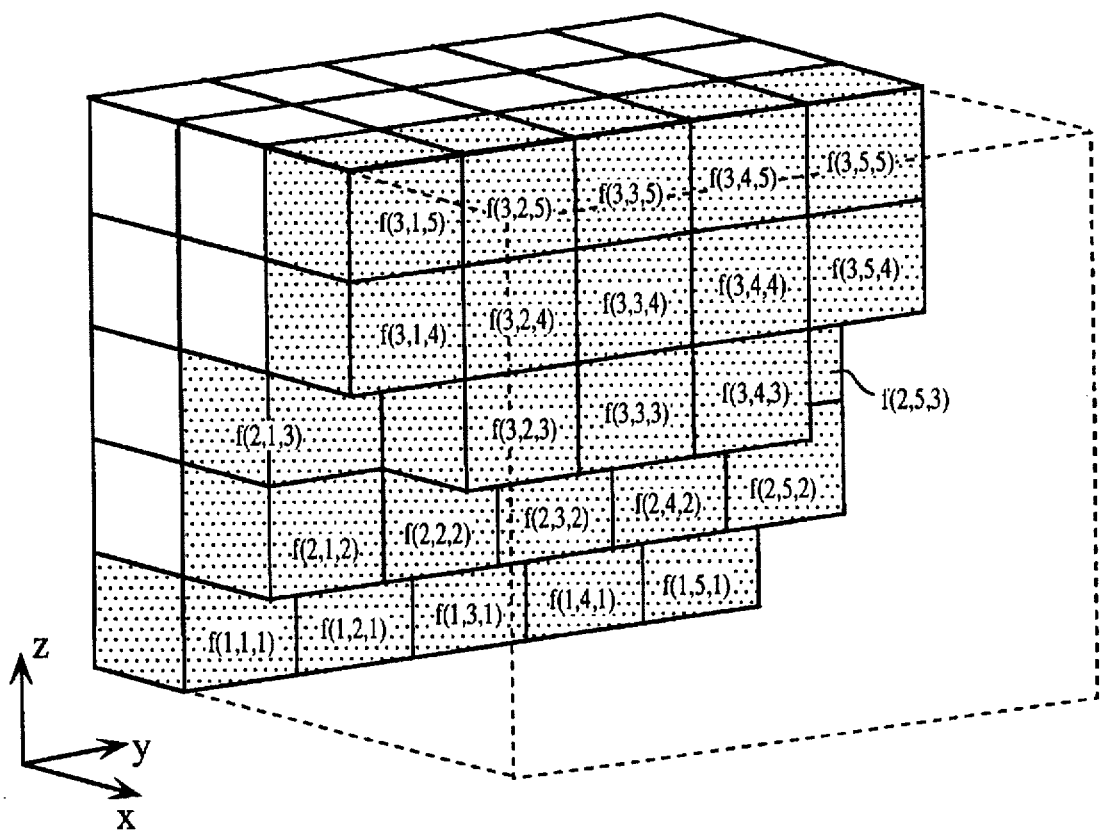

FIG. 24C shows one surface out of the curved surface search filters shown in FIG. 23C, with FIG. 25C showing the search pixels which express the curved surface search filter. Here, FIG 25C shows the curvature of the curved surface search filter in a space composed of 5*5*5 subpixels which has the center of the object pixel as its center $(x,y,z)=(3,3,3)$, with this curvature being expressed using an array of relative coordinates, such as f(3,1,5), f(3,2,5), f(3,3,5), f(3,4,5), f(3,5,5).

An average value for the pixel values distributed on each of the eight curved surfaces of differing forms is calculated and processor 18 determines whether all of these calculated average values is equal to or below a threshold value. Here, there is a high possibility that values determined as being equal to or below the threshold value are speckle noise, while values which above the threshold are compared and the surface with the highest average value is specified out of the eight possible curved surfaces.

It can be assumed that the curved surface specified as described above is the best approximation to the curved surface which includes the object pixel. By amending the pixel value of the object pixel using the average value of the specified curved surface, the generated pixel can be given a pixel value which is in accordance with the surrounding pixels on a curved surface.

By means of the present embodiment, a variety of candidates can be used for a surface or curved surface on which the object pixel is located and the pixel value of the object pixel using the average value of a specified surface or curved surface. By doing so, the generated pixel can be given a pixel value which is in accordance with the surrounding pixels on a surface or curved surface.

Fourth Embodiment

The fourth embodiment uses a method called "tomogram compensation" and relates to a technique for correcting large missing areas (holes) in the surfaces of a threedimensional image. These holes occur in tomograms when, during measurement by the probe 3, there is poor reflection of ultrasound. "Tomogram compensation" refers to the enhancement of cross-sectional tomograms which make up a three-dimensional image, which as shown in FIG. 26 are composed of cross-sectional images in an X-Z coordinate system which have different Y coordinates, cross-sectional images in an X-Y coordinate system which have different Z coordinates, and cross-sectional images in an Y-Z coordinate system which have different X coordinates.

Figure 27A:
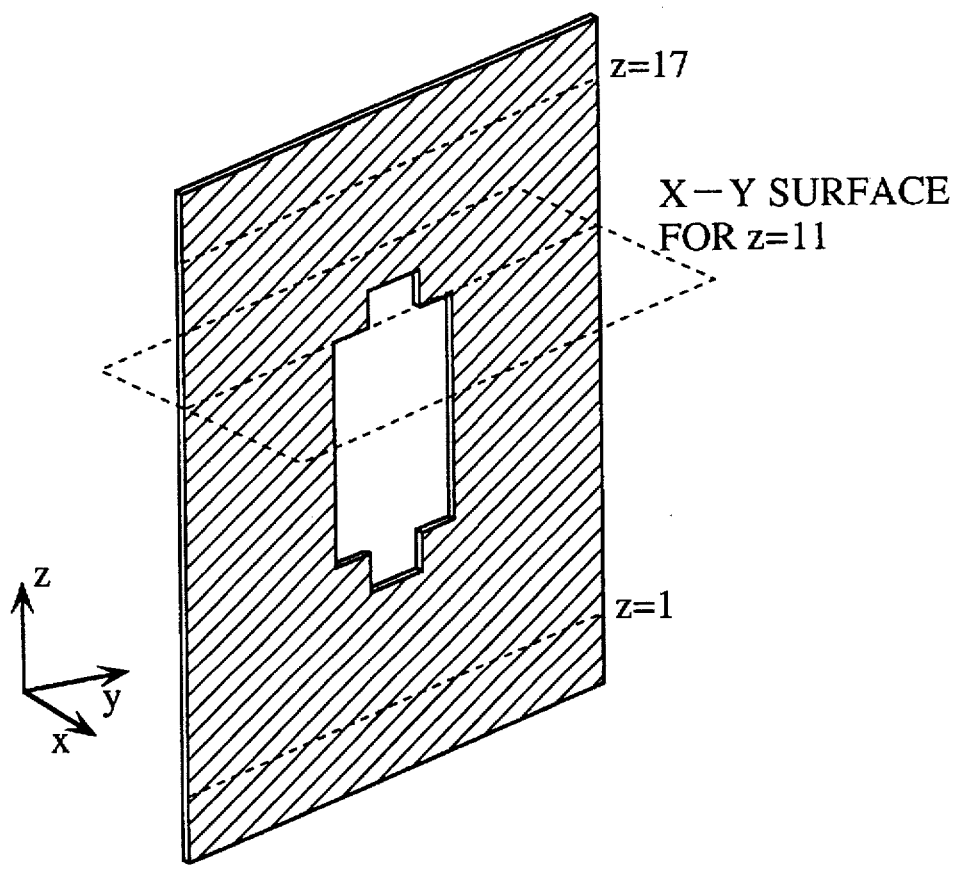
FIGS. 27A to 27C show X-Y planes, X-Y planes and Y-Z planes which are generated at various angles in an X-Y-Z coordinate system.
Figure 27B:
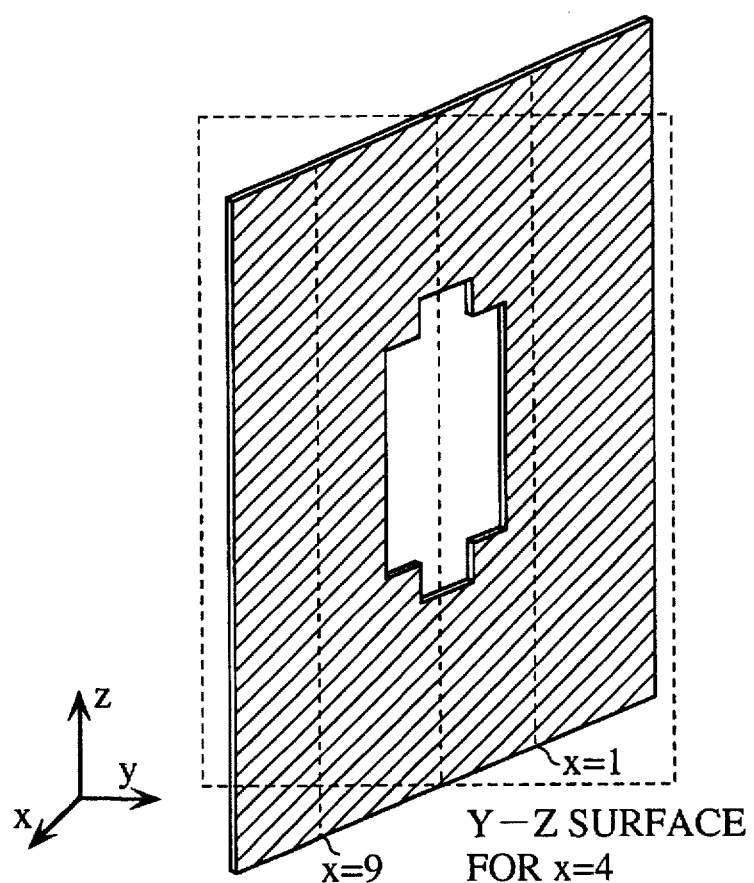
Figure 27C:
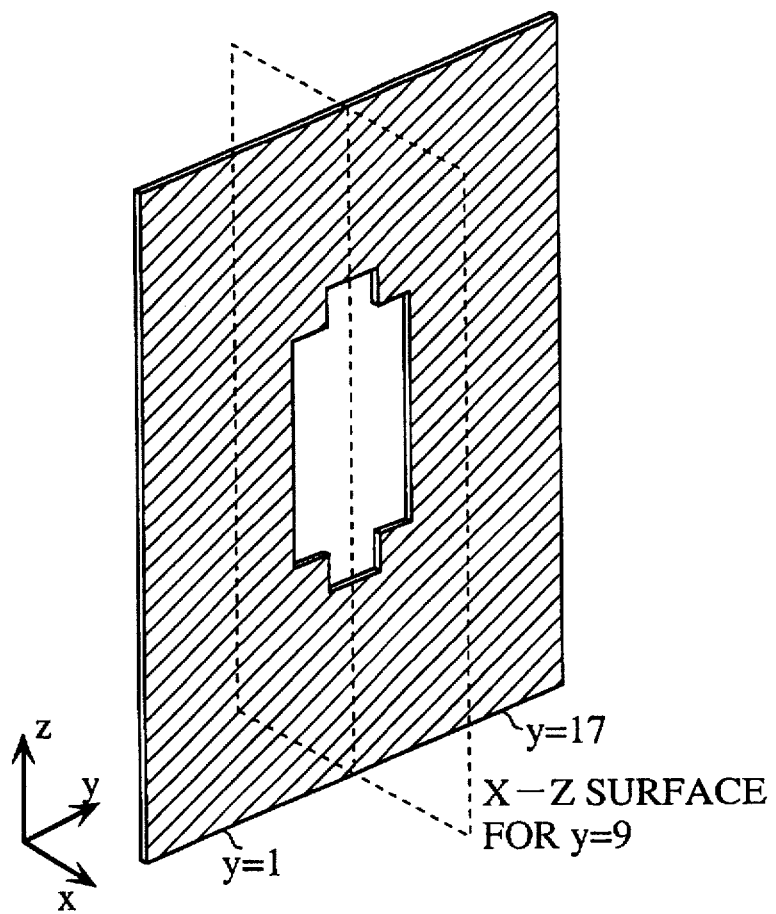

As shown in FIG. 27A–27C, X-Y surfaces, X-Z surfaces, and Y-Z surfaces are arranged during enhancement at certain angles to the three axes in the X-Y-Z coordinate system. Cross-sectional images of either straight lines or curved lines are then obtained on the X-Y, X-Z, and Y-2 cross-sections obtained as above.

If there are differences in coordinates, a cross-sectional image of a straight line whose Y-coordinate is moved little by little is obtained in the X-Y, X-Z, and Y-Z cross-sections shown in FIGS. 26A–28C.

Figure 26:
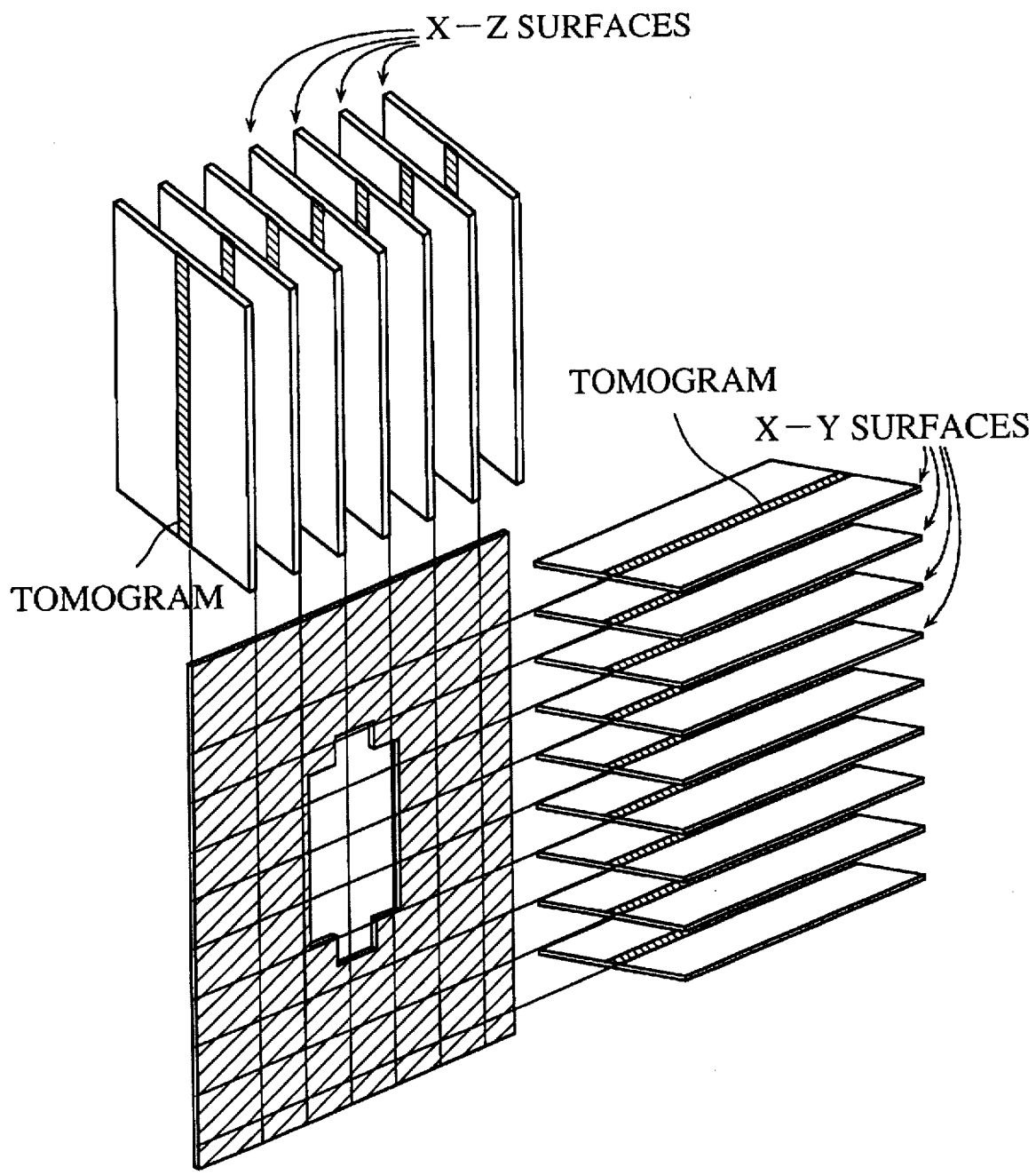
FIG. 26 shows a tomogram of a three-dimensional object which is composed of a plurality of cross-sections in X-Z coordinate system with different Y coordinates, a plurality of cross-sections in X-Y coordinate system with different Z coordinates, and a plurality of cross-sections in Y-Z coordinate system with different X coordinates.
Figure 28A:
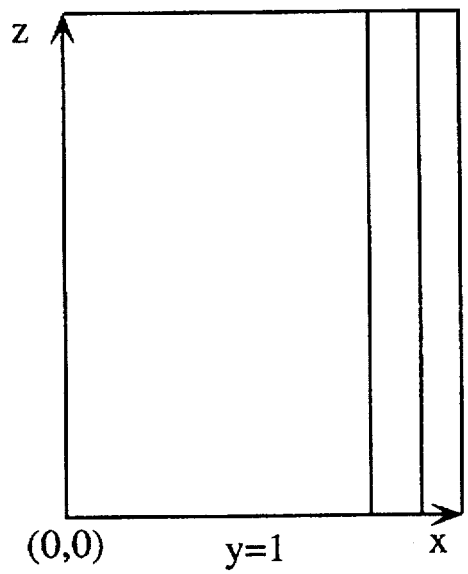
FIGS. 28A to 28I show linear tomograms in planes with different coordinates.
Figure 28B:
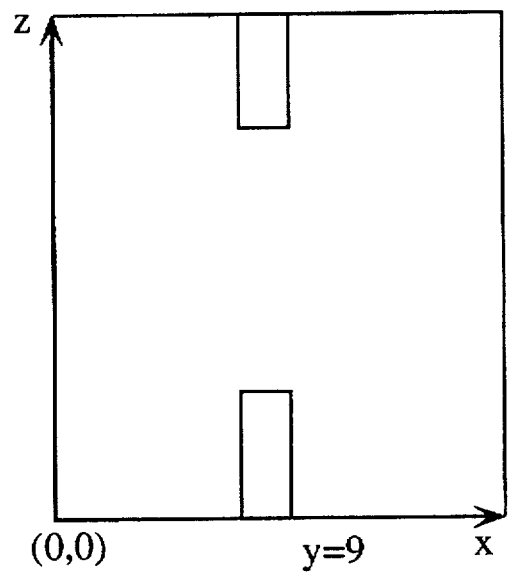
Figure 28C:
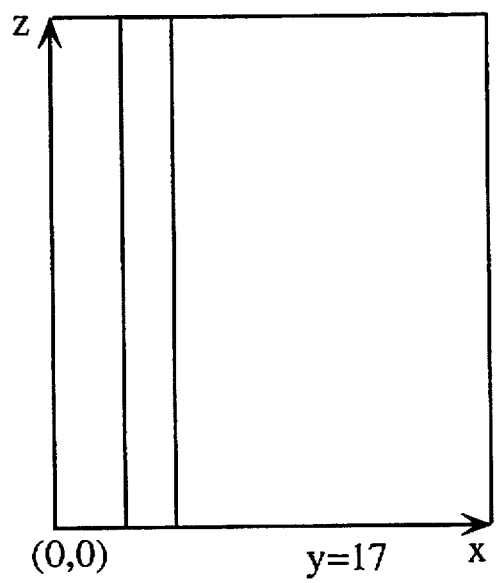

For the example of the three-dimensional object shown in FIG. 26, the X-Z cross-section when in y=1 is shown in FIG. 28A, the X-Z cross-section when in y=9 is shown in FIG. 28B, and the X-Z cross-section when in y=17 is shown in FIG. 28C.

Figure 28D:
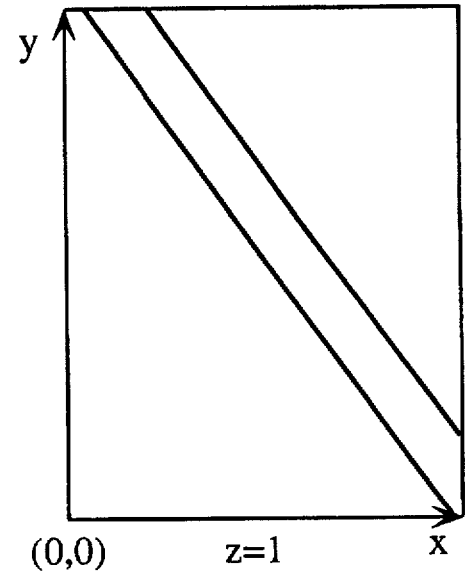
Figure 28E:
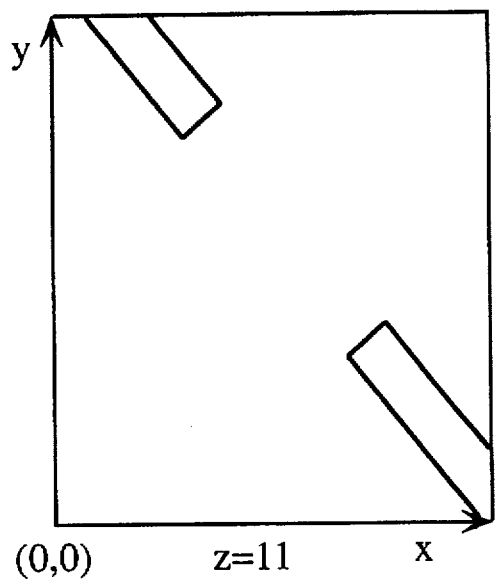
Figure 28F:
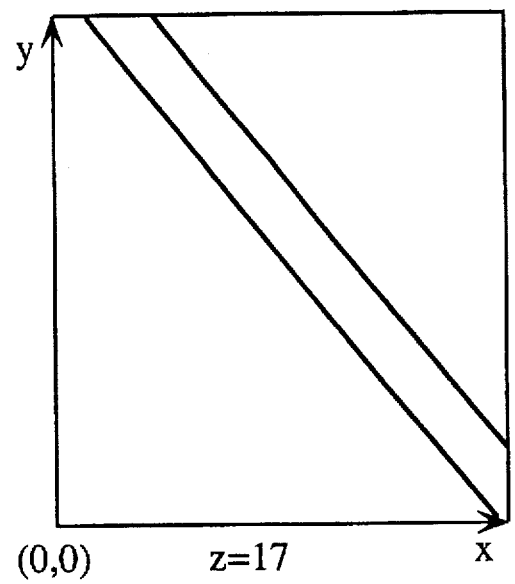
Figure 28G:
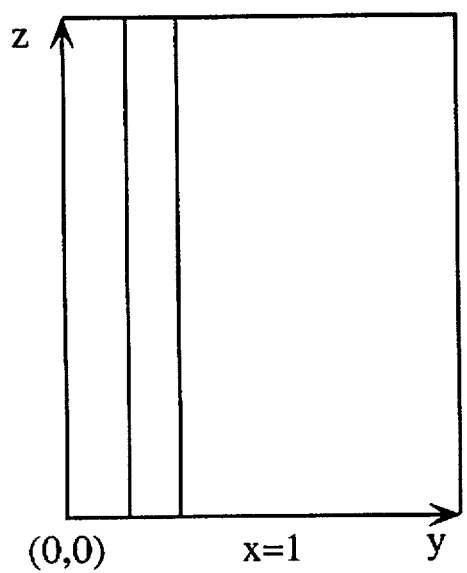
Figure 28H:
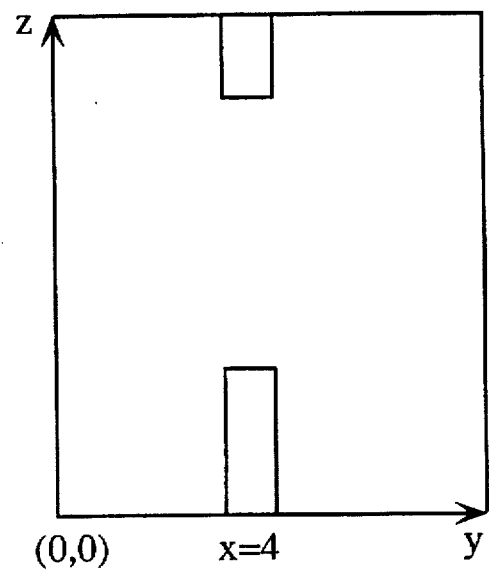
Figure 28I:
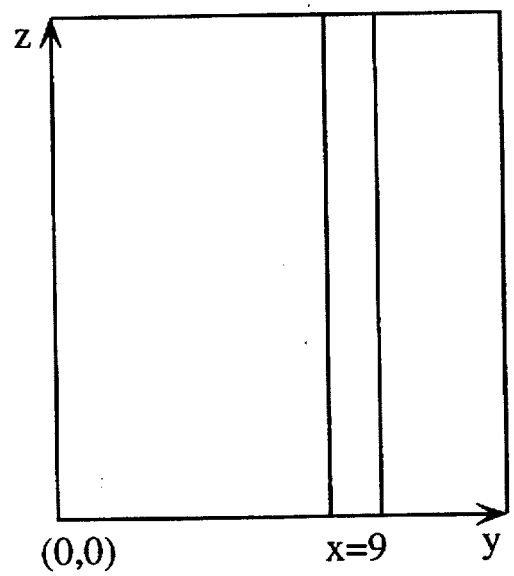

Cross-sectional images in the X-Y plane of the same three-dimensional object with different Z coordinates are shown in FIGS. 28D–28F. Similarly, cross-sectional images in the Y-Z plane of the same three-dimensional object with different X coordinates are shown in FIGS. 28G–28I.

Accumulative enhancement using search line segment filters is performed for these missing sections expressed as straight lines. Here, accumulative enhancement refers to the enhancement of an object pixel using pixel values which have already been enhanced themselves.

As an example, when the pixels a1, a2, a3, a4, and a5, in the 5*5 subpixel range whose center coincides with the center of the object pixel, have already been enhanced, accumulative enhancement calculates an average value using these enhanced pixels values instead of the original values of pixels a1, a2, a3, a4, and a5. The average value calculated using these enhanced pixel values is then set as the pixel value of the object pixel.

The following is an explanation of accumulative enhancement for the cross-section images obtained on a sectional face, with reference to FIGS. 29A–29G.

Figure 29A:
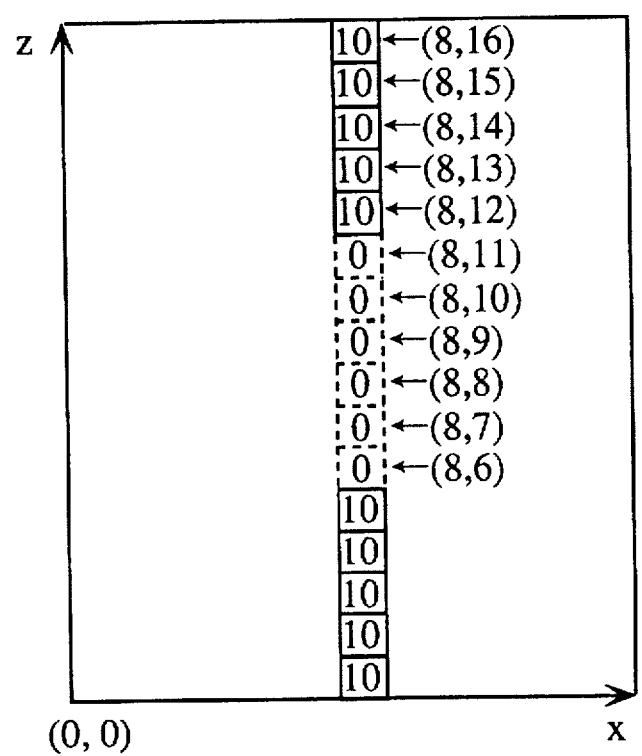
FIG. 29A to 29G show cumulative enhancement of a tomogram obtained as a cross-section.
Figure 29B:
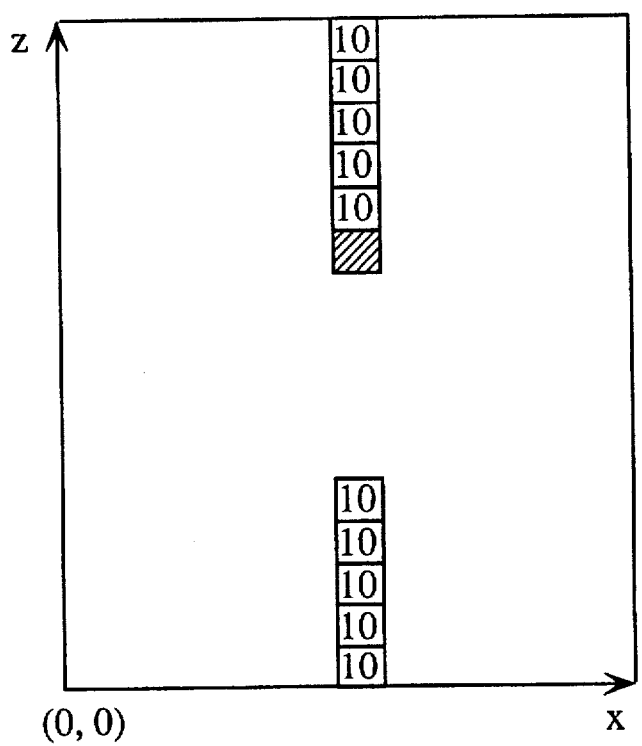
Figure 29C:
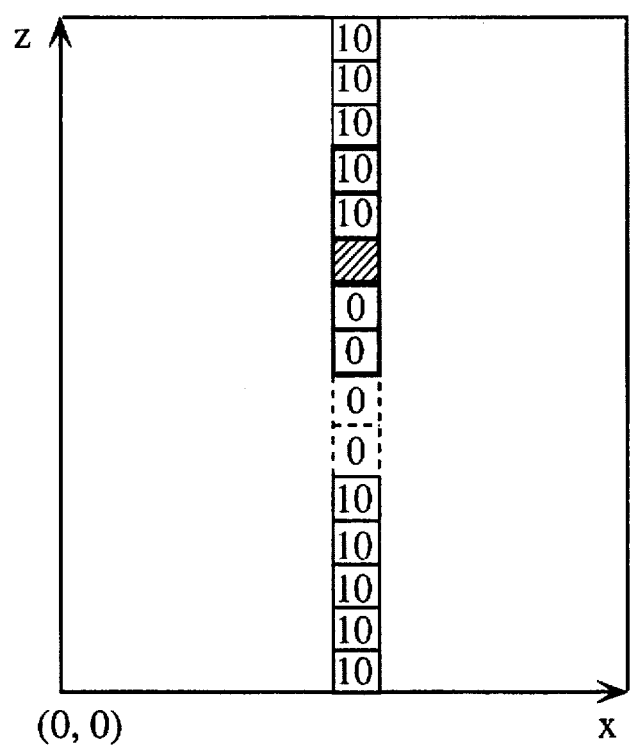

In the cross-section shown in FIG. 29A, the pixels (8,12) to (5,16) on the outline are clearly shown, while the pixels (8,6) to (8,11) on the outline are missing. Here, as shown in FIG. 29B, the pixel (8,11) is set as the object pixel and an average value is calculated using a range of five pixels. This five pixel range is shown in FIG. 29C, with the pixel values of (8,13) and (0,12) being "10" and the pixel values of (8,9) to (8,11) being "0", so that the average value is set as 10+10+0+0+0/5=4.

Figure 29D:
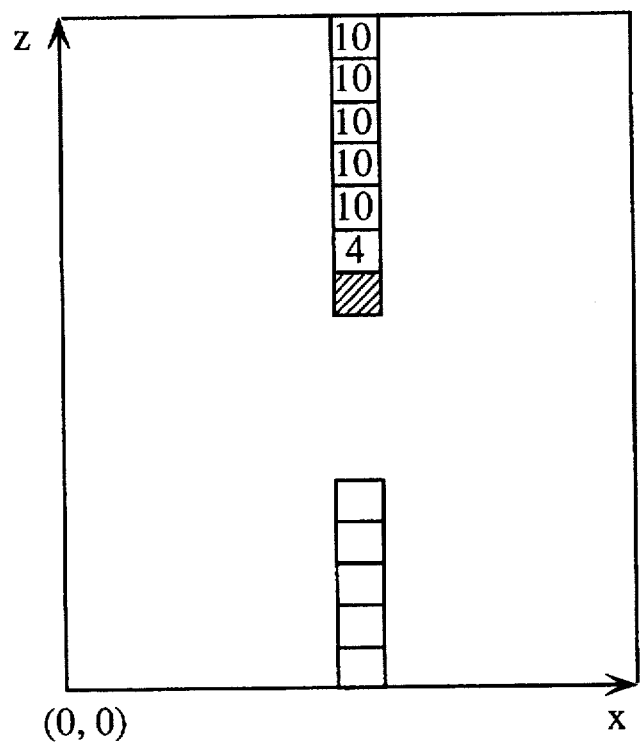
Figure 29E:
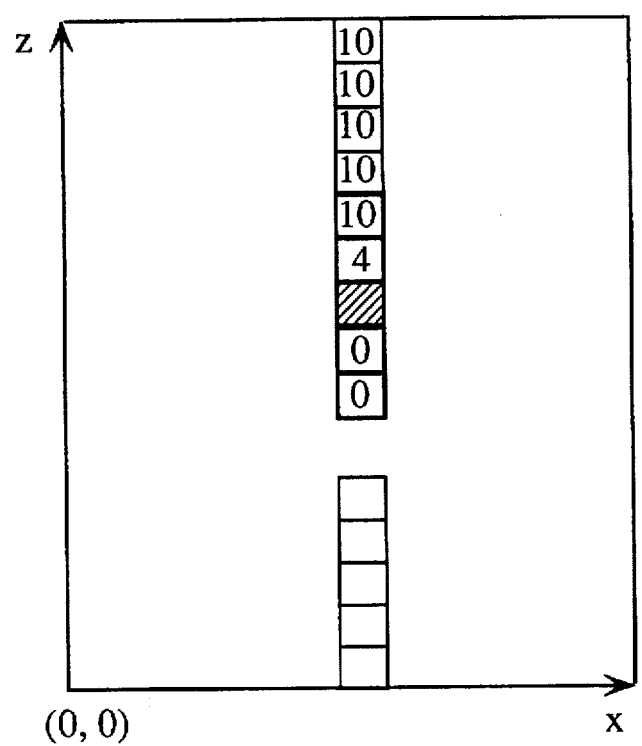

After the pixel value of (8,11) is set at "4" as shown in FIG. 29D, the pixel (8,10) is set as the object pixel and an average value is calculated using the range of five pixels shown in FIG. 29E. Here, the pixel values of (8,12) and (8,11) are "10" and "4", while the pixel values of (6,8) to (8,10) are "0", so that the average value is set as 10+4+0+0+0/5=2 (to one decimal place).

Figure 29F:
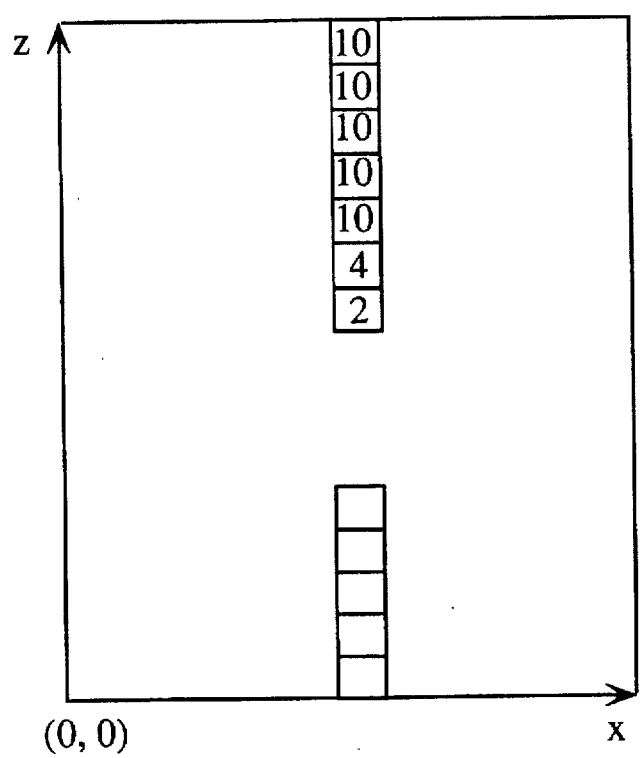
Figure 29G:
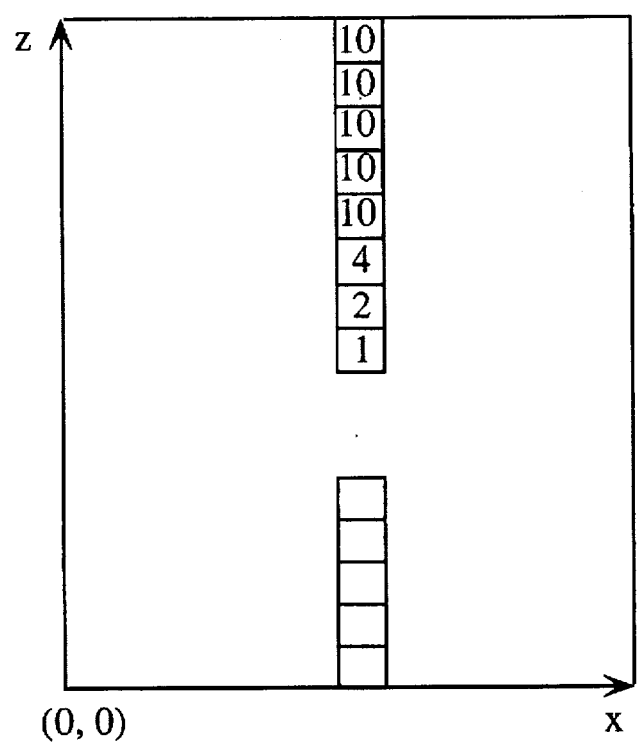

After the pixel value of (8,10) is set at "2" as shown in FIG. 29F, the pixel (8,9) is set as the object pixel and an average value is calculated using the range of five pixels shown in FIG. 29G. Here, the pixel values of (8,11) and (8,10) are "4" and "2", while the pixel values of (8,7) to (8, 9) are "0", so that the average value is set as 4+2+0+0+0/5=1 (to one decimal place).

Figure 30A:
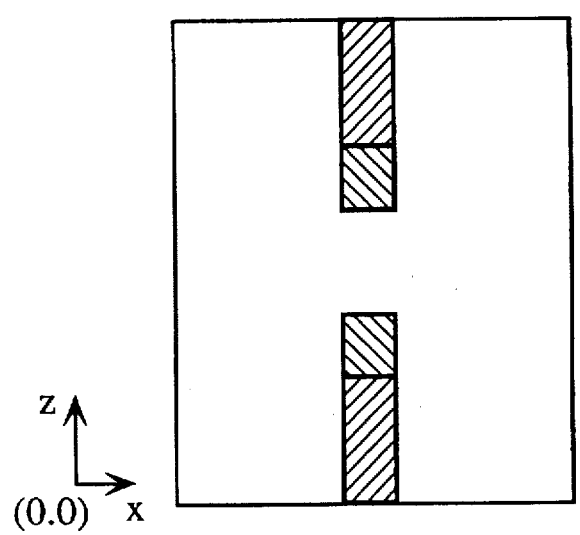
FIGS. 30A-30H show the progressive enhancement of a three-dimensional image.
Figure 30B:
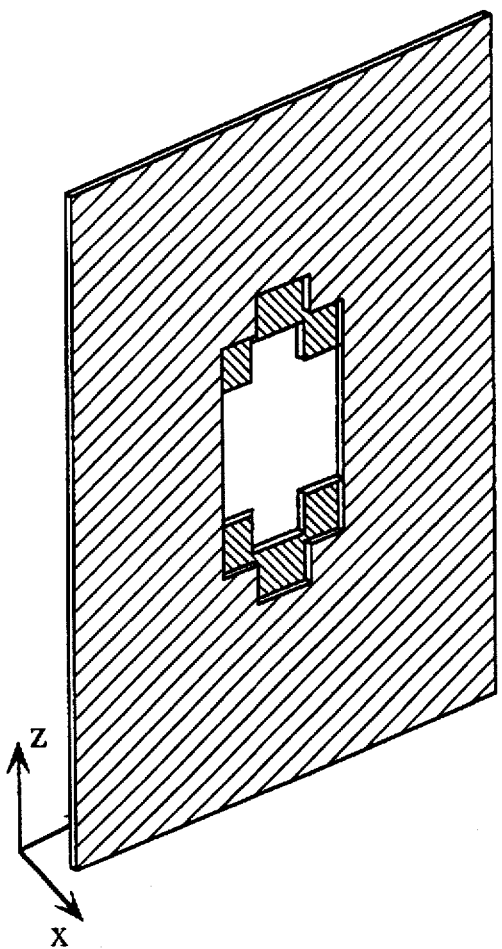

By doing so, the pixel values of pixels (8,12) to (8,9) become "10", "4", "2", and "1" respectively. For this setting, while the outline is not enhanced to become complete, the gradual setting of pixel values results in a missing part which is considerably narrower. FIG. 30A shows a cross-section in the X-Z plane after enhancement, with the bottom left-top right shading showing the original part of the three-dimensional image and the top left-bottom right shading showing the part which has been generated by image enhancement. When the above process is repeated for an X-Z sectional plane in the Y-axis, an enhancement of the missing part is added at the top and bottom. This is shown using top left-bottom right shading in FIG. 30D.

Once image enhancement has been completed for all of the X-Z sectional images, accumulative enhancement is performed for X-Y cross-sections all of the Z coordinates. It should be noted here that the enhanced part appears on these X-Z cross-sectional images and not just an the three-dimensional image.

Figure 30C:
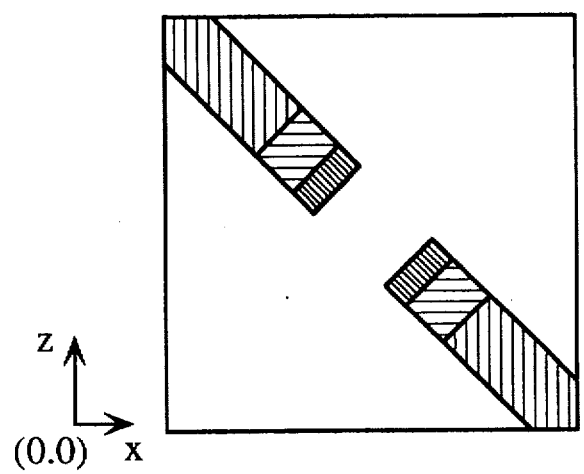

FIG. 30C shows a cross-section in the X-Z plane after enhancement, with the top left-bottom right shading showing the part which has been generated by image enhancement. Here, the part shown by horizontal shading shows the enhancement which was made in the X-Y plane by cumulative enhancement.

Figure 30D:
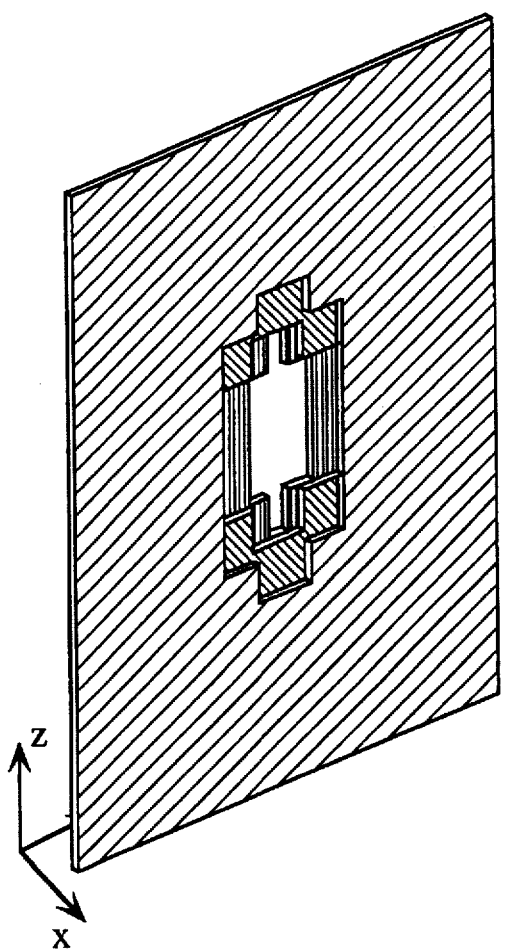

Once image enhancement has been completed for all of the X-Y sectional images, an enhanced part which extends further into the missing part is generated, as shown by the vertical shading in FIG. 30D. When this has been repeated for all of the X-Y sectional images, cumulative enhancement is performed for the Y-Z cross-sectional images for all X coordinates. It should be noted here that the enhanced part appears on these Y-Z cross-sectional images and not just on the three-dimensional image.

Figure 30E:
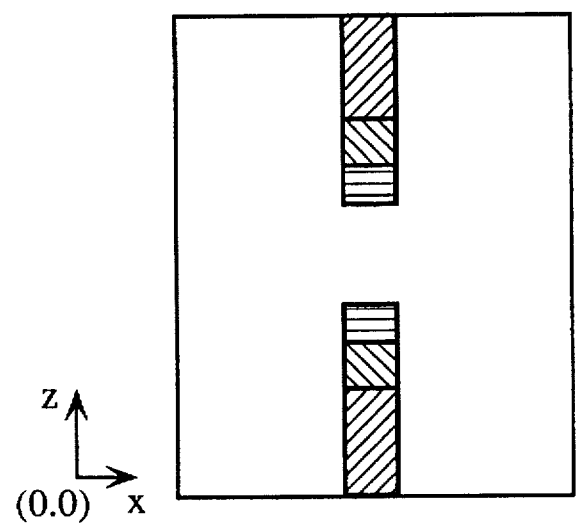

FIG. 30E shows n cross-section in the Y-Z plane after enhancement, with the horizontal shading showing the part which has been generated by image enhancement in this Y-Z plane, and while the top left-bottom right shading shows the effect of the cumulative enhancement made by the previous processing in other planes. Here, the part shown by horizontal shading shows the enhancement which was made in the X-Y plane by cumulative enhancement.

Figure 30F:
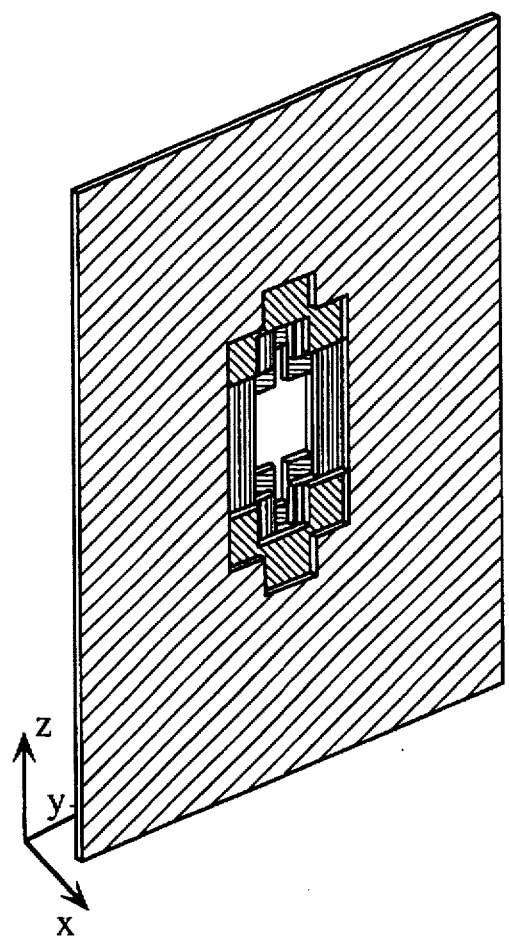

Once image enhancement has been completed for all of the Y-Z sectional images, an enhanced part which extends further into the missing part is generated, as shown by the horizontal shading in FIG. 30F.

Figure 30G:
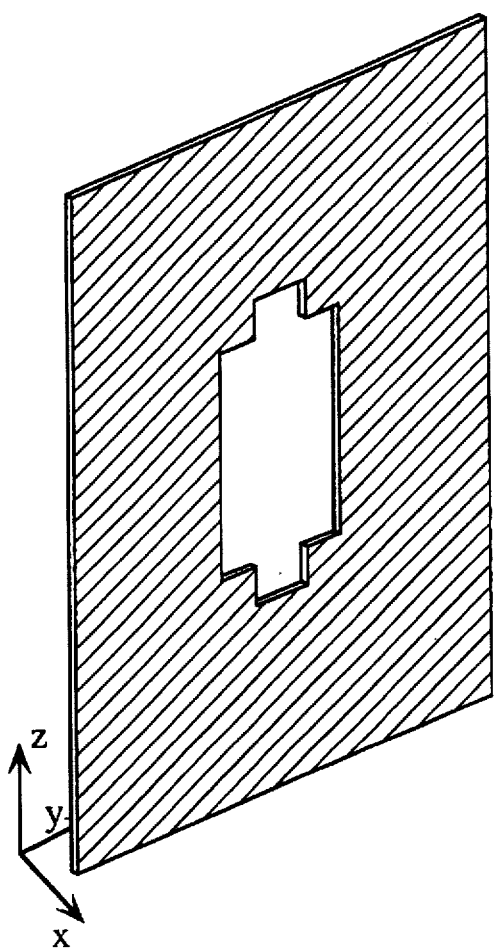
Figure 30H:
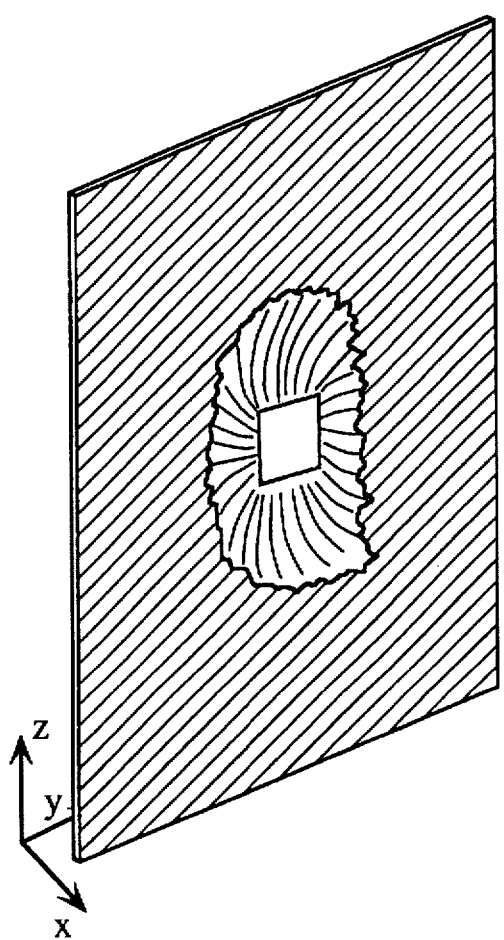

When cumulative enhancement has been performed for all of the X-Y sections, all of the X-Z sections and all of the Y-Z sections, the missing part of the three-dimensional image shown in FIG. 30G is reduced to the smaller, loss noticeable missing part shown in FIG. 30H.

The following is a description of the enhancement of sectional images performed by the processor 18 in accordance with the flowcharts shown in FIGS. 31 to 34.

Figure 31:
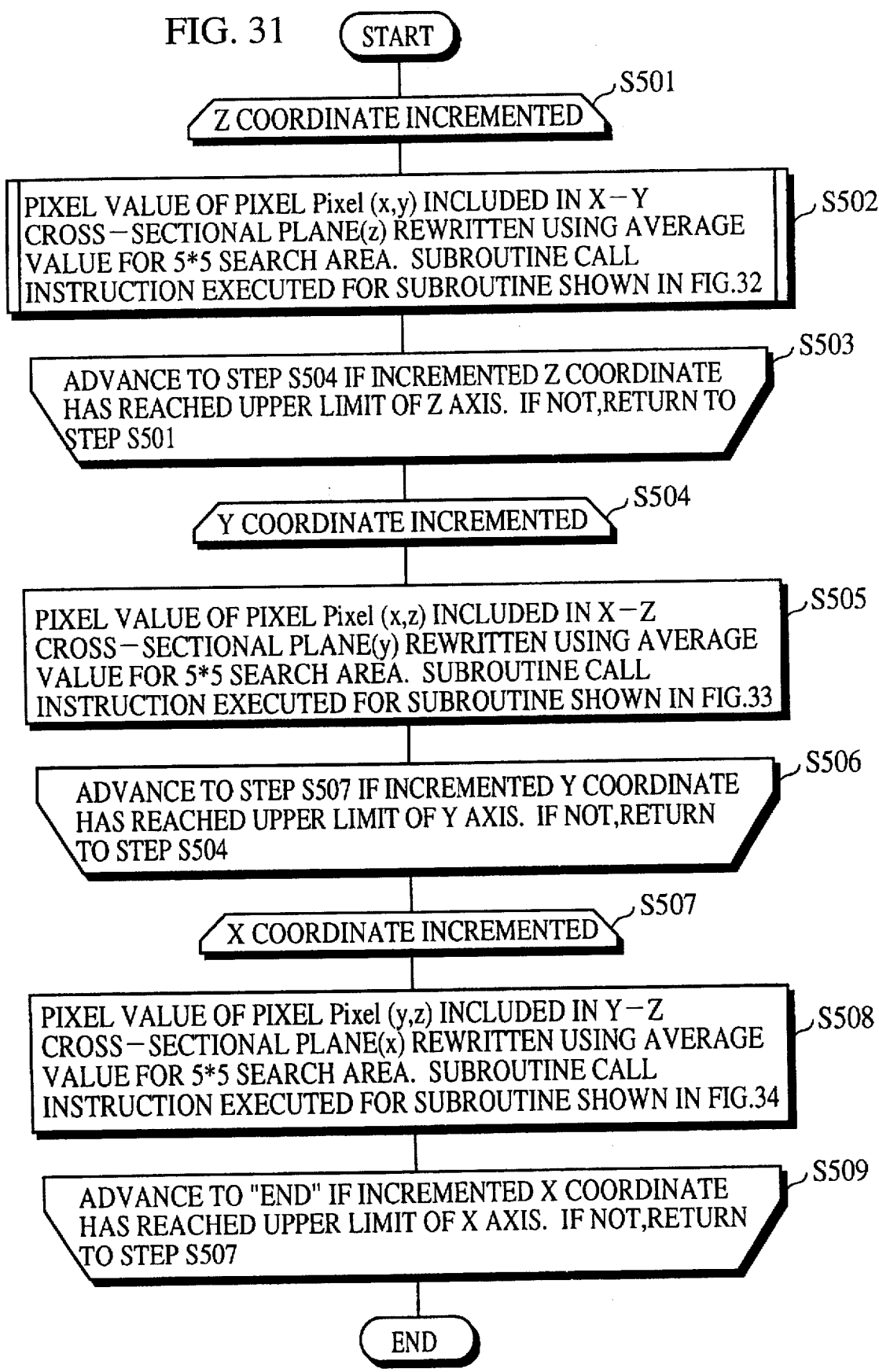
FIG. 31 is the main flowchart for image enhancement using tomograms.

The X-Y sectional plane "Plane(Z)" in the flowchart of FIG. 31 is a X-Y section which has a Z coordinate which is incremented for each iteration of the loop from step 501 to step 503. In steps 501, the Z coordinate is incremented by one and in step 502 a subroutine for rewriting the pixel values of all the pixels in the X-Y sectional plane "Plane(Z)" for the current value of Z is called. This subroutine is shown in FIG. 32.

Figure 32:
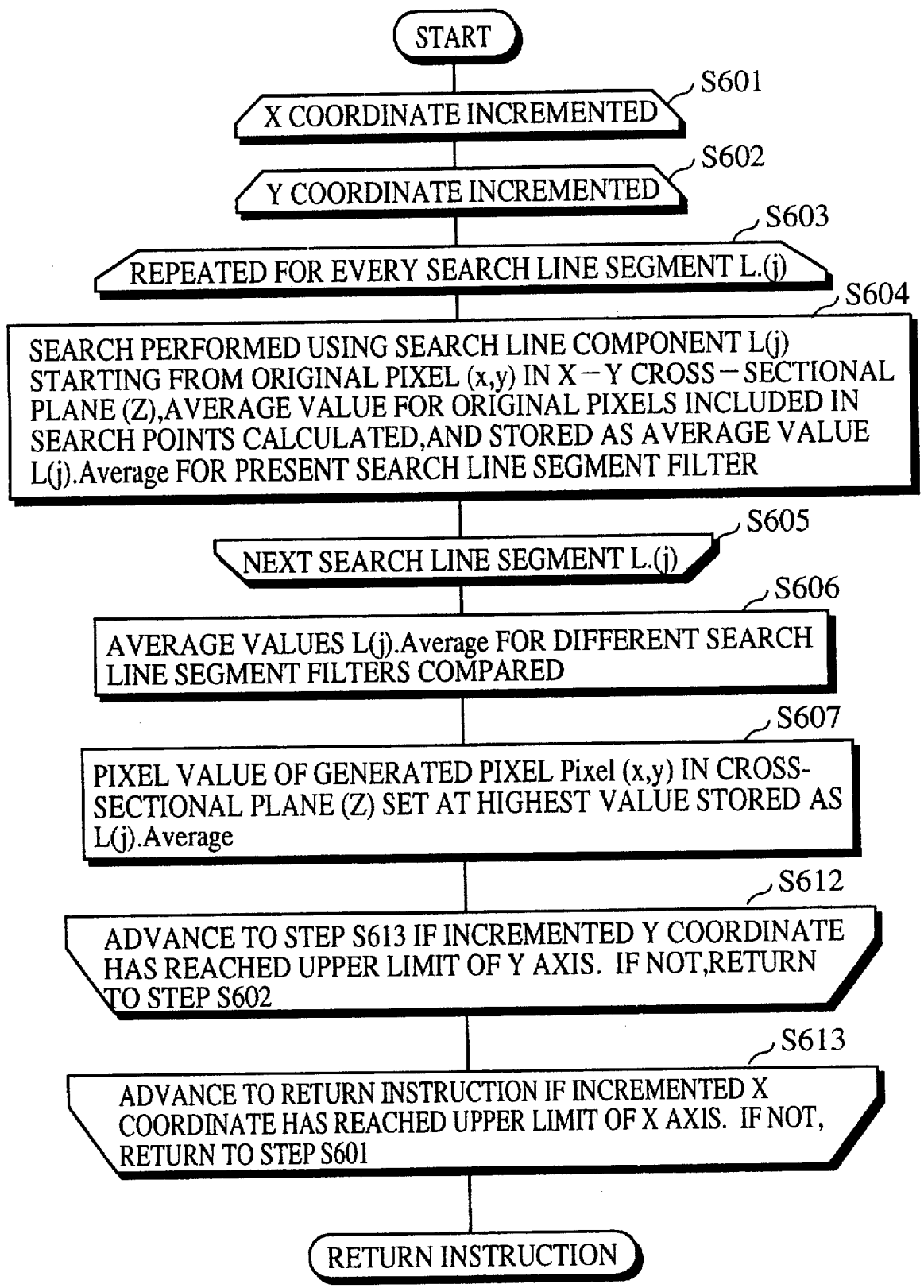
FIG. 32 is a flowchart showing the procedure for image enhancement in the X-Z plane.

In the subroutine in FIG. 32, steps 602 to 612 are a loop for scanning the pixels on an X-Y plane in the Y direction, with the Z coordinate being incremented for each iteration. Similarly, steps 601 to 613 are a loop for scanning the pixels on an X-Y plane in the X direction, with the X coordinate being incremented for each iteration.

When the X coordinate is incremented, in step 604 the processor 18 performs a search using the search line segment L(j) setting the Pixel(x,y) as the starting point, finds an average value of the pixels included in the search points, and stores the result as the search line segment average value L(j).Average.

Once the average value of every search line segment filter has been calculated, in step 606 the processor 18 compares the average values L(j) for different search line segments and advances to step 607. In step 607, the processor 18 sets the highest out of the compared average values as the pixel value Pixel(x,y).Value in the Plane(Z).

Once all of the iterations of loops steps 602–612 and steps 601–613 have been performed, the return instruction at the bottom of the flowchart is executed and the processing advances to step 503 in FIG. 31. In step 503, the processor 18 determines whether the z coordinate has reached an upper limit and, if not, advances to step 501 where the Z coordinate is incremented once again.

The processing in steps 501–503 is repeated until the Z coordinate reaches the upper limit for the object of image formation. Once this upper limit has been reached, the processing advances to step 504.

The X-Z sectional plane Plans (Y) referred to in step 504 is an X-Z sectional plane whose Y coordinate is incremented in each iteration of the loop in steps 504 to 506.

Figure 33:
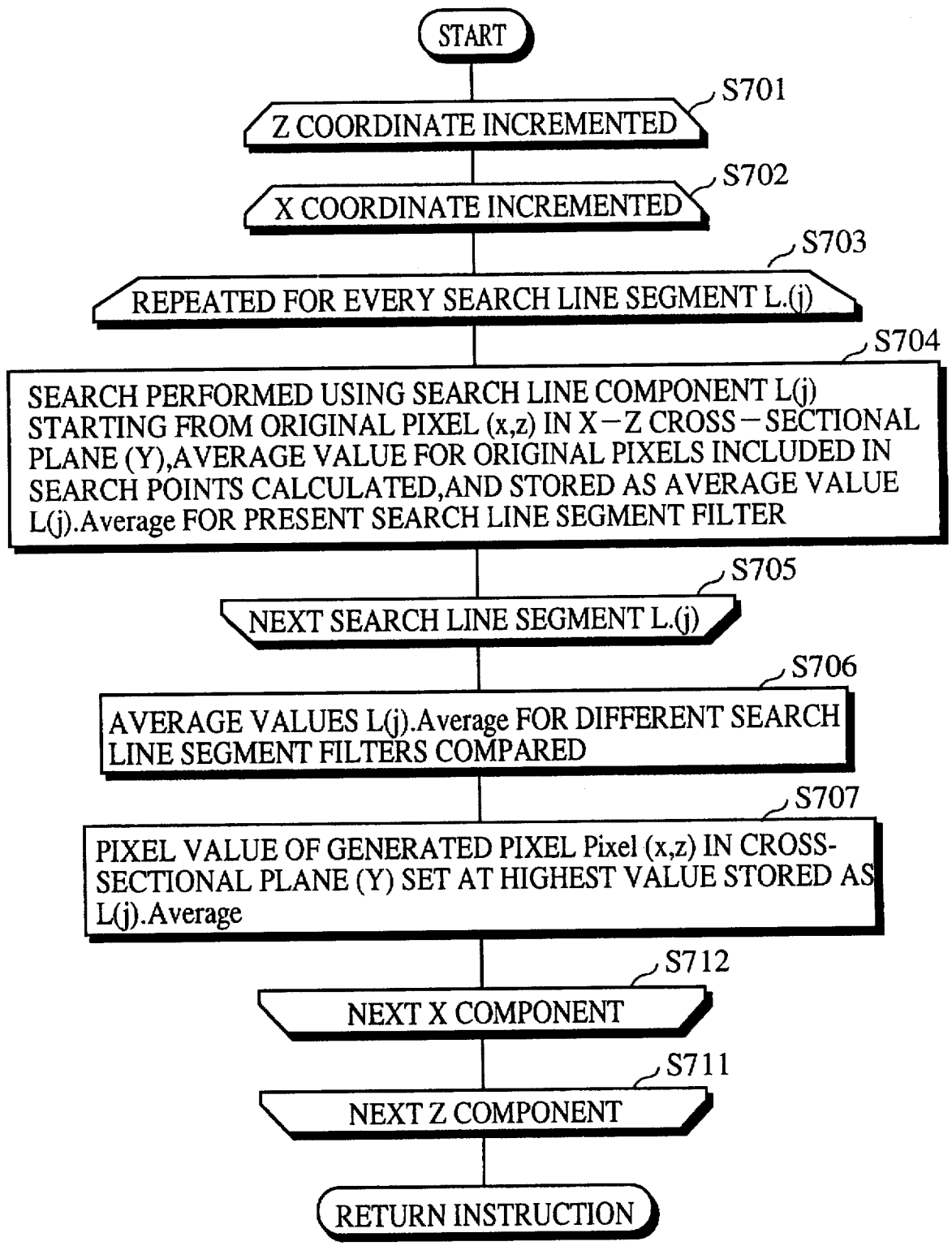
FIG. 33 is a flowchart showing the procedure for image enhancement in the X-Y plane.

Once the Y coordinate has been incremented in steps 504–506, the pixel values of all of the pixels distributed on the X-Z sectional plane which have the current Y coordinate are rewritten by executing a subroutine call Instruction in step 505 which transfers the processing to the flow shown in FIG. 33.

In the subroutine in FIG. 33, steps 702 to 712 form a loop for scanning the pixels on an X-Z plane in the X direction, with the X coordinate being incremented for each iteration. Here, steps 701 to 711 form a loop process for sliding the scanning performed in the X-axis in the direction of the Z-axis.

Once the X coordinate has been incremented, in step 704 the processor 18 performs a search using the search line segment L(j) setting the Pixel(x,z) as the starting point, finds an average value of the pixels included in the search points, and stores the result as the search line segment average value L(j).Average.

Once the average value of every search line segment filter has been calculated, in step 706 the processor 18 compares the average values L(j) for different search line segments and advances to step 707. In step 707, the processor 18 sets the highest out of the compared average values as the pixel value Pixel(x,z).Value in the Plane(Y).

Once all of the iterations of loops steps 702–712 and steps 701–711 have been performed, the return instruction at the bottom of the flowchart is executed and the processing advances to step 506 in FIG. 31. In step 506, the processor 18 determines whether the Y coordinate has reached an upper limit and, if not, advances to step 504 where the Y coordinate is incremented once again.

The processing in steps 504–506 is repeated until the Y coordinate reaches the upper limit for the object of image formation. Once this upper limit has been reached, the processing advances to step 507.

The Y-Z sectional plane Plane(X) referred to in step 508 is an Y-Z sectional plane whose X coordinate is incremented in each iteration of the loop in steps 507 to 509.

Figure 34:
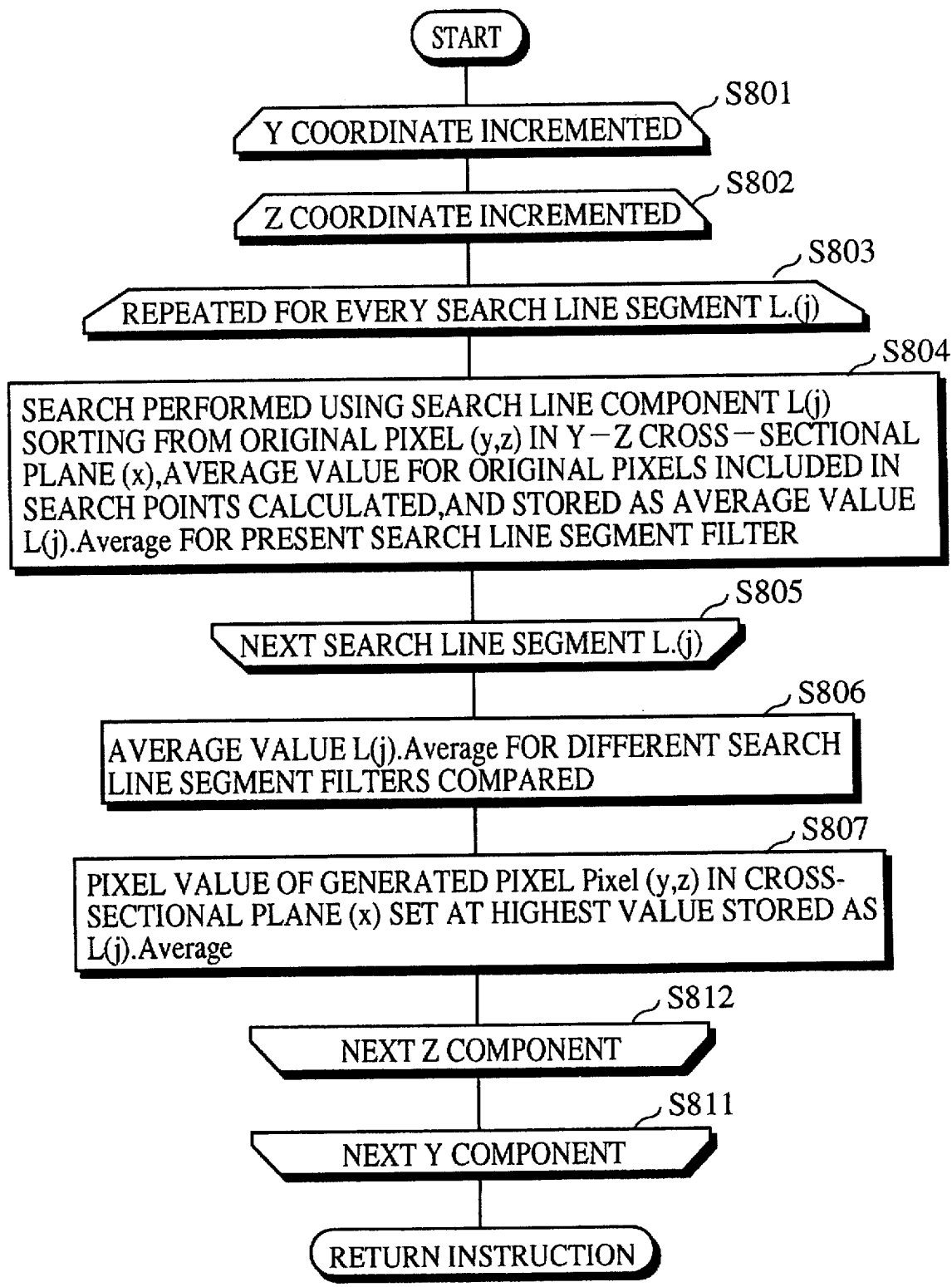
FIG. 34 is a flowchart showing the procedure for image enhancement in the Y-Z plane.

Once the X coordinate has been incremented in steps 507–509, the pixel values of all of the pixels distributed on the Y-Z sectional plane which have the current X coordinate are rewritten by executing a subroutine call instruction in step 508 which transfers the processing to the flow shown in FIG. 34.

In the subroutine in FIG. 34, steps 802 to 812 form a loop for scanning the pixels on a Y-Z plane in the Z direction, with the z coordinate being incremented for each iteration. Here, steps 801 to 811 form a loop for sliding the scanning performed in the Z-axis in the direction of the Y-axis.

When the Z coordinate is incremented, in step 804 the processor 18 performs a search using the search line segment L(j) setting the Pixel(y,z) as the starting point, finds an average value of the pixels included in the search points, and stores the result an the search line segment average value L(j).Average.

Once all of the iterations of loops steps 801–811 and steps 802–812 have been performed, the return instruction at the bottom of the flowchart is executed and the processing advances to step 509 in FIG. 31. In step 509, the processor 18 determines whether the X coordinate has reached an upper limit and, if not, advances to step 507 where the X coordinate is incremented once again.

By means of the operation described above, the present embodiment generates a plurality of cross-sectional images of a three-dimensional object, in doing so using search line filters to enhance any missing parts of the outlines of the image. In performing enhancement, one out of a plurality of search line segment filters with different curvatures and inclinations is selected in accordance with its conformity to the form of the outline, so that the generated three-dimensional image is faithful to the form of the original object.

Fifth Embodiment

Figure 35A:
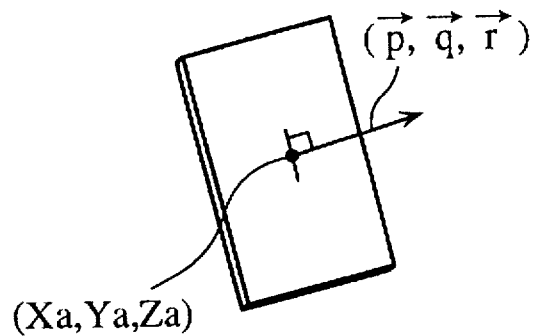
FIGS. 35A and 35B show three-dimensional objects expressed using surface information.
Figure 35B:
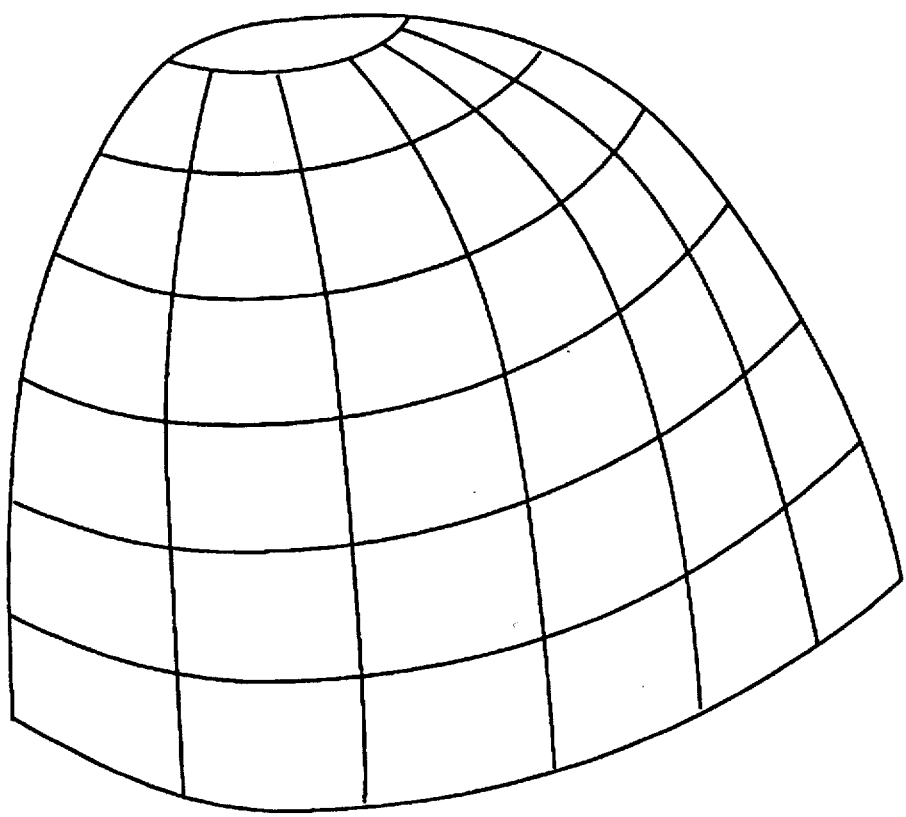
Figure 36A:
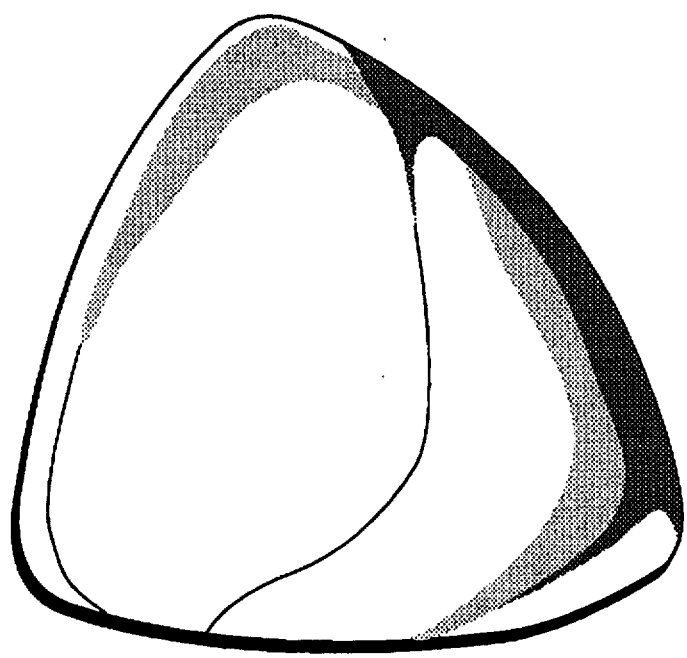

The apparatus of the fifth embodiment of the present invention generates enhanced surface information from a three-dimensional image which is included in tomograms. The surface information referred to here is expressed, as shown in FIG. 35A, using normal vectors (p,q,r) and spatial coordinates (Xa, Ya, Za) at the center, as well as the height and width of the surface. Here, in the surface information, a condition is set for any arbitrary point (X, Y, Z) on the surface and the normal vector so that $pX+qY+rZ=1$. A three-dimensional object expressed by the surface information is shown in FIG. 35B. If a three-dimensional object is expressed using surface information in this way, it becomes possible to edit the three-dimensional image using a conventional computer graphics program. As one example, using a shading process, shadows can be calculated for an indicated viewpoint and light source, before being added to the three-dimensional image, as shown in FIG. 36A. Alternatively, using a texture mapping process, a pattern or design expressed as texture data can be added to the surfaces of the object, as shown in FIG. 36B.

The present embodiment uses a technique called "distribution analysis vector generation" to generate appropriate surface information. Here, "distribution analysis" refers to analysis of the inclination of the surfaces of the three-dimensional image from the distribution of the pixel values in two-dimensional space, and generation of normal vectors which correspond to this inclination. This is performed using vector search filters.

Figure 37:
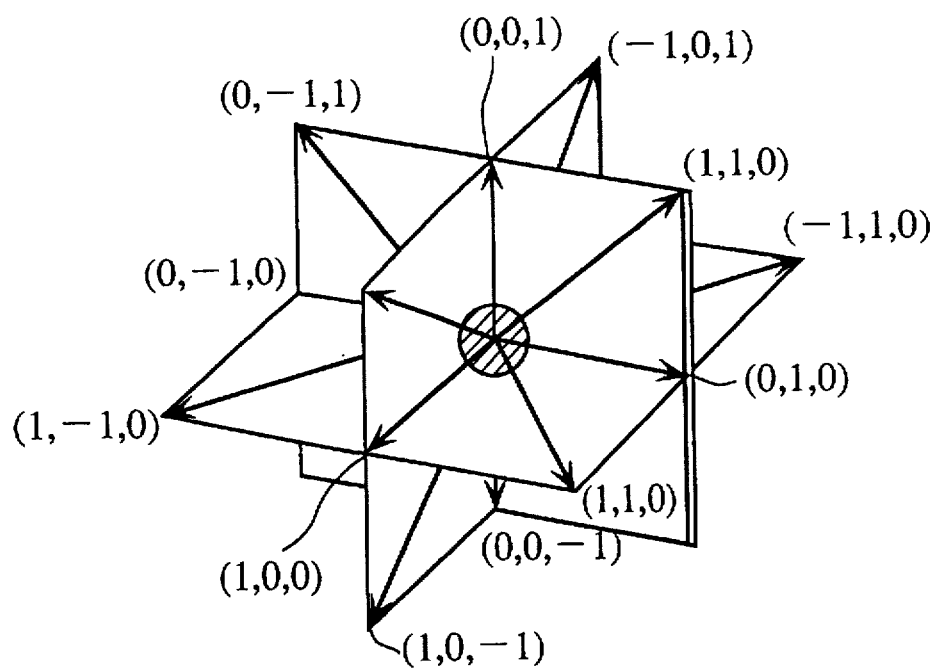
FIG. 37 shows the object pixel and every search direction.

Vector search filters indicate all of the search directions starting from the object pixel and, as shown in FIG. 37, are expressed by unit vectors, such as (0,0,1), (0,0,−1), (1,0,0), and (−1,0,0). Each direction expressed by a search vector searches a predetermined number (universally set at "3" in the present embodiment) of pixels in the designated direction and calculates an average value out of all the search points. These calculated values express the magnitude of the pixel values in each direction.

In the present embodiment, the normal vectors for the surface information are obtained by calculating compound vectors which are made up of unit vectors which are weighted in accordance with the calculated averages of the pixel values. Here, these compound vectors can be considered as approximating to the normal vectors.

Figure 38A:
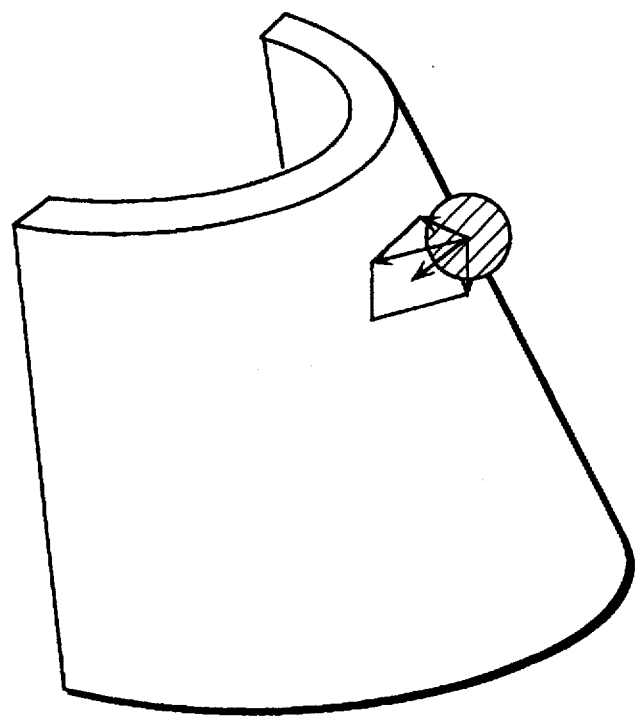
FIGS. 38A-38C show images in perspective, from the side, and from the top of a three-dimensional object achieved by stacking tomograms when an object pixel is located on the outline of the object.

FIG. 38A shows the three-dimensional object which is obtained by stacking tomograms. In this drawing, the "ball" attached to the sloping surface is a model representation of an object pixel which is located on the boundary of the three-dimensional object.

Figure 38B:
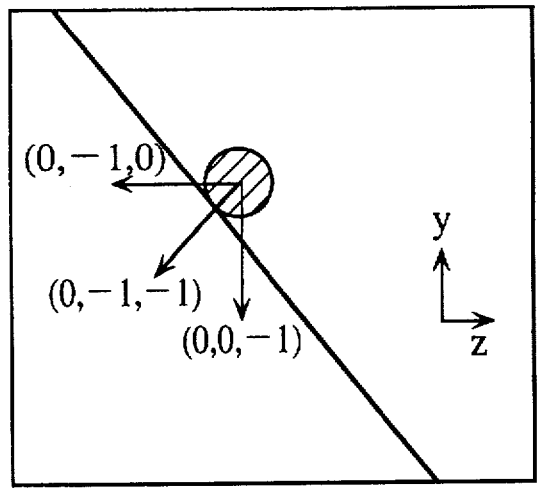

When the positional relationship between the object pixel and the object is as shown in FIG. 38A, average values are calculated for each of the directions expressed, as shown in FIG. 37, as unit vectors. In this case, for the Y-Z plane, unit vectors (0,−1,0), (0,−1,−1), and (0,0,−1), shown in FIG. 38B, which are calculated for the three-dimensional object side result in high average values. In the X-Y plane, unit vectors (1,0,0), and (1,−1,0), and (0,0,−1), shown in FIG. 38C, which are calculated for the three-dimensional object side result in high average values.

Figure 39:
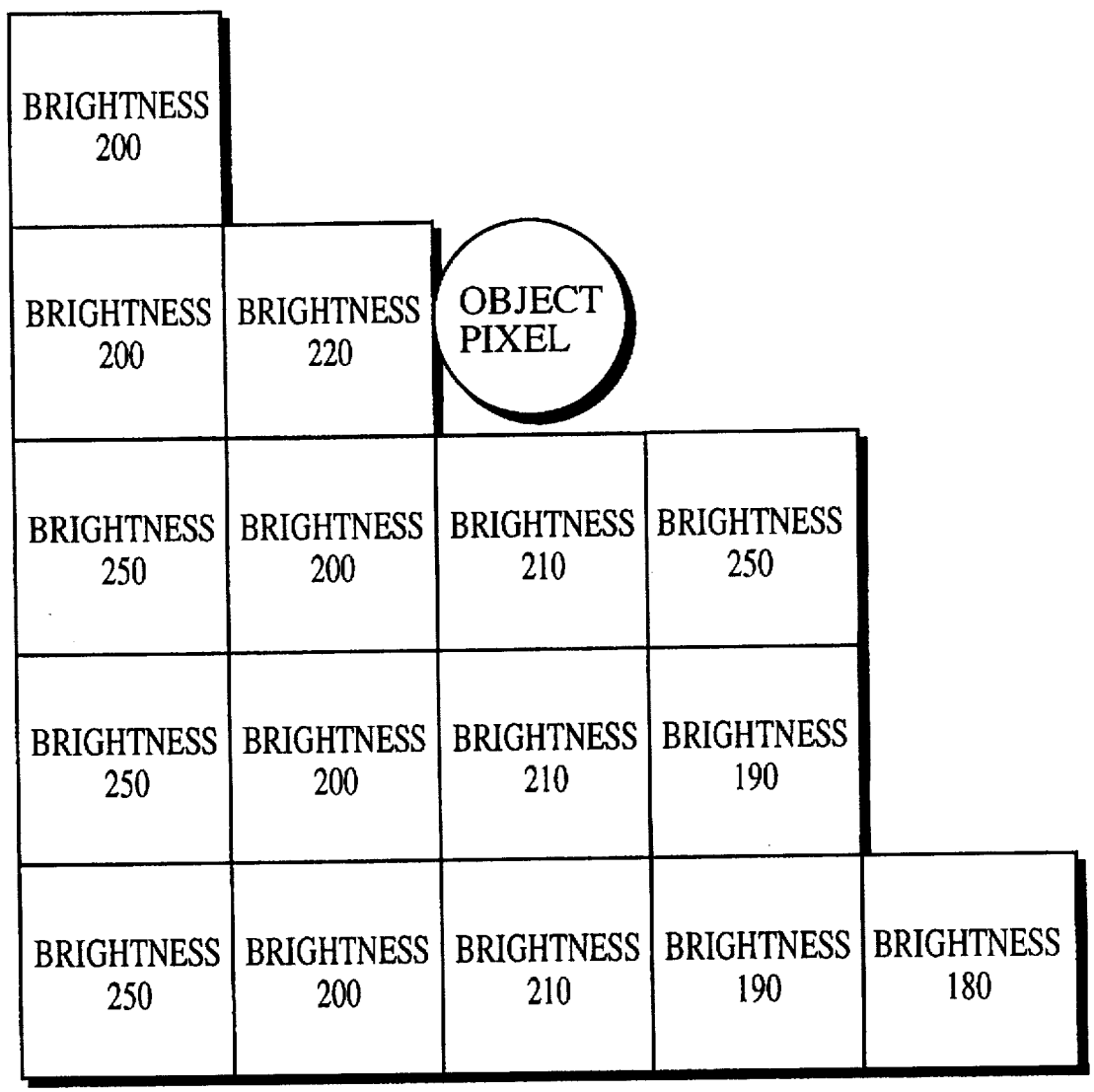
FIG. 39 shows the distribution of pixel values of the three-dimensional object.

The following is an example of calculation of the average values in each direction for the Y-Z plane of the object shown in FIG. 38A. When the pixel values of each pixel are distributed an shown in FIG. 39, the overage value for each direction in the Y-Z plane is calculated as shown below.

average pixel value for direction given by unit vector (0,−1, 0) ... (200+220+0)/3=140 average pixel value for direction given by unit vector (0,−1, −1) ... (250+200+0)/3 =150 average pixel value for direction given by unit vector (0, 0, −1) ... (210+210+0)/3 =140 average pixel value for direction given by unit vector (0, 1, −1) ... (250+0+0)/3 =83.3 average pixel value for direction given by unit vector (0, 0, 1) ... (0+0+0)/3 =0 average pixel value for direction given by unit vector (0, 1, 1) ... (0+0+0)/3 =0 average pixel value for direction given by unit vector (0, 1, −1) ... (250+0+0)/3 =83.3 average pixel value for direction given by unit vector (0, 1, 0) ... (0+0+0)/3 0

The average values written above are used to weight the unit vectors to give the following vectors for the object pixel.

(0, −140, 0)

(0, −150, −150)

(0, 0, −140)

(0, 83.3, 83.3)

Figure 40A:
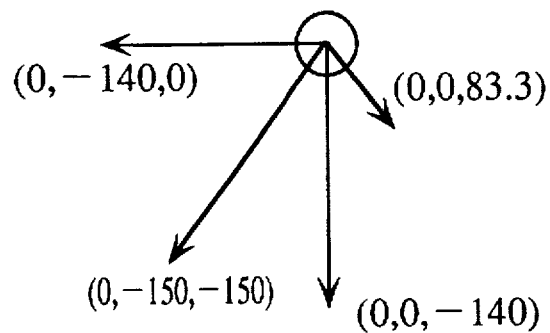
FIGS. 40A and 40B show compound vectors of an object pixel.
Figure 40B:
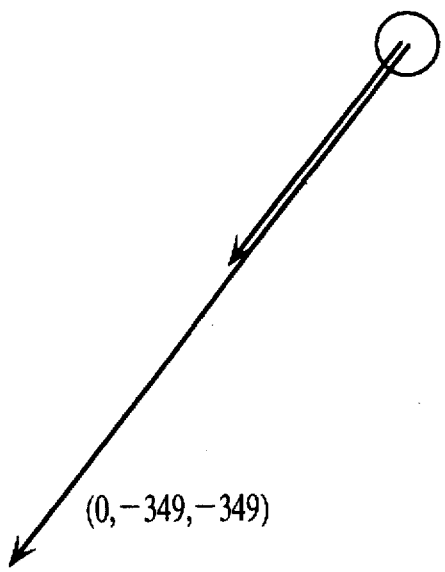

These vectors for the three-dimensional object are expressed in the Y-Z plane using the vectors given above. By combining these vectors, the compound vector for the object pixel can be obtained, as shown in FIG. 40B.

Figure 38C:
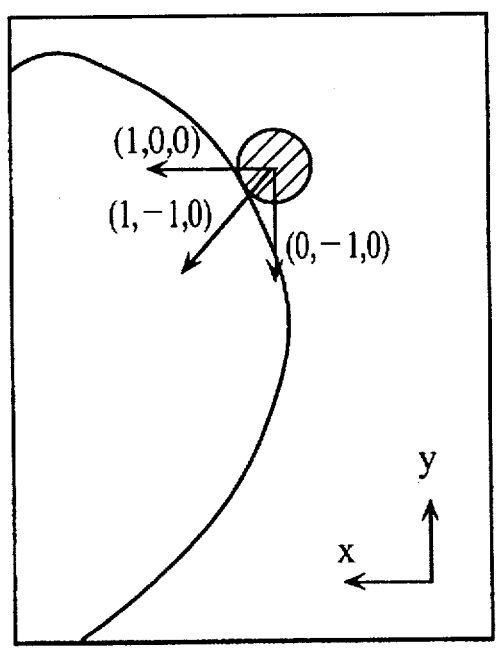
Figure 41A:
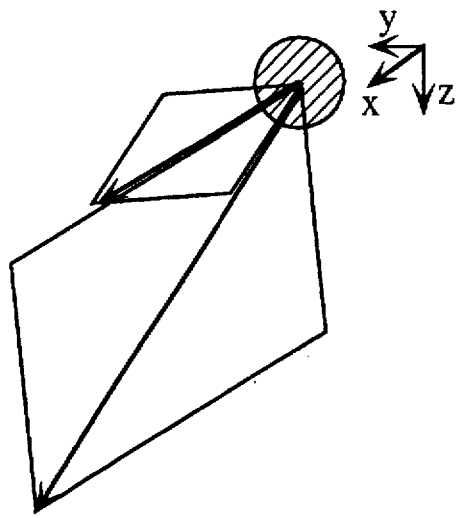
FIGS. 41A-41G show compound vectors of an object pixel, and a normal vector of the compound result.
Figure 41B:
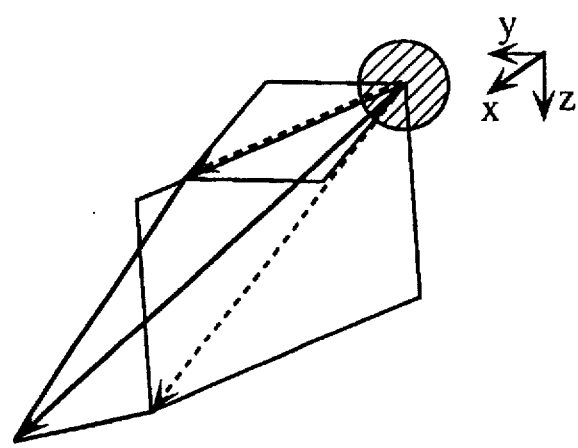

The procedure described above is also performed for the X-Y surface shown in FIG. 38C. If the compound vectors obtained in the X-Y plane are expressed along with the compound vectors in the Y-Z plane, the result will be as shown in FIG. 41A. If these compound vectors in the X-Y plane are combined with the compound vectors in the Y-Z plane, the resulting compound vector will be as shown in FIG. 41B. As described above, since the object pixel was selected as a pixel on the boundary of the three-dimensional object, the compound vector obtained in FIG. 41B shows the inclination of the surface of the three-dimensional object. Here, a unit vector calculated from this compound vector can be considered as being equal to a normal vector of the surface of the object.

Figure 41C:
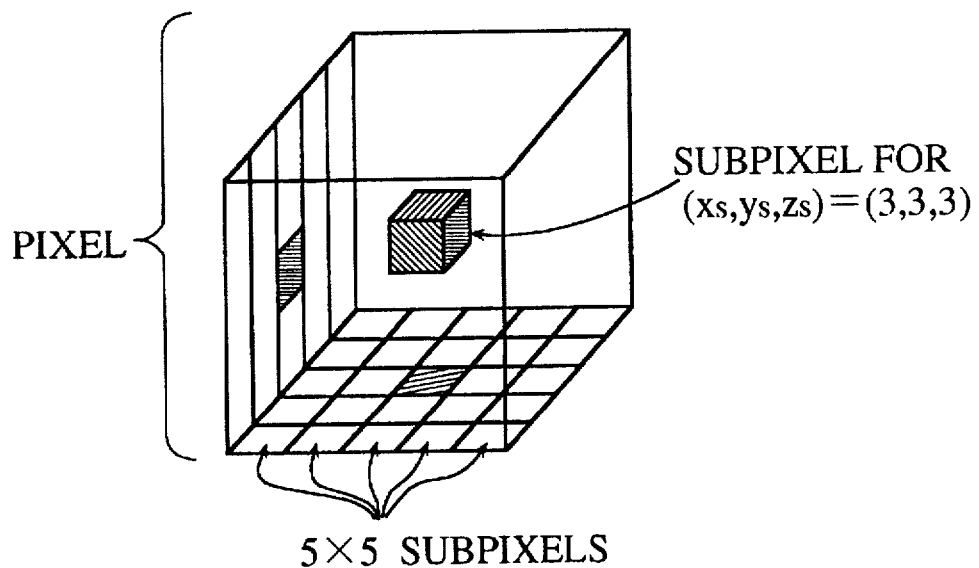
Figure 41D:
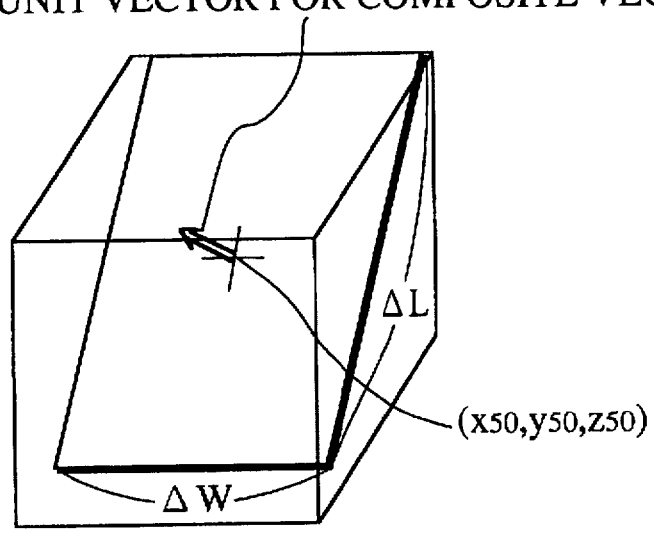

Normal vectors for surfaces, which form a part of information elements in the surface information, are calculated as described above. Following this, the remaining parts of the surface information, which is to say, spatial coordinates and height/width are calculated. In the present embodiment, center coordinates in a subpixel coordinate system are generated for the object pixel, as shown in FIG. 41C, as suitable coordinates for the normal vector. The center coordinates in a subpixel coordinate system shown in FIG. 41C is the subpixel whose position, when a 5*5*5 subpixel coordinate system is used, which is located at (x, y, z)=(3, 3,3). Once these center coordinates (Xs, Ys, Zs) have been found, a plane whose inclination is given by the normal vector (p, q, r) is generated inside the subpixel coordinate system so as to pass through these center coordinates. Thin is shown in FIG. 41D. After this, the lengths of the sides of the plane which cross the coordinate system are calculated and as set as the height ΔL and width ΔW. This height ΔL and width ΔW are then combined with the normal vector and the center coordinates to compose one set of surface information which corresponds to one part of the three-dimensional object.

Figure 41E:
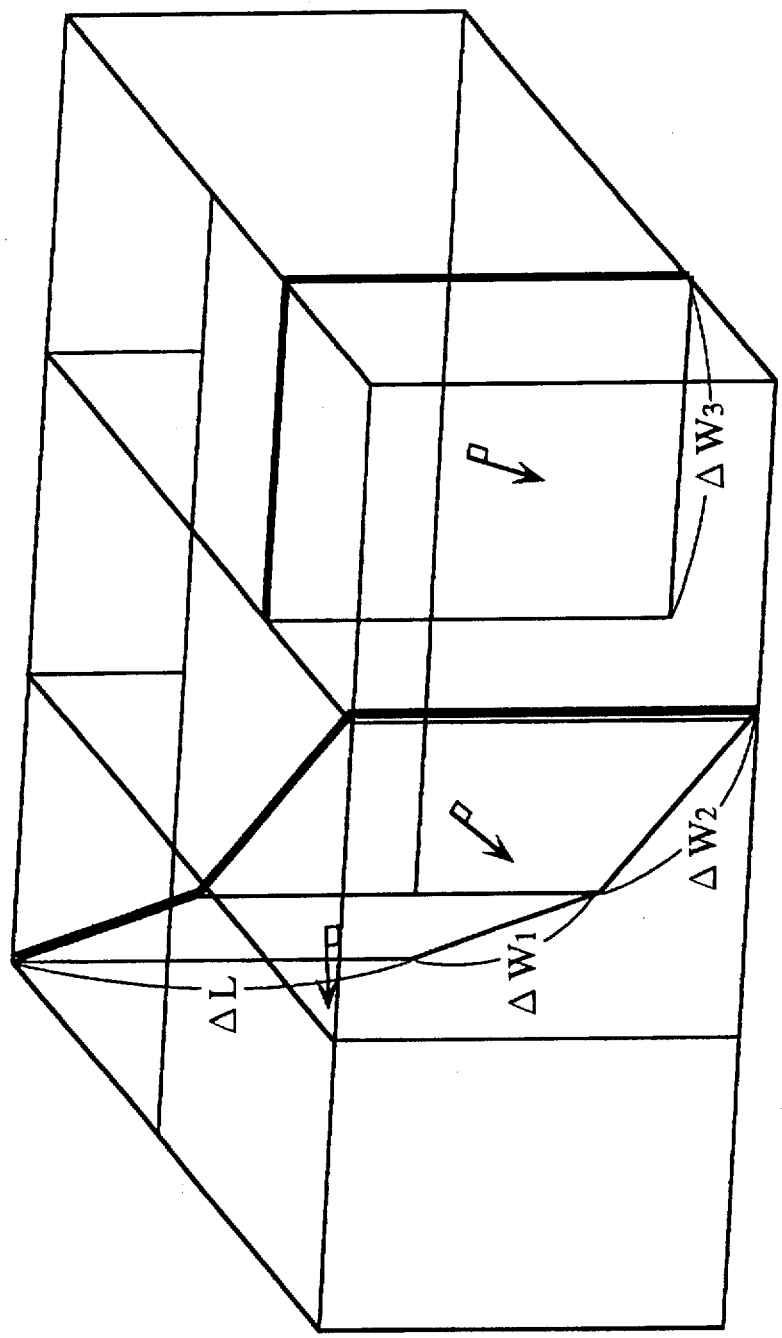
Figure 41F:
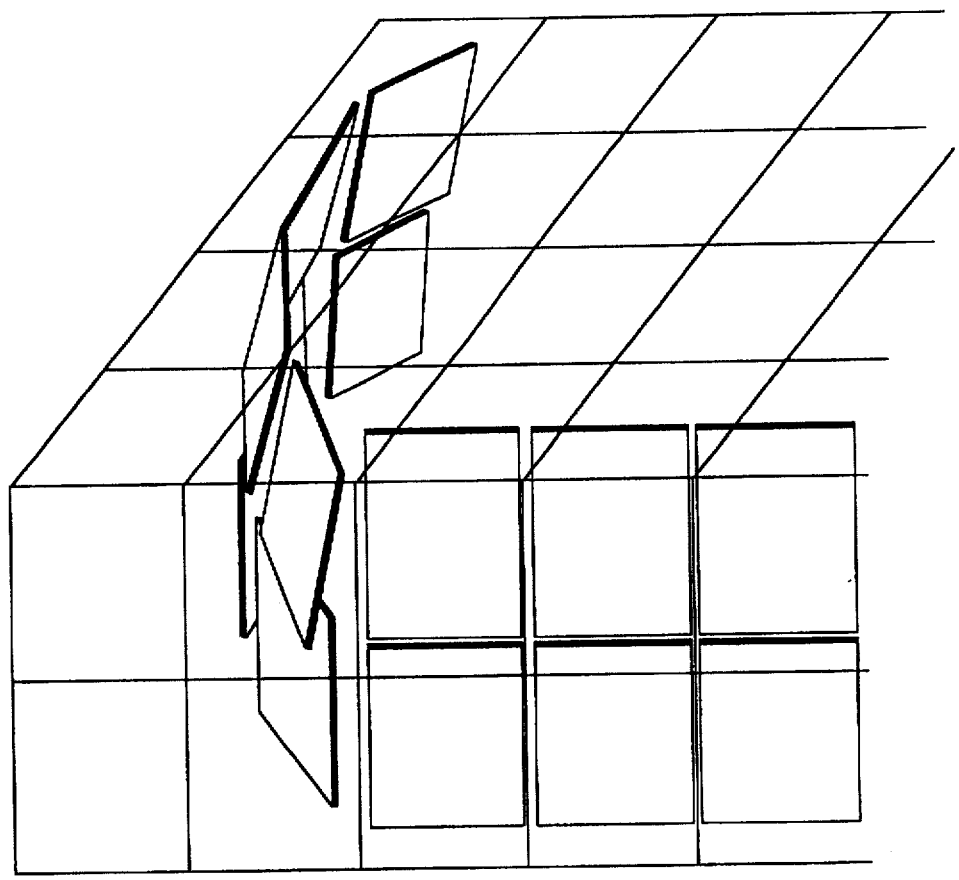
Figure 41G:
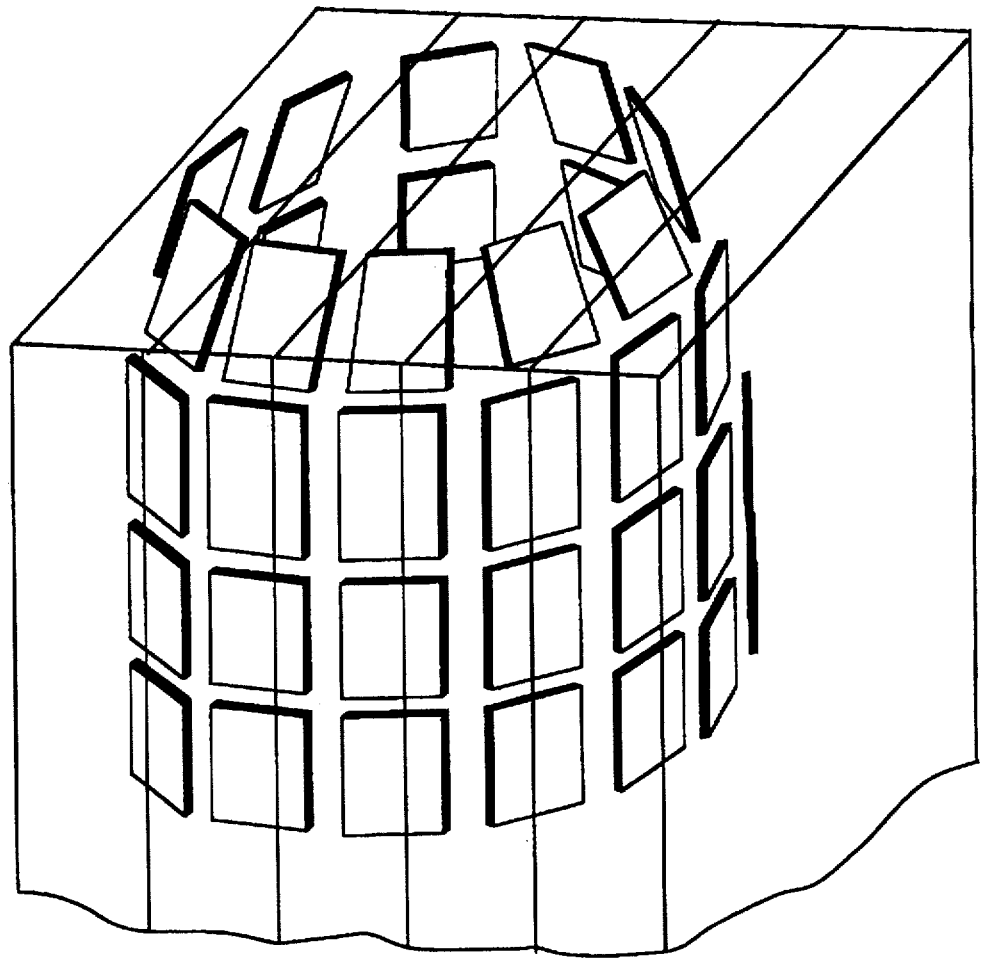

Once the generation of a normal vector and the generation of center coordinates have been performed for three pixels, these three pixels will be expressed by surface information as shown in FIG. 41E. By further repeating the procedures, the form of the surfaces of the three-dimensional object will be expressed by groups of surfaces with predetermined inclinations, as shown in FIGS. 41F and 41G.

Once the above procedures for obtaining surface information have been repeated for all of the pixels which compose the sectional image, the magnitude of the vector in the object pixel changes depending on whether the object pixel is located in the background of the original object, on the border of the original object and the background, or inside the original object.

The following is an explanation of how the compound vector of each pixel changes when the outlines in the cross-sectional images have a certain width.

Figure 42:
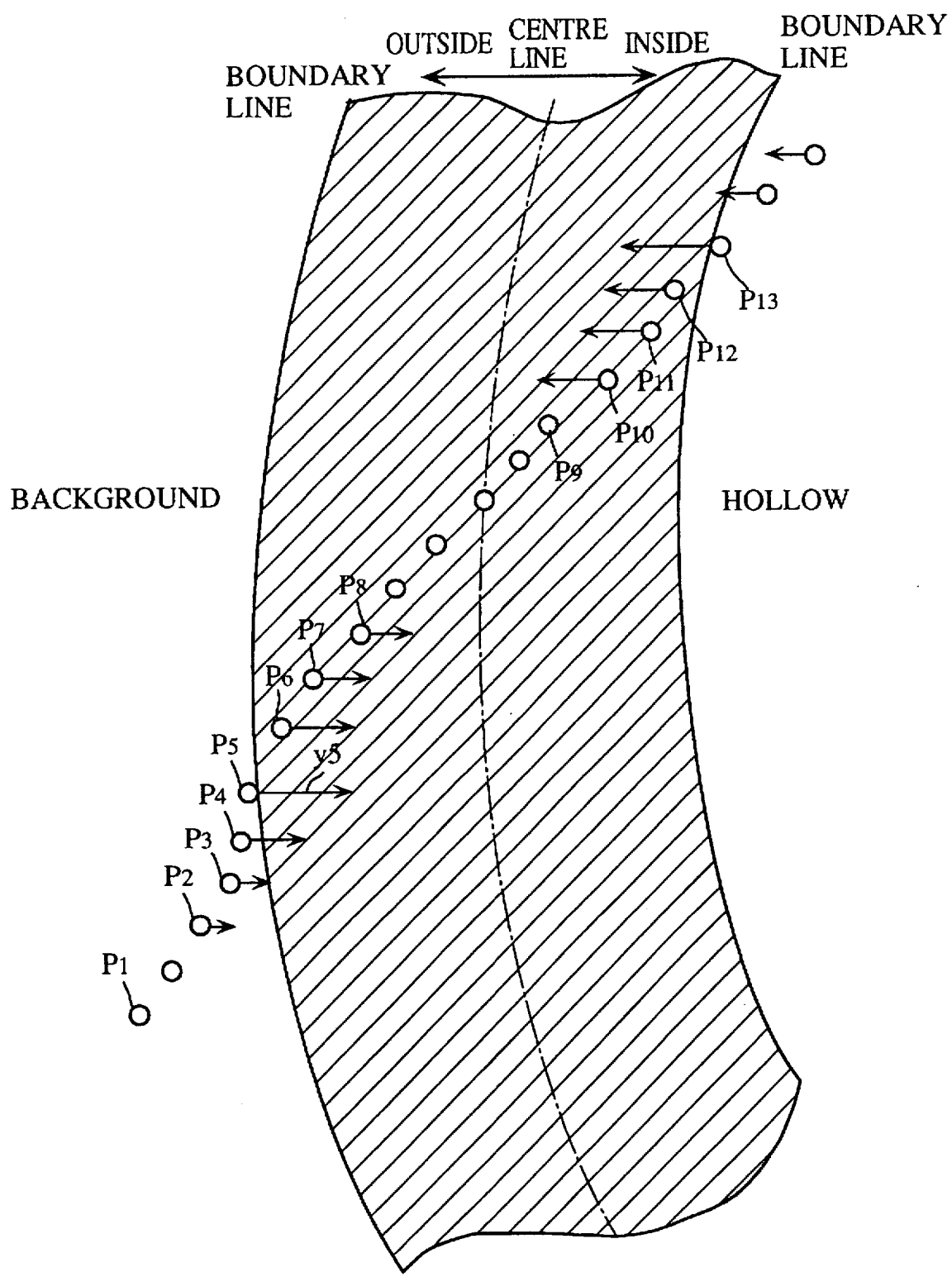
FIGS. 42 shows how the compound vector of each pixel changes when the outline of a tomogram is given a fixed thickness.

In FIG. 42, the outline of the cross-sectional image with the background is called the boundary line, and the center of the outline has been clearly marked as the "center line". The right side of the center line has been labelled as the "outside of the outline" and the left side of the center line has been labelled as the "inside of the outline".

Pixel P1 is part of the background which contains no part of the sectional image within the range of the vector search filter. At this point P1, there is almost no weighting of the unit vector in any direction, so that the magnitude of the compound vector is virtually zero.

Background pixels P2, P3, and P4, which are outside the boundary line but in its vicinity, have vectors whose magnitude increases with the vicinity of the point to the boundary line. This is because a larger number of pixels which form part of the sectional image are included in the search radius of pixels which are close to the boundary.

For pixel P5, which is on the boundary of the background and the sectional image, only the vector which points towards the sectional image will be large, so that a large inward-pointing compound vector is given, as shown by arrow y5 in FIG. 42.

Pixels P6, P7, and P8 are located in the area defined above as the outside of the outline of the sectional image, and so have compound vectors whose magnitude changes with the magnitude of the inward and outward composing vectors. Here, there is no change in the magnitude of the inward component as pixels become closer to the center line, although the outward component decreases as the pixels move away from the boundary line due to the inclusion of more pixels which are part of the sectional image in the search radius of the vector search filter. These differences in outward vectors mean that pixels have compound vectors of decreasing magnitude as they approach the center line, with pixels in the vicinity of the center line having compound vectors of magnitude zero.

Pixels P9, P10, P11, and P12 which are on the inside of the outline similarly have compound vectors whose magnitude depends on the relative strengths of the inward and outward components. As before, there is no change in the magnitude of the inward (i.e. towards the center line) component as pixels become move away from the center line, although the outward component decreases as the pixels move in such direction.

For pixel P13, which is on the boundary of the background and the sectional image, the vector which points towards the sectional image will be extremely large, with a weighting only being made to the vector which points towards the inside of the sectional image, resulting the vector with the greatest magnitude in the drawing.

Since the magnitude of the compound vector changes depending on the position of the object pixel in the sectional image, it is possible, when generating the compound vector for each pixel, to compare the magnitude of the compound vector with a fixed level and to identify the position of the pixel in the sectional image based on the result of the comparison.

In more detail, the larger the compound vector is, the more likely the pixel is located on an object-background boundary line, while the smaller the compound vector is, the more likely the pixel is located inside either the object or the background. Here, it is possible to compare the sizes of compound vectors and to generate surface information only for large vectors. By doing so, a three-dimensional object can be expressed using only surface information generated from pixels on the outlines, which requires far less information than was conventionally necessary.

The data construction of the vector search filter is explained below with reference to FIG. 43A.

The vector search filter of FIG. 43A corresponds to that used in FIG. 37, which is to say an eighteen-way filter. These eighteen vector search filters have been numbered 1–18, and each contain a fixed unit vector. The table is also composed so as to include a column for the entry of an average value for the search range of each vector search filter and for the vector after weighting. In the following explanation, each filter in the eighteen-way filter of FIG. 43A is referred to using a number j, so that a search line segment filter indicated by the number j is referred to as search line segment L(j). In the same way, the average value for a search line segment indicated by the number j is referred to as L(j).Average and the unit vector for the search line filter indicated by the number j is referred to as L(J).Unit Vec.

The data construction for each pixel in this fifth embodiment is shown in FIG. 43B. As shown in FIG. 43B, each pixel value is made up of a monochromatic brightness between 0 and 255, and a compound vector. In the following explanation, any arbitrary pixel in any of the frame memories is referred to as Pixel(x, y, z) where X, Y, and Z are the pixel's X, Y, and Z coordinates. Similarly, the pixel value of such pixel is referred to as Pixel(x, y, z).Value and the compound vector of the pixel is referred to as Pixel(x, y, z).Vector.

The surface information generated from each pixel is expressed using the data construction shown in FIG. 43C which includes the center coordinate $(x_S, y_S, z_S)$, the normal vector $(p, q, r)$, and the height $\Delta L$ and width $\Delta W$ of the surface.

In the following explanation, any arbitrary surface in any of the frame memories is referred to as Surface(x, y, z) where x, y, and z are the X, Y, and Z coordinates of the center coordinate.

The acquisition of surface information is performed by the processor 18 of personal computer 1 in accordance with the flowchart shown in FIG. 44.

As shown in FIG. 44, the X coordinate is incremented in step 403 to advance the scanning in the direction of the X axis, with step 402 incrementing the Y coordinate to slide the scanning line in the Y axis when the scanning of a line in X axis has been completed. Step 401 increments the Z coordinate to move the scanning to a next image, after one entire X-Y image has been scanned.

Steps 404 to 407 repeat the processing performed in steps 405 and 406 for every pixel Pixel (x, y, z) whose X, Y, and Z coordinates have been incremented in steps 401–403. Step 404 defines the start of a loop for the variable j which is incremented by one for each iteration to designate one of the search line segment filters L(j). In step 405, the processor 18 calculates an average value L(j).Average for the pixels included as search points for the vector search filter, and uses the calculated average value to weight the unit vector L(j).Unit Vec (L(j).Vector→L(j).Unit Vec * L(j).Average). In step 406, the vector for Pixel(x, y, z) is combined with the weighted vector (L(J). Unit Vec * L(j).Average) to give (Pixel(x, y, z).Vector →Pixel(x, y, z).Vector+L(j).Vector). Step 407 defines the end of the loop process for number j and determines whether the value of J has reached and upper limit, in which case the processing advances to step 408. When j is below this upper limit, a return to step 404 is performed.

The processing in steps 404–407 is repeated for a total number of times which is equal to the number of vector search filters, so that the unit vectors for Pixel (x, y, z) are weighted separately for the unit vector for each direction.

In step 408, the processor 18 compares the pixel vector Pixel(x, y, z).Vector combined in step 406 with a threshold value and, it exceeds the threshold value, generates surface information based on the combined pixel vector Pixel(x, y, z).Vector In step 409.

Figure 45:
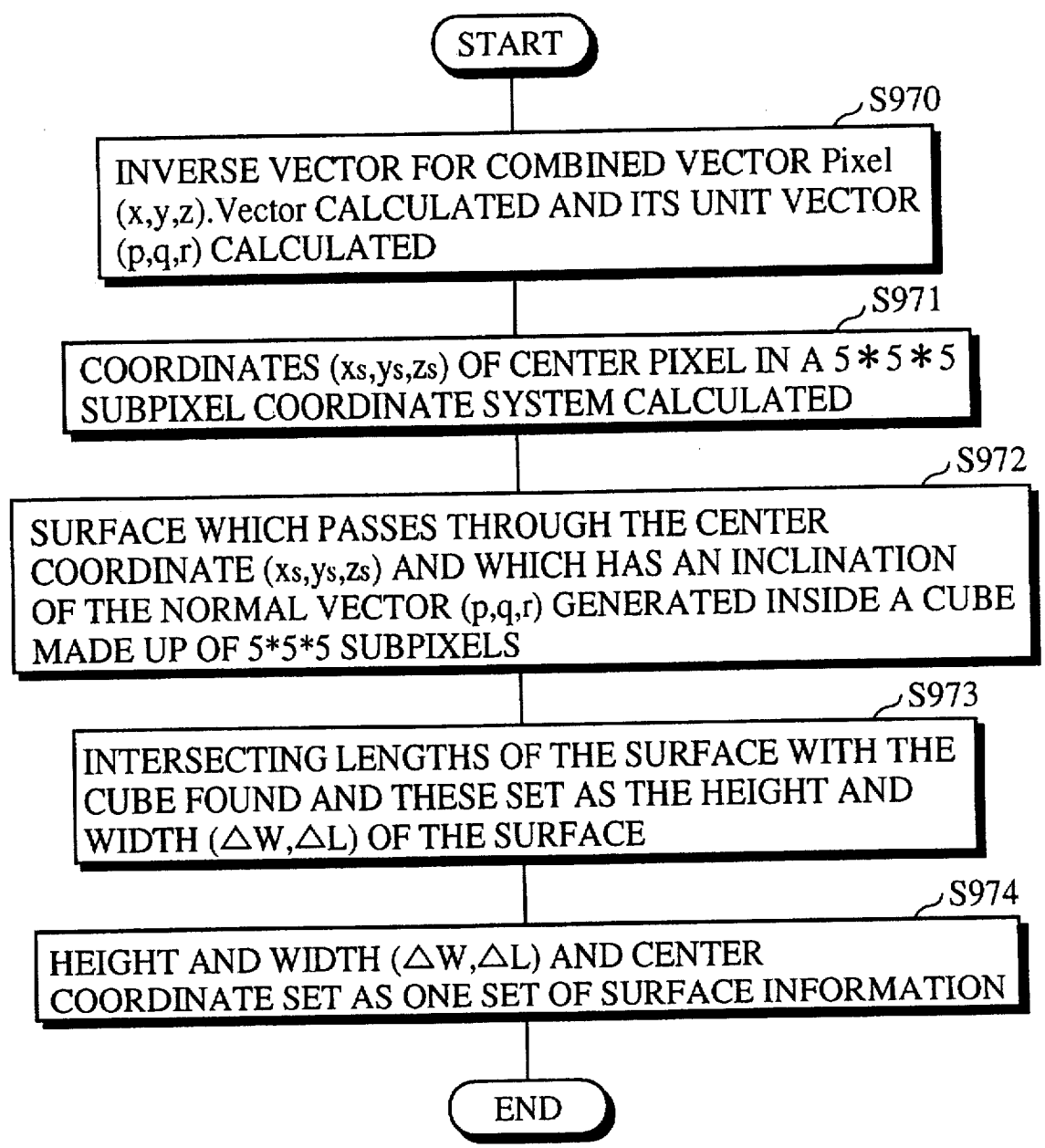
FIG. 45 shows the details of the procedure for the calculation of surface information.

Since the processing in step 409 is quite complicated, it has been divided into a plurality of subroutines which are shown in detail by the flowchart in FIG. 45. This will be referred to in the following explanation.

In step 970 of FIG. 45, an inverse vector of the compound vector Pixel(x, y, z).Vector is calculated as well as a unit vector for this inverse vector. In step 971, the processor 18 calculates the center coordinates ($x_S$, $y_S$, $z_S$) of a 5*5*5 subpixel coordinate system for the object pixel and in step 972, the processor 18 generates a surface inside the 5*5*5 subpixel system which passes through the center coordinate ($x_S$, $y_S$, $z_S$) and which has the inclination of the normal vector (p, q, r). In step 973, the length and width of the surface having an inclination 90° relative to the normal vector (p, q, r) are found and are set as the height $\Delta L$ and width $\Delta W$ of the surface. Finally, in step 974, the height $\Delta L$ and width $\Delta W$, the normal vector (p, q, r), and the center coordinates ($x_S$, $y_S$, $z_S$) are combined and are written in the memory as the surface information element Surface ($x_S$, $y_S$, $z_S$) before a return to step 410.

When it is determined in step 408 that the vector magnitude is equal to or below the predetermined threshold, the processor 18 decides that it is not possible to generate surface information for Pixel(x, y, z) and skips step 409.

When it is judged in step 410 that the x coordinate of Pixel(x, y, z) has reached an upper limit, a return to step 402 is performed, while when it is below the upper limit, a return to step 403 is performed.

By repeating this processing in steps 403–410, the processing in steps 404–409 in repeated until the x coordinate reaches the upper limit, at which point a transfer to step 402 is performed.

When it is judged in step 411 that the y coordinate of Pixel(x, y, z) has reached an upper limit, a return to step 401 is performed, while when it is below the upper limit, a return to step 402 is performed to repeat the processing in steps 402–411 until the upper limit is reached.

When it is judged in step 412 that the z coordinate of Pixel(x, y, z) has reached an upper limit, the processing is ended, while when it is below the upper limit, a return to step 401 is performed to repeat the processing in steps 401–412 until the upper limit is reached.

By repeating the processing described above, normal vectors are calculated for the pixels, out of the pixels which form the sectional images, that have compound vectors of greater magnitudes. These normal vectors are then used to express the original object.

By means of the present embodiment described above, a normal vector showing the inclination of a physical surface is calculated by analyzing the magnitude of a three-dimensional pixel value. This normal vector is then used in the surface information which expresses the original object.

While the above explanation has described the details of the first to fifth embodiments, several modifications are also possible. Examples of such are listed below.

(a) The embodiments describe the case when the average values for different search line segment filters are compared with each other and the pixel value of an object pixel is enhanced using a highest of these average values, although it should be obvious that a criterion using the pixel values searched by the search line segment filters themselves may be used.

As one example of one such criterion, a total value of the brightness of the outline may be set as a predetermined standard, with the calculated brightness values than being compared with this standard and the search line segment filter with the pixel value which best approximates to the standard brightness level then being designated. A pixel in the object image may then be enhanced using this designated search line segment filter.

The embodiments similarly describe the case where average values are calculated for the pixel values of the pixels included in search line segment filters, before being compared with each other to determine which average value is to be used to enhance the object pixel, although it is equally possible to use a weighted average. When a weighted average is used, pixel values of pixels which are close to the object pixel are given a high weighting, while pixel values of pixels which are far from the object pixel are given a low weighting, so that pixels which are closer to the object pixel have a larger effect on its average value.

(b) The conversion of a pixel into a subpixel coordinate system was only described in the second embodiment as using a twelve-way filter, although the same conversion into a subpixel coordinate system may be performed in any of the embodiments to increase the precision In any specified direction.

(b-1) As one example, a plurality of circular search paths, such as were described in the first embodiment, may be generated in a subpixel, and, by comparing the magnitudes of the average pixel values of different search paths, the pixel value of the object pixel may be enhanced using the highest average pixel value.

(b-2) In the third embodiment, when specifying the form of the surface or curved surface of the object pixel, by converting the object pixel into a subpixel coordinate system, search line segment filters at 30°,45° or 60° intervals may be arranged and the highest out of the average pixel values then used to enhance the pixel value of the object pixel.

(b-3) In the fourth embodiment
, when amending a broken section in the outline of a tomogram, by converting the object pixel into a subpixel coordinate system, search line segment filters at 30°,45° or 60° intervals may be arranged and the highest out of the average pixel values then used to enhance the pixel value of the object pixel.

(b-4) In the fifth embodiment, a plurality of unit vectors at 30°,45° or 60° intervals may be used in the subpixel coordinate system and an average value calculated by aggregating these unit vectors to generate a compound vector of an object pixel in a subpixel coordinate system.

(b-5) If the processor has sufficient processing capability and there is sufficient storage capacity in the work buffer, an 8*8, 12*12, or 16*16 subpixel coordinate system may be generated so that directions may be specified more precisely.

(c) While a storage medium was described in the present embodiments, filters may instead be distributed and marketed as a file which is delivered electronically to purchasers using FTP (File Transfer Protocol). Alternatively, a ROM containing the filters may be installed in the probe 3 to be read by a microcomputer provided in the probe 3. As another alternative, a gate array, embedded in either the probe 3 or the personal computer 1, may be provided for achieving the various filter processes.

Although the present invention has been fully described by way of examples with reference to the accompanying drawings, it is to be noted that various changes and modifications will be apparent to those skilled in the art.

Therefore, unless such changes and modifications depart from the scope of the present invention, they should be construed as being included therein.

What is claimed is:

1. An image processing apparatus which performs a process which enhances incongruous pixel values in an original image, comprising:

object pixel selecting means for selecting an object pixel out of pixels which compose the original image:

a plurality n of filter means, each of which extracts pixel values of a set of pixels, including the selected object pixel, on one of a predetermined surface and a predetermined line which pass through the object pixel, out of pixels in a predetermined range, wherein each predetermined surface and predetermined line is at a different inclination;

relative size comparing means for comparing pixels values of each set of pixels extracted by each filter means and specifying a filter means whose pixel values best approximate to a predetermined standard; and first pixel value enhancing means for enhancing a pixel value of the object pixel based on only the pixel values of the specified filter means.

2. The image processing apparatus of claim 1, wherein each of the plurality n of filter means has a window for extracting the pixel values of pixels, including the object pixel, aligned in one out of a plurality n directions.

3. The image processing apparatus of claim 2, wherein a position of the object pixel in the original image is expressed as absolute coordinate in a coordinate system composed of a plurality of standard axes, and wherein each filter means includes:

a relative coordinate array storage unit for storing a plurality of arrays of relative coordinates which express a direction and form of a corresponding window, wherein each relative coordinate shows a displacement amount in each of the standard axes from the object pixel to a pixel whose pixel value is to be extracted, and each array of relative coordinates shows the direction and form of the corresponding window using a combination of a plurality of displacement amounts;

a retrieving unit for retrieving one relative coordinate out of an array of relative coordinates stored by the relative coordinate array storage unit;

a pixel value reading unit for adding the displacement amounts shown by the retrieved relative coordinate to the absolute coordinate of the object pixel, and for reading a pixel value of a pixel which has the coordinate given by the addition; and a control unit for having said retrieving unit to retrieve a next relative coordinate after a pixel value has been road by the pixel value reading unit.

4. The image processing apparatus of claim 3, wherein the object pixel selecting means repeats an operation to select a pixel in the original image which has not yet been selected as an object pixel, when enhancement of the pixel value of a previous object pixel has been completed, wherein the image processing apparatus further comprises enhanced data storage means for storing enhanced image data, and wherein once a pixel value of an object pixel has been enhanced, the first pixel value enhancing means rewrites a pixel value of a pixel in the enhanced data storage means which corresponds to said object pixel using said enhanced pixel value.

5. The image processing apparatus of claim 4, further comprising:

judging means for judging whether the pixel values extracted by each filter means are below a threshold value which indicates noise; and second pixel value enhancing means for enhancing the pixel value of the object pixel to a predetermined low brightness level when the judging means judges that none of the filter means has extracted pixel values which satisfy said threshold value.

6. The image processing apparatus of claim 5, wherein the relative size comparing means includes:

an average value calculating unit for calculating an average value of the pixel values of the set of pixels extracted by each filter means; and a specifying unit for setting possession of a highest average value as the predetermined standard and for specifying a filter means which has a highest average value.

7. The image processing apparatus of claim 6, wherein the judging means judges whether an average value calculated for the pixel values extracted by each filter means is below a threshold value, and the second pixel value enhancing means enhances the pixel value of the object pixel to a predetermined low brightness level when the judging means judges that none of the filter means has a calculated average pixel value which satisfies said threshold value.

8. The image processing apparatus of claim 1, wherein each of the n filter means has a window for extracting pixel values of pixels aligned in a form which corresponds to one out of a plurality n of divisions of a specified contour line.

9. The image processing apparatus of claim 8, wherein a position of the object pixel in the original image is expressed as absolute coordinate in a coordinate system composed of a plurality of standard axes, and wherein each filter means includes:

a relative coordinate array storage unit for storing a plurality of arrays of relative coordinates which express a direction and form of a corresponding window, wherein each relative coordinate shows a displacement amount in each of the standard axes from the object pixel to a pixel whose pixel value is to be extracted, and each array of relative coordinates shows the direction and form of the corresponding window using a combination of a plurality of displacement amounts;

a retrieving unit for retrieving one relative coordinate out of an array of relative coordinates stored by the relative coordinate array storage unit;

a pixel value reading unit for adding the displacement amounts shown by the retrieved relative coordinate to the absolute coordinate of the object pixel, and for reading a pixel value of a pixel which has the coordinate given by the addition; and a control unit for having said retrieving unit to retrieve a neat relative coordinate after a pixel value has been read by the pixel value reading unit.

10. The image processing apparatus of claim 9, wherein the object pixel selecting means repeats an operation to select a pixel in the original image which has not yet been selected as an object pixel, when enhancement of the pixel value of a previous object pixel has been completed, wherein the image processing apparatus further comprises enhanced data storage means for storing enhanced image data, and wherein once a pixel value of an object pixel has been enhanced, the first pixel value enhancing means rewrites a pixel value of a pixel in the enhanced data storage means which corresponds to said object pixel using said enhanced pixel value.

11. The image processing apparatus of claim 10, further comprising:
   judging meant for judging whether the pixel values extracted by each filter means are below a threshold value which indicates noise; and
   second pixel value enhancing means for enhancing the pixel value of the object pixel to a predetermined low brightness level when the judging means judges that none of the filter means has extracted pixel values which satisfy said threshold value.

12. The image processing apparatus of claim 11, wherein the relative size comparing means includes:
   an average value calculating unit for calculating an average value of the pixel values of the set of pixels extracted by each filter means; and
   a specifying unit for setting possession of a highest average value as the predetermined standard and for specifying a filter means which has a highest average value.

13. The image processing apparatus of claim 12, wherein the judging means judges whether an average value calculated for the pixel values extracted by each filter means is below a threshold value, and the second pixel value enhancing means enhances the pixel value of the object pixel to a predetermined low brightness level when the judging means judges that none of the filter means has a calculated average pixel value which satisfies said threshold value.

14. The image processing apparatus of claim 1, wherein the original image is of a three-dimensional object, and each of the n filter means extracts pixel values of a set of pixels which are present on one out of n surfaces, each surface being a cross-section of the three-dimensional object which has the object pixel as a center of the surface.

15. The image processing apparatus of claim 14, wherein a position of the object pixel in the original image is expressed as absolute coordinate in a coordinate system composed of a plurality of standard axes, and wherein each filter means includes:
   a relative coordinate array storage unit for storing a plurality of arrays of relative coordinates which express a direction and form of a corresponding window, wherein each relative coordinate shows a displacement amount in each of the standard axes from the object pixel to a pixel whose pixel value is to be extracted, and each array of relative coordinates shows the direction and form of the corresponding window using a combination of a plurality of displacement amounts;
   a retrieving unit for retrieving one relative coordinate out of an array of relative coordinates stored by the relative coordinate array storage unit;
   a pixel value reading unit for adding the displacement amounts shown by the retrieved relative coordinate to the absolute coordinate of the object pixel, and for reading a pixel value of a pixel which has the coordinate given by the addition; and
   a control unit for having said retrieving unit to retrieve a next relative coordinate after a pixel value has been read by the pixel value reading unit.

16. The image processing apparatus of claim 15, wherein the object pixel selecting means repeats an operation to select a pixel in the original image which has not yet been selected as an object pixel, when enhancement of the pixel value of a previous object pixel has been completed, wherein the image processing apparatus further comprises enhanced data storage means for storing enhanced image data, and wherein once a pixel value of an object pixel has been enhanced, the first pixel value enhancing means rewrites a pixel value of a pixel in the enhanced data storage means which corresponds to said object pixel using said enhanced pixel value.

17. The image processing apparatus of claim 16, wherein further comprising:
   judging means for judging whether the pixel values extracted by each filter means are below a threshold value which indicates noise: and
   second pixel value enhancing means for enhancing the pixel value of the object pixel to a predetermined low brightness level when the judging means judges that none of the filter means has extracted pixel values which satisfy said threshold value.

18. The image processing apparatus of claim 17, wherein the relative size comparing means includes:
   an average value calculating unit for calculating an average value of the pixel values of the set of pixels extracted by each filter means; and
   a specifying unit for setting possession of a highest average value as the predetermined standard and for specifying a filter means which has a highest average value.

19. The image processing apparatus of claim 18, wherein the judging means judges whether an average value calculated for the pixel values extracted by each filter means is below a threshold value, and the second pixel value enhancing means enhances the pixel value of the object pixel to a predetermined low brightness level when the judging means judges that none of the filter means has a calculated average pixel value which satisfies said threshold value.

20. An image processing apparatus which performs a process which enhances incongruous pixel values in an original image, said image processing apparatus comprising:
   object pixel selecting means for selecting an object pixel out of pixels which compose the original image;
   striplike area rotating mean for rotating a striplike area in a detailed coordinate system about the object pixel by a specified angle per rotation, wherein the detailed coordinate system is a coordinate system in which each pixel in the original image is expressed using a plurality of coordinate values which represent a two-dimensional region;
   pixel detecting means for calculating an intersecting area of a rotated striplike area and a region of each pixel in the original image;
   distributing means for assigning a weighting to a pixel value of each pixel whose region intersects the rotated striplike area, said weighting corresponding to a degree to which the rotated striplike area coincides with the region of the pixel;
   indicating means for indicating a rotation of the striplike area to the striplike area rotating means, after pixel values have been weighted by the distributing means;
   relative size comparing means for comparing, when rotating by the striplike area rotating means has been repeated a predetermined number of times, weighted results for each rotation of the striplike area, and specifying a rotation whose weighted pixel values best approximate to a predetermined standard; and
   first pixel value enhancing means for enhancing the pixel value of the object pixel based on only the weighted pixel values of the specified filter means.

21. The image processing apparatus of claim 20,
wherein the object pixel selecting means repeats an operation to select a pixel in the original image which has not yet been selected as an object pixel, when enhancement of the pixel value of a previous object pixel has been completed, wherein the image processing apparatus further comprises enhanced data storage means for storing enhanced image data, and wherein once a pixel value of an object pixel has been enhanced, the first pixel value enhancing means rewrites a pixel value of a pixel in the enhanced data storage means which corresponds to said object pixel using said enhanced pixel value.

22. The image processing apparatus of claim 21, further comprising:

judging means for judging whether pixel values weighted by the distributing means are below a threshold value which indicates noise; and second pixel value enhancing means for enhancing the pixel value of the object pixel to a predetermined low brightness level when the judging means judges that none of the rotations has weighted pixel values which satisfy said threshold value.

23. The image processing apparatus of claim 22, wherein the relative size comparing means includes:

a weighting unit for assigning a weighting to a pixel value of each pixel whose region intersects the rotated striplike area, said weighting corresponding to a degree to which the rotated striplike area coincides with the corresponding pixel;

an average value calculating unit for calculating an average value of the weighted pixel values; and a specifying unit for setting possession of a highest average value as the predetermined standard and for specifying a rotation with a highest average value.

24. The image processing apparatus of claim 23, wherein the judging means judges whether an average value calculated for the weighted pixel values is below a threshold value, and the second pixel value enhancing means enhances the pixel value of the object pixel to a predetermined low brightness level when the judging means judges that the calculated average value of none of the rotations by the striplike area rotating means satisfies said threshold value.

25. An image processing apparatus which performs a process which enhances incongruous pixel values in an original image, said image processing apparatus comprising;

object pixel selecting means for selecting an object pixel out of pixels which compose the original image;

striplike area rotating means for rotating a striplike area in a detailed coordinate system about the object pixel by a specified angle per rotation, wherein the detailed coordinate system is a coordinate system in which each pixel in the original image is expressed using a plurality of coordinate values which represent a two-dimensional region, and wherein the striplike area is one out of a plurality n divisions of a specified curved region;

pixel detecting means for calculating an intersecting area of a rotated striplike area and a region of each pixel in the original image;

distributing means for assigning a weighting to a pixel value of each pixel whose region intersects the rotated striplike area, said weighting corresponding to a degree to which the rotated striplike area coincides with the region of the pixel;

indicating means for indicating a rotation of the striplike area to the striplike area rotating means, after pixel values have been weighted by the distributing means;

relative size comparing means for comparing, when rotating by the striplike area rotating means has been repeated a predetermined number of times, weighted results for each rotation of the striplike area, and specifying a rotation whose weighted pixel values best approximate to a predetermined standard; and first pixel value enhancing means for enhancing the pixel value of the object pixel based on only the weighted pixel values of the specified filter means.

26. The image processing apparatus of claim 25, wherein the object pixel selecting means repeats an operation to select a pixel in the original image which has not yet been selected as an object pixel, when enhancement of the pixel value of a previous object pixel has been completed, wherein the image processing apparatus further comprises enhanced data storage means for storing enhanced image data, and wherein once a pixel value of an object pixel has been enhanced, the first pixel value enhancing means rewrites a pixel value of a pixel in the enhanced data storage means which corresponds to said object pixel using said enhanced pixel value.

27. The image processing apparatus of claim 26, further comprising:

judging means for judging whether pixel values weighted by the distributing means are below a threshold value which indicates noise; and second pixel value enhancing means for enhancing the pixel value of the object pixel to a predetermined low brightness level when the judging means judges that none of the rotations has weighted pixel values which satisfy said threshold value.

28. The image processing apparatus of claim 27, wherein the relative size comparing means includes:

a weighting unit for assigning a weighting to a pixel value of each pixel whose region intersects the rotated striplike area, said weighting corresponding to a degree to which the rotated striplike area coincides with the corresponding pixel;

an average value calculating unit for calculating an average value of the weighted pixel values; and a specifying unit for setting possession of a highest average value as the predetermined standard and for specifying a rotation with a highest average value.

29. The image processing apparatus of claim 28, wherein the judging means judges whether an average value calculated for the weighted pixel values is below a threshold value, and the second pixel value enhancing means enhances the pixel value of the object pixel to a predetermined low brightness level when the judging means judges that the calculated average value of none of the rotations by the striplike area rotating means satisfies said threshold value.

30. An image processing apparatus which performs a process which enhances incongruous pixel values in an original image, said image processing apparatus comprising:

object pixel selecting means for selecting an object pixel out of pixels which compose the original image;

surface rotating means for rotating a surface in a detailed coordinate system about the object pixel by a specified angle per rotation, wherein the detailed coordinate system is a coordinate system in which each pixel in the original image is expressed using a plurality of coordinate values which represent a two-dimensional region;

pixel detecting means for calculating an intersecting area of a rotated surface and a region of each pixel in the original image;

distributing means for assigning a weighting to a pixel value of each pixel whose region intersects the rotated surface, said weighting corresponding to a degree to which the rotated surface coincides with the region of the pixel;

indicating means for indicating a rotation of the surface to the surface rotating means, after pixel values have been weighted by the distributing means;

relative size comparing means for comparing, when rotating by the surface rotating means has been repeated a predetermined number of times, weighted results for each rotation of the surface, and specifying a rotation whose weighted pixel values best approximate to a predetermined standard; and first pixel value enhancing means for enhancing the pixel value of the object pixel based on only the weighted pixel values of the specified filter means.

31. The image processing apparatus of claim 30, wherein the object pixel selecting means repeats an operation to select a pixel in the original image which has not yet been selected as an object pixel, when enhancement of the pixel value of a previous object pixel has been completed, wherein the image processing apparatus further comprises enhanced data storage means for storing enhanced image data, and wherein once a pixel value of an object pixel has been enhanced, the first pixel value enhancing means rewrites a pixel value of a pixel in the enhanced data storage means which corresponds to said object pixel using said enhanced pixel value.

32. The image processing apparatus of claim 31, further comprising:

judging means for judging whether pixel values weighted by the distributing means are below a threshold value which indicates noise; and second pixel value enhancing means for enhancing the pixel value of the object pixel to a predetermined low brightness level when the judging means judges that none of the rotations has weighted pixel values which satisfy said threshold value.

33. The image processing apparatus of claim 32, wherein the relative size comparing means includes:

a weighting unit for assigning a weighting to a pixel value of each pixel whose region intersects the rotated striplike area, said weighting corresponding to a degree to which the rotated striplike area coincides with the corresponding pixel;

an average value calculating unit for calculating an average value of the weighted pixel values; and a specifying unit for setting possession of a highest average value as the predetermined standard and for specifying a rotation with a highest average value.

34. The image processing apparatus of claim 33, wherein the judging means judges whether an average value calculated for the weighted pixel values is below a threshold value, and the second pixel value enhancing means enhances the pixel value of the object pixel to a predetermined low brightness level when the judging means judges that the calculated average value of none of the rotations by the striplike area rotating means satisfies said threshold value.

35. An image processing apparatus for enhancing an image of a three-dimensional body which is expressed by a plurality of sectional images which have been stacked together, said image processing apparatus comprising:

first planar image generating means, set in a first direction which is at an angle to a stacking direction of the stacked plurality of sectional images, which is moved in the first direction across the image of the three-dimensional body to generate a plurality of first-direction planar images of the three-dimensional body;

first enhancing means for enhancing each of the first-direction planar images and stacking the enhanced first-direction planar images in the first direction to generate a first enhanced image of the three-dimensional body;

is second planar image generating means, set in a second direction which is perpendicular to the first direction, which is moved in the second direction across the first enhanced image of the three-dimensional body to generate a plurality of second-direction planar images;

second enhancing means for enhancing each of the second-direction planar images and stacking the enhanced second-direction planar images in the second direction to generate a second enhanced image of the three-dimensional body;

third planar image generating means, set in a third direction which is perpendicular to the first direction and to the second direction, which is moved in the third direction across the second enhanced image of the three-dimensional body to generate a plurality of third-direction planar images; and third enhancing means for enhancing each of the third-direction planar images and stacking the enhanced third-direction planar images in the third direction to generate a third enhanced image of the three-dimensional body.

36. The image processing apparatus of claim 35, wherein each of the first, second and third enhancing means includes:

object pixel selecting means for selecting an object pixel out of pixels which compose a planar image;

a plurality n filter means for extracting pixel values of an array of pixels which are located on one out of a plurality n of predetermined lines which pass through the object pixel, out of the object pixel and pixels in a vicinity of the object pixel, wherein each of the predetermined lines has a different inclination;

relative size comparing means for comparing the pixel values extracted by each of the n filter means and specifying one filter means whose extracted pixel values best approximate to a predetermined standard; and first pixel value enhancing means for enhancing the pixel value of the object pixel based on only the pixel values of the specified filter means.

37. The image processing apparatus of claim 36, wherein the image processing apparatus further comprises enhanced data storage means for storing enhanced image data, and wherein once a pixel value of an object pixel has been enhanced, the first pixel value enhancing means rewrites a pixel value of a pixel in the enhanced data storage means which corresponds to said object pixel using said enhanced pixel value.

38. The image processing apparatus of claim 37, further comprising:

judging means for judging whether the pixel values extracted by each filter means are below a threshold value which indicates noise; and second pixel value enhancing means for enhancing the pixel value of the object pixel to a predetermined low brightness level when the judging means judges that none of the filter means has extracted pixel values which satisfy said threshold value.

39. An image processing apparatus for expressing a three-dimensional image, formed by stacking sectional images, as sets of surface information, each of which is made up of a normal vector and spatial coordinates, said image processing apparatus comprising:

unit vector providing means for providing a plurality of unit vectors to each pixel which forms a part of a sectional image, wherein each unit vector shows one of a plurality of spatial directions;

weighting means for analyzing how pixel values are distributed in each direction for a pixel and weighting each of the unit vectors provided to the pixel in accordance with the analysis result;

combining means for combining the weighted unit vectors for every pixel; and surface information generating means for generating sets of surface information which each include spatial coordinates for a pixel and a normal vector which is based on the vector combined by the combining means for the pixel.

40. The image processing apparatus of claim 39, wherein the weighting means includes:

an average calculating unit for calculating an average value for pixel values in each direction for a pixel; and a weighting unit for weighting, when an average value in a direction is equal to or greater than a threshold value, a unit vector in a corresponding direction using the calculated average value.

41. The image processing apparatus of claim 40, further comprising skip means for skipping generation of surface information for a pixel when, for the pixel, an average value in every direction is below the threshold value.

42. An image processing method which uses a computer and which enhances incongruous pixel values in an original image, comprising:

an object pixel selecting step for selecting an object pixel out of pixels which compose the original image;

an extraction step for extracting pixel values of a set of pixels, including the selected object pixel, on one of a predetermined surface and a predetermined line which pass through the object pixel, out of pixels in a predetermined range;

a switching step for repeatedly having the extracting step performed, changing an inclination of one of a line and surface each time;

a relative size comparing step for comparing pixels values of each set of pixels extracted in each extracting step and specifying one execution of the extracting step whose pixel values best approximate to a predetermined standard; and a first pixel value enhancing step for enhancing a pixel value of the object pixel based on only the pixel values of the specified execution of the extracting step.

43. The image processing method of claim 42, further comprising:

a judging step for judging whether the pixel values extracted by each execution of the extracting step are below a threshold value which indicates noise; and a second pixel value enhancing step for enhancing the pixel value of the object pixel to a predetermined low brightness level when the judging stop judges that none of the executions of the extracting step has extracted pixel values which satisfy said threshold value.

44. The image processing method of claim 43, wherein the relative size comparing step includes:

an average value calculating substep for calculating an average value of the pixel values of the set of pixels extracted by each execution of the extracting step; and a specifying substep for setting possession of a highest average value as the predetermined standard and for specifying an execution of the extracting step which has a highest average value.

45. The image processing method of claim 44, wherein the judging step judges whether an average value calculated for the pixel values extracted by execution of the extracting step is below a threshold value, and the second pixel value enhancing step enhances the pixel value of the object pixel to a predetermined low brightness level when the judging step judges that none of the executions of the extracting step has a calculated average pixel value which satisfies said threshold value.

46. An image processing method which enhances incongruous pixel values in an original image, comprising:

an object pixel selecting step for selecting an object pixel out of pixels which compose the original image;

a striplike area rotating step for rotating a striplike area in a detailed coordinate system about the object pixel by a specified angle per rotation, wherein the detailed coordinate system is a coordinate system in which each pixel in the original image is expressed using a plurality of coordinate values which represent a two-dimensional region;

a pixel detecting step for calculating an intersecting area of a rotated striplike area and a region of each pixel in the original image;

a distributing step for assigning a weighting to a pixel value of each pixel whose region intersects the rotated striplike area, said weighting corresponding to a degree to which the rotated striplike area coincides with the region of the pixel;

an indicating step for indicating a rotation of the striplike area to the striplike area rotating step, after pixel values have been weighted by the distributing step;

a relative size comparing stop for comparing, when rotating by the striplike area rotating step has been repeated a predetermined number of times, weighted results for each rotation of the striplike area, and specifying a rotation whose weighted pixel values best approximate to a predetermined standard; and a first pixel value enhancing step for enhancing the pixel value of the object pixel based on only the weighted pixel values of the specified rotation.

47. The image processing method of claim 46, wherein the relative size comparing step includes:

a weighting substep for assigning a weighting to a pixel value of each pixel whose region intersects the rotated striplike area, said weighting corresponding to a degree to which the rotated striplike area coincides with the corresponding pixel;

an average value calculating substep for calculating an average value of the weighted pixel values; and a specifying substep for setting possession of a highest average value as the predetermined standard and for specifying a rotation with a highest average value.

48. The image processing method of claim 47, further comprising:

a judging step judging whether the pixel values weighted by every execution of the distributing step are below a threshold value which indicates noise; and a second pixel value enhancing step for enhancing the pixel value of the object pixel to a predetermined low brightness level when the judging step judges that none of the executions of the weighting step has weighted pixel values which satisfy said threshold value.

49. An image processing method for enhancing an image of a three-dimensional body which expressed by a plurality of sectional images which have been stacked together, said image processing method comprising:

a first planar image generating step, set in a first direction which is at an angle to a stacking direction of the stacked plurality of sectional images, which moves in the first direction across the image of the three-dimensional body to generate a plurality of first-direction planar images of the three-dimensional body;

a first enhancing step for enhancing each of the first-direction planar images and stacking the enhanced first-direction planar images in the first direction to generate a first enhanced image of the three-dimensional body;

a second planar image generating step, set in a second direction which is perpendicular to the first direction, which moves in the second direction across the first enhanced image of the three-dimensional body to generate a plurality of second-direction planar images;

a second enhancing step for enhancing each of the second-direction planar images and stacking the enhanced second-direction planar images in the second direction to generate a second enhanced image of the three-dimensional body;

a third planar image generating step, set in a third direction which is perpendicular to the first direction and to the second direction, which is moved in the third direction across the second enhanced image of the three-dimensional body to generate a plurality of third-direction planar images; and a third enhancing step for enhancing each of the third-direction planar images and stacking the enhanced third-direction planar images in the third direction to generate a third enhanced image of the three-dimensional body.

50. The image processing method of claim 49, wherein each of the first, second and third enhancing steps includes:

an object pixel selecting substep for selecting an object pixel out of pixels which compose a planar image;

an extracting substep for extracting pixel values of an array of pixels which are located on one of a predetermined line and a predetermined surface which pass through the object pixel, out of the object pixel and pixels in a vicinity of the object pixel;

a switching step for repeatedly having the extracting substep performed, changing an inclination of one of a line and surface each time;

a relative size comparing substep for comparing the pixel values extracted by each execution of the extracting substep and specifying one execution whose extracted pixel values best approximate to a predetermined standard; and a first pixel value enhancing substep for enhancing the pixel value of the object pixel based on only the pixel values of the specified execution of the extracting substep.

51. The image processing method of claim 50, wherein each of the first, second and third enhancing steps further includes:

a judging substep for judging whether the pixel values extracted by each execution of the extracting substep are below a threshold value which indicates noise; and a second pixel value enhancing substep for enhancing the pixel value of the object pixel to a predetermined low brightness level when the judging substep judges that none of executions of the extracting substep has extracted pixel values which satisfy said threshold value.

52. The image processing method of claim 51, wherein the relative size comparing step includes:

an average value calculating substep for calculating an average value of the pixel values of the set of pixels extracted by each execution of the extracting step; and a specifying substep for setting possession of a highest average value as the predetermined standard and for specifying an execution of the extracting step which has a highest average value.

53. The image processing method of claim 52, wherein the judging substep judges whether an average value calculated for the pixel values extracted by every execution of the extracting step are below a threshold value which indicates noise, and the second pixel value enhancing substep enhances the pixel value of the object pixel to a predetermined low brightness level when the judging substep judges that none of the executions of the extracting substep has a calculated average pixel value which satisfies said threshold value.

54. An image processing method for expressing a three-dimensional image, formed by stacking sectional images, as sets of surface information, each of which is made up of a normal vector and spatial coordinates, said image processing method comprising:

a unit vector providing step for providing a plurality of unit vectors to each pixel which forms a part of a sectional image, wherein each unit vector shows one of a plurality of spatial directions;

a weighting step for analyzing how pixel values are distributed in each direction for a pixel and weighting each of the unit vectors provided to the pixel in accordance with the analysis result;

a combining step for combining the weighted unit vectors for every pixel; and a surface information generating step for generating sets of surface information which each include spatial coordinates for a pixel and a normal vector which is based on the vector combined by the combining step for the pixel.

55. The image processing method of claim 54, wherein the weighting step includes:

an average calculating step for calculating an average value for pixel values in each direction for a pixel; and a weighting step for weighting, when an average value in a direction is equal to or greater than a threshold value, a unit vector in a corresponding direction using the calculated average value.

56. The image processing method of claim 55, further comprising skip stop for skipping generation of surface information for a pixel when, for the pixel, an average value in every direction is below the threshold value.

* * * * *